US009682105B2

(12) United States Patent
Le et al.

(10) Patent No.: US 9,682,105 B2
(45) Date of Patent: Jun. 20, 2017

(54) METHODS OF PROMOTING WOUND HEALING AND ATTENUATING CONTACT HYPERSENSITIVITY WITH GINGIVA-DERIVED MESENCHYMAL STEM CELLS

(75) Inventors: Anh D. Le, La Mirada, CA (US); Qunzhou Zhang, San Gabriel, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 550 days.

(21) Appl. No.: 13/809,876

(22) PCT Filed: Jul. 14, 2011

(86) PCT No.: PCT/US2011/044085
§ 371 (c)(1),
(2), (4) Date: Jul. 29, 2013

(87) PCT Pub. No.: WO2012/009581
PCT Pub. Date: Jan. 19, 2012

(65) Prior Publication Data
US 2013/0295058 A1 Nov. 7, 2013

Related U.S. Application Data

(60) Provisional application No. 61/364,339, filed on Jul. 14, 2010.

(51) Int. Cl.
*A01N 63/00* (2006.01)
*A61K 35/28* (2015.01)
(52) U.S. Cl.
CPC .................... *A61K 35/28* (2013.01)
(58) Field of Classification Search
None
See application file for complete search history.

(56) References Cited

U.S. PATENT DOCUMENTS

2009/0208463 A1* 8/2009 Pittenger et al. ............ 424/93.7
2009/0232773 A1 9/2009 Kato et al. .................. 424/93.7
2010/0080780 A1 4/2010 Pitaru

FOREIGN PATENT DOCUMENTS

CN 101144069 A 3/2008
WO WO2008132722 A1 11/2008

OTHER PUBLICATIONS

Tomar et al., "Human gingiva-derived mesenchymal stem cells are superior to bone marrow-derived mesenchymal stem cells for cell therapy in regenerative medicine", Biochem Biophys Res Commun, Epub Feb. 6, 2010, 393(3); pp. 377-383.
Zhang et al., "Mesenchymal Stem Cells Derived from Human Gingiva are capable of immunomodulatory functions and ameliorate inflammation-related tissue destruction in experimental colitis", J Immunol. 2009, 183(12): pp. 7787-7798.
Huang et al., "Mesenchymal Stem Cells Deprived from Dental Tissue vs. Those from Other Sources: Their Biology and Role in Regenerative Medicine", JDR 2009, 88(9): pp. 792-806.
Peng et al., "Mesenchymal Stem Cells and Tooth Engineering", International Journal of Oral Science 2009, pp. 6-12.
Abdallah et al. 2009. The Use of Mesenchymal (Skeletal) Stem Cells for Treatment of Degenerative Diseases: Current Status and Future Perspectives. Journal of Cellular Physiology, vol. 218, pp. 9-12.
Aggarwal et al. 2005. Human Mesenchymal Stem Cells Modulate Allogeneic Immune Cell Responses. Blood, vol. 105, pp. 1815-1822.
Alex et al. 2009. Distinct Cytokine Patterns Identified from Multiplex Profiles of Murine DSS and TNBS-induced Colitis. Inflamm. Bowel Dis., vol. 15, No. 3, Mar. 2009, pp. 341-352.
Bartsch, Jr. et al. 2005. Rapid Communication: Propagation, Expansion, and Multilineage Differentiation of Human Somatic Stem Cells from Dermal Progenitors. Stem Cells and Development, vol. 14, pp. 337-348.
Beltrami et al. 2007. Multipotent Cells Can Be Generated In Vitro From Several Adult Human Organs (Heart, Liver, and Bone Marrow). Blood, vol. 110, pp. 3438-3446.
Bi et al. 2007. Identification of Tendon Stem/Progenitor Cells and the Role of the Extracellular Matrix in Their Niche. Nature Medicine, vol. 13, No. 10, Oct. 2007, pp. 1219-1227.
Chang et al. 2007. Placenta-Derived Multipotent Cells Exhibit Immunosuppressive Properties That Are Enhanced in the Presence of Interferon-gamma. Stem Cells, No. 24, pp. 2466-2477.
Cipriani et al. 2007. Impairment of Endothelial Cell Differentiation from Bone Marrow-Derived Mesenchymal Stem Cells. Arthritis & Rheymatism, vol. 56, No. 6, Jun. 2007, pp. 1994-2004.
Cournil-Henrionnet et al. Phenotypic Analysis of Cell Surface Markers and Gene Expression of Human Mesenchymal Stem Cells During Monolayer Expansion. Poster 180, Osteoarthritis and Cartilage, vol. 17, Supplement 1, pp. S105-S106.

(Continued)

*Primary Examiner* — Blaine Lankford
(74) *Attorney, Agent, or Firm* — McDermott Will & Emery LLP

(57) ABSTRACT

Disclosed are methods of polarizing macrophages to exhibit M2 phenotype, including introducing an effective amount of gingiva-derived mesenchymal stem cells to an environment comprising a population of macrophages such that the macrophages are in fluid communication with the gingiva-derived mesenchymal stem cells. Also disclosed are methods of promoting cutaneous wound healing including administering to a patient an effective amount of human gingiva-derived mesenchymal stem cells, thereby resulting in at least one of accelerated wound closure, rapid re-epithelialization, improved angiogenesis and improved tissue remodeling relative to untreated controls. Also disclosed are methods for attenuating contact hypersensitivity in a patient, the methods including administering to a patient an effective amount of human gingiva-derived mesenchymal stem cells at a time at least timeframe selected from the group consisting of before sensitization, after sensitization and before challenge and after challenge, thereby attenuating contact hypersensitivity.

10 Claims, 22 Drawing Sheets
(22 of 22 Drawing Sheet(s) Filed in Color)

(56) References Cited

OTHER PUBLICATIONS

Covas et al. 2008. Multipotent Mesenchymal Stromal Cells Obtained From Diverse Human Tissues Share Functional Properties and Gene-Expression Profile with CD146+ Perivascular Cells and Fibroblasts. Experimental Hematology, vol. 36, pp. 642-654.
Cui et al. 2007. Expanded Adipose-Derived Stem Cells Suppress Mixed Lymphocyte Reaction by Secretion of Prostaglandin E2. Tissue Engineering, vol. 13, No. 6, pp. 1185-1195.
Delarosa et al. 2009. Requirement of IFN-gamma-Mediated Indoleamine 2,3-Dioxygenase Expression in the Modulation of Lymphocyte Proliferation by Human Adipose-Derived Stem Cells. Tissue Engineering, Part A, vol. 15, No. 10, pp. 2795-2806.
Di Nicola et al. Human Bone Marrow Stromal Cells Suppress T-Lynphocyte Proliferation Induced by Cellular or Nonspecific Mitogenic Stimuli. Blood, vol. 99, No. 10, May 15, 2002, pp. 3838-3843.
Fernandes et al. 2004. A Dermal Niche for Multipotent Adult Skin-Derived Precursor Cells. Nature Cell Biology, vol. 6, pp. 1082-1093, supplement pp. 1-, and erratum published May 2005, p. 631. Published online Nov. 2004.
Friedenstein et al. 1970. The Development of Fibroblast Colonies in Monolayer Cultures of Guinea-Pig Bone Marrow and Spleen Cells. Cell Tissue Kinet., vol. 3, pp. 393-403.
Gang et al. 2007. SSEA-4 Identifies Mesenchymal Stem Cells From Bone Marrow. Blood, vol. 109, pp. 1743-1751.
Gonzalez et al. 2009. Adipose-Derived Mesenchymal Stem Cells Alleviate Experimental Colitis by Inhibiting Inflammatory and Autoimmune Responses. Gastroenterology, vol. 136, pp. 978-989.
Gonzalez et al. 2009. Adipose-Derived Mesenchymal Stem Cells Alleviate Experimental Colitis by Inhibiting Inflammatory and Autoimmune Responses. Gastroenterology, vol. 136, Supplementary pp. 1-12.
Gonzalez et al. 2009. Treatment of Experimental Arthritis by Inducting Immune Tolerance With Human Adipose-Derived Mesenchymal Stem Cells. Arthritis & Rheymatism, vol. 60, No. 4, Apr. 2009, pp. 1006-1019.
Gonzalez-Rey et al. 2009. Human Adult Stem Cells Derived From Adipose Tissue Protect Against Experimental Colitis and Sepsis. Gut, vol. 58, Jan. 9, 2009, pp. 929-939.
Gonzalez-Rey et al. 2009. Human Adult Stem Cells Derived From Adipose Tissue Protect Against Experimental Colitis and Sepsis. Gut, vol. 58, Jan. 9, 2009, Supplementary pp. 1-9.
Greco et al. 2007. Functional Similarities Among Genes Regulated by Oct4 in Human Mesenchymal and Embryonic Stem Cells. Stem Cells, vol. 25, pp. 3143-3154.
Gregory et al. 2004. An Alizarin Red-Based Assay of Mineralization by Adherent Cells in Culture: Comparison with Cetylpyridinium Chloride Extraction. Analytical Biochemistry, vol. 329, pp. 77-84.
Gronthos et al. 2000. Postnatal Human Dental Pulp Stem Cells (DPSCs) In Vitro and In Vivo. Proceedings of the National Academy of Sciences, vol. 97, No. 25, Dec. 5, 2000, pp. 13625-13630.
Gronthos et al. 2002. Stem Cell Properties of Human Dental Pulp Stem Cells. Journal of Dental Research, vol. 8, No. 8, Aug. 2002, pp. 531-535.
Haniffa et al. 2007. Adult Human Fibroblasts Are Potent Immunoregulatory Cells and Functionally Equivalent to Mesenchymal Stem Cells. The Journal of Immunology, vol. 179, pp. 1595-1604.
Haniffa et al. 2009. Mesenchymal Stem Cells: The Fibroblasts' New Clothes? Haematologica, vol. 94, pp. 258-263.
Int'anker et al. 2003. Amniotic Fluid as a Novel Source of Mesenchymal Stem Cells for Therapeutic Transplantation (Letter to the Editor). Blood, vol. 102, No. 4, Aug. 15, 2003, pp. 1548-1549.
Irwin et al. 1994 Inter- and Intra-Site Heterogeneity in the Expression of Fetal-Like Phenotypic Characteristics by Gingival Fibroblasts: Potential Significance for Wound Healing. Journal of Cell Science, vol. 107, pp. 1333-1346.
Iyer et al. 2008. Anti-Inflammatory Effects of Mesenchymal Stem Cells: Novel Concept for Future Therapies. Expert Opin. Biol. Ther., vol. 8, No. 5, pp. 569-581.
Jo et al. 2007. Isolation and Characterization of Postnatal Stem Cells from Human Dental Tissues. Tissue Engineering, vol. 13, No. 4, pp. 767-773.
Jones et al. 1993. Separation of Human Epidermal Stem Cells from Transit Amplifying Cells on the Basis of Differences in Integrin Function and Expression. Cell, vol. 73, May 21, 1993, pp. 713-724.
Karp et al. 2009. Mesenchymal Stem Cell Homing: The Devil Is in the Details. Cell Stem Cell, vol. 4, Mar. 6, 2009, pp. 206-216.
Khalil et al. 2006. Nonmyeloablative Stem Cell Therapy Enhances Microcirculation and Tissue Regeneration in Murine Inflammatory Bowel Disease. Gastroenterology, vol. 132, pp. 944-954.
Kim et al. 2007. Systemic Transplantation of Human Adipose Stem Cells Attenuated Cerebral Inflammation and Degeneration in a Hemorrhagic Stroke Model. Brain Research, vol. 1183, pp. 43-50.
Krampera et al. 2006. Role for Interferon-gamma in the Immunomodulatory Activity of Human Bone Marrow Mesenchymal Stem Cells. Stem Cells, No. 24, pp. 386-398.
Le Blanc et al. 2004. Treatment of Severe Acute Graft-Versus-Host Disease with Third Party Haploidentical Mesenchymal Stem Cells. Lancet, vol. 363, May 1, 2004, pp. 1439-1441.
Lee et al. 2006. Multipotent Stromal Cells From Human Marrow Home to and Promote Repair of Pancreatic Islets and Renal Glomeruli in Diabetic NOD/scid Mice. Proceedings of the National Academy of Sciences, vol. 103, No. 46, Nov. 14, 2006, pp. 17438-17443.
Lindroos et al. 2008. Characterisation of Human Dental Stem Cells and Buccal Mucosa Fibroblasts. Biochemical and Biophysical Research Communications, vol. 368, pp. 329-335.
Liu et al. 2008. Periodontal Ligament Stem Cell-Mediated Treatment for Periodontitis in Miniature Swine. Stem Cells, No. 26, pp. 1065-1073.
Lorenz et al. 2008. Multilineage Differentiation Potential of Human Dermal Skin-Derived Fibroblasts. Experimental Dermatology, vol. 17, pp. 925-932.
Lysy et al. 2007. Human Skin Fibroblasts: From Mesodermal to Hepatocyte-Like Differentiation. Hepatology, vol. 46, pp. 1574-1585.
Mahanonda et al. 2007. IL-8 and IDO Expression by Human Gingival Fibroblasts via TLRs. The Journal of Immunology, vol. 178, pp. 1151-1157.
Miura et al. 2003. SHED: Stem Cells from Human Exfoliated Deciduous Teeth. Proceedings of the National Academy of Sciences, vol. 100, No. 10, May 13, 2003, pp. S807-S812.
Mizoguchi et al. 2008. Inflammatory Bowel Disease, Past, Present and Future: Lessons from Animal Models. Journal of Gastroenterology, vol. 43, pp. 1-17.
Morsczeck et al. 2005. Isolation of Precursor Cells (PCs) From Human Dental Follicle of Wisdom Teeth. Matrix Biology, vol. 24, pp. 155-165.
Morsczeck et al. 2008. Somatic Stem Cells for Regenerative Dentistry. Clin. Oral Invest., vol. 12, pp. 113-118.
Muraglia et al. 2000. Clonal Mesenchymal Progenitors from Human Bone Marrow Differentiate In Vitro According to a Hierarchical Model. Journal of Cell Science, vol. 111, pp. 1161-1166.
Nauta et al. 2007. Immunomodulatory Properties of Mesenchymal Stromal Cells. Blood 2007, vol. 110, pp. 3499-3506.
Nemeth et al. 2009. Bone Marrow Stromal Cells Attenuate Sepsis Via Prostaglandin E2-Dependent Reprogramming of Host Macrophages to Increase Their Interleukin-10 Production. Nature Medicine, vol. 15, No. 1, Jan. 2009, pp. 42-49 (and subsequent Corrigendum).
Novak et al. 2008. The Immune Privilege of the Oral Mucosa. Trends in Molecular Medicine, vol. 14, No. 5, pp. 191-198.
Oh et al. 2008. Immunological Properties of Umbilical Cord Blood-Derived Mesenchymal Stromal Cells. Cellular Immunology, vol. 251, pp. 116-123.
Parekkadan et al. 2008. Bone Marrow-Derived Mesenchymal Stem Cells Ameliorate Autoimmune Enteropathy Independently of Regulatory T Cells. Stem Cells, No. 26, pp. 1913-1919.
Pittenger et al. 1999. Multilineage Potential of Adult Human Mesenchymal Stem Cells. Science, New Series, vol. 284, No. 5411, Apr. 2, 1999, pp. 143-147.

(56) References Cited

OTHER PUBLICATIONS

Podolsky, D.K. 2002. Inflammatory Bowel Disease: Review Article. New England Journal of Medicine, vol. 347, No. 6, Aug. 8, 2002, pp. 417-429.

Polchert et al. 2008. IFN-gamma Activation of Mesenchymal Stem Cells for Treatment and Prevention of Graft Versus Host Disease. European Journal of Immunology, vol. 38, pp. 1745-1755.

Prockop et al. 1997. Marrow Stromal Cells as Stem Cells for Nonhematopoietic Tissues. Science, New Series, vol. 276, No. 5309, Apr. 4, 1997, pp. 71-74.

Ryan et al. 2007. Interferon-gamma Does Not Break, But Promotes the Immunosuppressive Capacity of Adult Human Mesenchymal Stem Cells. Clinical and Experimental Immunology, vol. 149, pp. 353-363.

Sato et al. 2007. Nitric Oxide Plays a Critical Role in Suppression of T-Cell Proliferation by Mesenchymal Stem Cells. Blood, vol. 109, pp. 228-234.

Selmani et al. 2008. Human Leukocyte Antigen-G5 Secretion by Human Mesenchymal Stem Cells Is Required to Suppress T Lymphocyte and Natural Killer Function and to Induce CD4+CD25highFoxP3+ Regulatory T Cells. Stem Cells, No. 26, pp. 212-222.

Seo et al. 2004. Investigation of Multipotent Postnatal Stem Cells From Human Periodontal Ligament. Lancet, vol. 364, Jul. 10, 2004, pp. 149-155.

Sheng et al. 2008. A Critical Role of IFNgamma in Priming MSC-Mediated Suppression of T Cell Proliferation Through Up-Regulation of B7-H1. Cell Research, vol. 18, pp. 846-857.

Shi et al. 2002. Bone Formation by Human Postnatal Bone Marrow Stromal Cells is Enhanced by Telomerase Expression. Nature Biotechnology, vol. 20, Jun. 2002, pp. 587-591.

Spaeth et al. 2008. Inflammation and Tumor Microenvironments: Defining the Migratory Itinerary of Mesenchymal Stem Cells. Gene Therapy, vol. 15, pp. 730-738.

Spaggiari et al. 2008. Mesenchymal Stem Cells Inhibit Natural Killer-Cell Proliferation, Cytotoxicity, and Cytokine Production: Role of Indoleamine 2,3-Dioxygenase and Psotaglandin E2. Blood, vol. 111, pp. 1327-1333.

Stephens et al. 2001. Skin and Oral Fibroblasts Exhibit Phenotypic Differences in Extracellular Matrix Reorganization and Matrix Metalloproteinase Activity. British Journal of Dermatology, vol. 144, pp. 229-237.

Sudo et al. 2007. Mesenchymal Progenitors Able to Differentiate Into Osteogenic, Chondrogenic, and/or Adipogenic Cells In Vitro Are Present in Most Primary Fibroblast-Like Cell Populations. Stem Cells, No. 25, pp. 1610-1617.

Tanaka et al. 2008. Exogenous Administration of Mesenchymal Stem Cells Ameliorates Dextran Sulfate Sodium-Induced Colitis Via Anti-Inflammatory Action in Damaged Tissue in Rats. Journal of Life Sciences, vol. 83, pp. 771-779.

Tao et al. 2005. Cytokine-Induced Stable Neuronal Differentiation of Human Bone Marrow Mesenchymal Stem Cells in a Serum/Feeder Cell-Free Condition. Develop. Growth Differ., vol. 47, pp. 423-433.

Toma et al. 2005. Isolation and Characterization of Multipotent Skin-Derived Precursors from Human Skin. Stem Cells, No. 23, pp. 727-737.

Uccelli et al. 2008. Mesenchymal Stem Cells in Health and Disease. Nature, vol. 8, Sep. 2008, pp. 726-736.

Wada et al. 2009. Immunomodulatory Properties of Human Periodontal Ligament Stem Cells. J. Cell. Physiol., vol. 219, pp. 667-676.

Wang et al. The Immunomodulatory Activity of Human Umbilical Cord Blood-Derived Mesenchymal Stem Cells In Vitro. 2008. Immunology, vol. 126, pp. 220-232.

Xavier et al. 2007. Unravelling the Pathogenesis of Inflammatory Bowel Disease. Nature, vol. 448, Jul. 26, 2007, pp. 427-434.

Yamaza et al. 2008. Pharmacologic Stem Cell Based Intervention as a New Approach to Osteoporosis Treatment in Rodents. PLoS One, vol. 3, No. 7, Jul. 2008, e2615, pp. 1-9.

You et al. 2004. Cellular Characteristics of Primary and Immortal Canine Embryonic Fibroblast Cells. Experimental and Molecular Medicine, vol. 36, No. 4, Aug. 2004, pp. 325-335.

Yu et al. 2008. Critical Role of Phosphoinositide 3-Kinase Cascade in Adipogenesis of Human Mesenchymal Stem Cells. Mol. Cell Biochem., vol. 310, pp. 11-18.

Zhang et al. 2005. Human Bone Marrow Stromal Cell Treatment Improves Neurological Functional Recovery in EAE Mice. Experimental Neurology, vol. 195, pp. 16-26.

Zhou et al. 2008. Transplantation of Human Bone Marrow Mesenchymal Stem Cell Ameliorates the Autoimmune Pathogenesis in MRL/lpr Mice. Cellular & Molecular Immunology, vol. 5, No. 6, pp. 417-424.

USPTO. 2016. Non-final Office Action, dated Mar. 25, 2016, for U.S. Appl. No. 13/145,541, filed Feb. 1, 2012, entitled "Gingiva Derived Stem Cell and Its Application in Immunodulation and Reconstruction," published May 24, 2012, as U.S. Publication No. 2012-0128636 A1.

Lanzoni et al., World Journal of Gastroenterology, Aug. 7, 2008, vol. 14, No. 29, pp. 4616-4626.

Final Office Action from U.S. Appl. No. 13/145,541, dated Jan. 26, 2017.

\* cited by examiner

METHODS OF PROMOTING WOUND HEALING AND ATTENUATING CONTACT HYPERSENSITIVITY WITH GINGIVA-DERIVED MESENCHYMAL STEM CELLS

CROSS-REFERENCE TO RELATED APPLICATIONS

This application claims the benefit of U.S. Provisional Application No. 61/364,339, filed Jul. 14, 2010, the entire contents of which are incorporated herein by reference in its entirety.

STATEMENT REGARDING FEDERALLY SPONSORED RESEARCH OR DEVELOPMENT

This invention was made with government support under Contract Nos. CA82422, R01 DE 019932 awarded by the National Institutes of Health. The government has certain rights in the invention.

FIELD OF THE INVENTION

The invention pertains to the field of stem cell therapy. One aspect of the invention pertains to the use of human gingiva-derived mesenchymal stem cells to enhance cutaneous wound healing via their immunomodulatory effects on the innate immune cells, specifically driving the polarization of M2 macrophages.

BACKGROUND OF THE INVENTION

Cutaneous wound healing represents a highly coordinated process to achieve tissue homeostasis, which involves complex interactions of different types of resident cells and infiltrating immune cells as well as their secreted soluble mediators [23]. The repair process involves three distinct but overlapping phases: inflammation, tissue formation, and remodeling [23]. Upon tissue insult, the immediate inflammatory response is characterized by infiltration and activation of leukocytes, whereas a delayed or excessive inflammatory response may lead to abnormal wound healing in diabetic patients, scarring and fibrotic diseases. Aside from leukocytes which act as the principal cellular component of the early inflammatory response, macrophages contribute to all stages of wound repair [23-25]. Particularly, several studies have shown that M2 macrophages can produce mediators essential in the resolution of inflammation and tissue modeling, thus promoting wound repair [26, 27]. Recent studies have demonstrated that systemically injected MSCs can home to injury sites [28-30], differentiate into multiple types of skin cells [30, 31] and secrete various factors with proliferative, anti-inflammatory, angiogenic or chemotactic effects [30, 31], thus facilitating survival/proliferation of both resident and replacing cells, and consequently accelerating wound repair [31]. Although the role of macrophages [23-25] and MSCs [24, 28, 29] have been implicated in wound repair, little is known about their interactions, specifically whether MSCs can promote the transition of M1 to M2 macrophage in accelerating the healing of skin wounds.

Allergic contact dermatitis (ACD) is one of the most prevalent skin diseases worldwide with significant economic burden. Clinically, ACD is the manifestation of delayed-type contact hypersensitivity (CHS) in response to small-molecular, highly reactive contact allergens (haptens), and is characterized by redness, papules and vesicles, followed by scaling and dry skin at the contact local site (62, 63). The hapten-induced murine contact hypersensitivity (CHS) is widely used as a model for human ACD. Comparable to the pathophysiology of human ACD, the murine CHS model comprises three phases: the sensitization phase (also termed as the afferent or induction phase), the elicitation or challenge phase, and the resolution/regulation phase (62). The sensitization phase is initiated immediately after the first exposure of skin to haptens, followed by the uptake and process of haptens or haptenated proteins by the cutaneous antigen-presenting cells, particularly, the dendritic cells (DCs) (62). The haptenized or activated DCs migrate from skin to regional draining lymphnodes (dLNs) where they are responsible for the priming of allergen-specific T lymphocytes, including $CD8^+$ cytotoxic and $CD4^+$ T helper cells. Afterwards, the primed T cells re-circulate between lymphoid organs and skin (14). The elicitation phase occurs at the encounter of the same hapten, resulting in recruitment of blood leukocytes, amplified activation of allergen-specific effector $CD8^+$ and $CD4^+$ T cells, as well as activation of innate immune cells, particularly, mast cells. The activation of several subtypes of immune cells leads to enhanced production of an array of inflammatory cytokines and mediators that contribute to the appearance of eczematous lesions within 24-48 hours. The resolution/regulation phase occurs following the clearance of haptens from the skin contact site and the recruitment and activation of $CD4^+$ Tregs and other potential regulatory immune cells, which subsequently leads to the resolution of all inflammatory processes (62). Currently, topical application of corticosteroid is the first-line palliative measure for ACD with short-term outcome, while allergen identification to improve contact avoidance is still challenging. Therefore, there is an urgent need to develop a more effective, curative desensitizing tool based on specific cellular targets engaged by f multiple types of innate and adaptive immune cells in the complex but distinctively phased pathophysiological processes of ACD.

SUMMARY OF THE INVENTION

Recently, a unique population of isolated mesenchymal stem cells (MSCs) derived from human gingival tissue has been identified and isolated and termed gingival-derived mesenchymal stem cells (GMSCs). GMSCs are characterized by their ease of isolation, accessible tissue source, and rapid ex vivo expansion. GMSCs have stem cell-like properties and immunosuppressive and anti-inflammatory functions.

One aspect of the present invention is the discovery that GMSCs can reprogram macrophages toward an anti-inflammatory M2 phenotype. As shown herein, when co-cultured with GMSCs, macrophages acquire an anti-inflammatory M2 phenotype characterized by an increased expression of mannose receptor (MR/CD206) and secretory cytokines IL-10 and IL-6, a suppressed production of TNF-α, and decreased ability to induce Th-17 cell expansion. One aspect of the present invention comprises a method of polarizing macrophages to exhibit M2 phenotype, comprising introducing an effective amount of gingiva-derived mesenchymal stem cells to an environment comprising a population of macrophages such that the macrophages are in fluid communication with the gingiva-derived mesenchymal stem cells. As a result of being in fluid communication, said macrophages exhibit by at least one of an increased expression of mannose receptor (MR/CD206), increased expression of IL-10 and IL-6, a suppressed production of TNF-α, and decreased ability to induce Th-17 cell expansion relative to a similar population of untreated macrophages. Preferably, the macrophages are characterized at least by a suppressed production of TNF-α.

Another aspect of the present invention is the discovery that treatment with the isolated GMSC's in vivo results in improved skin wound healing characterized by rapid re-epithelialization, improved angiogenesis and improved tissue remodeling. In vivo, systemically infused isolated GMSCs, when used in accordance with the present invention, home to the wound sites, promote macrophages toward M2 polarization, and significantly enhance wound repair. Without being limited to theory, GMSC treatment mitigated local inflammation mediated by a suppressed infiltration of inflammatory cells and production of IL-6 and TNF-α, and an increased expression of IL-10. The GMSC-induced suppression of TNF-α secretion by macrophages appears to correlate with impaired activation of NFκB p50. Another embodiment of the present invention is a method of promoting cutaneous wound healing comprising administering to a patient an effective amount of human gingiva-derived mesenchymal stem cells, thereby resulting in at least one of accelerated wound closure, rapid re-epithelialization, improved angiogenesis and improved tissue remodeling relative to untreated controls.

Another aspect of the present invention is the discovery that systemic application of GMSCs significantly suppresses both the sensitization and elicitation of contact hypersensitivity (CHS) through modulating the function of multiple types of innate and adaptive immune cells through the COXs/PGE$_2$ pathway. Another embodiment of the present invention is directed to methods for suppressing or limiting CHS by administration to a patient human gingiva-derived mesenchymal stem cells (GMSCs). A method for attenuating contact hypersensitivity comprises administering to a patient an effective amount of human gingiva-derived mesenchymal stem cells at a time at least timeframe selected from the group consisting of before sensitization, after sensitization and before challenge and after challenge, thereby attenuating contact hypersensitivity.

More specifically, as described herein, administration by systemic infusion of GMSCs, preferably prior to the sensitization and challenge phase suppresses CHS, manifested as at least one of decreased infiltration of dendritic cells (DCs), CD8$^+$ T cells, T$_H$-17 and mast cells (MCs) and production of inflammatory cytokines, and a reciprocal increased infiltration of Tregs and expression of IL-10 in regional LNs and allergic contact areas. The GMSC-mediated immunosuppressive effects and mitigation of CHS were abrogated when GMSCs were pretreated with indomethacin, an inhibitor of cyclo-oxygenases (COXs). Without being limited to theory, in vitro studies revealed that GMSC-induced suppression of de novo synthesis of pro-inflammatory cytokines by mast cells are mediated partly by the TNF-α/PGE$_2$ feedback axis.

The present invention further includes a pharmaceutical composition comprising an effective amount human gingiva-derived mesenchymal stem cells in a carrier medium. The pharmaceutical compositions of the present invention are used for administration of the human gingiva-derived mesenchymal stem cells for treatment in accordance with any of the methods described herein.

BRIEF DESCRIPTION OF THE FIGURES

"The file of this patent contains at least one drawing executed in color. Copies of this patent with color drawings will be provided by the Office upon request and payment of the necessary fee".

DETAILED DESCRIPTION OF THE INVENTION

Figure 1:
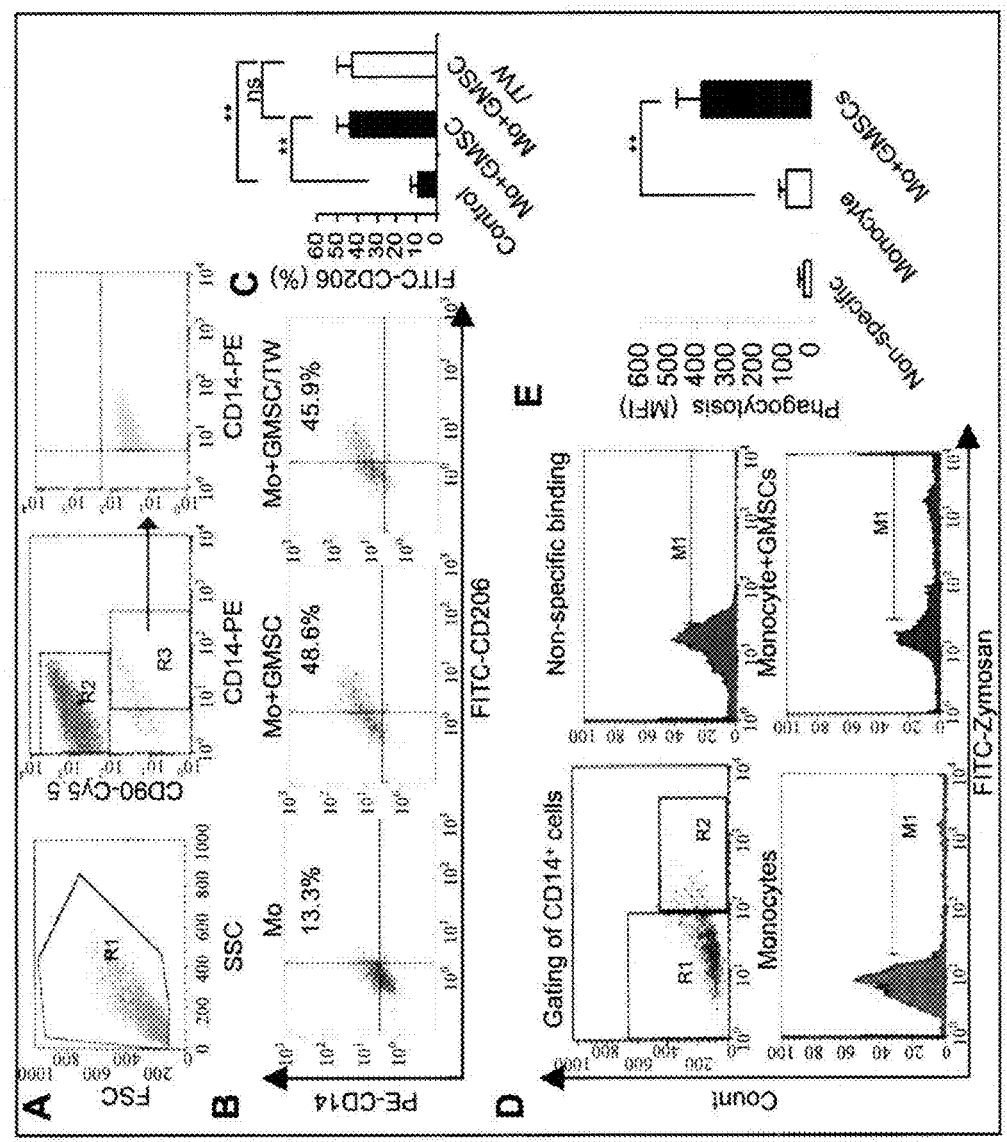
FIG. 1 shows that GMSCs promote the polarization of M2 macrophages. Monocytes isolated from PBMCs using human monocyte isolation kit were seeded in 6-well plates (2×10$^5$/well) and cultured in macrophage growth medium for 7 days, followed by co-culture with the same number of GMSCs for 3 days. Co-cultured cells were collected and immunostained with PerCp/Cy5.5-CD90, PE-CD14 and FITC-CD206 and analyzed by flow cytometry. (A): Strategy of gating CD14 positive cells from the co-culture with GMSCs (CD90-PerCp/Cy5.5). (B, C): Comparison of CD206 expression on macrophages cultured alone (Control) and cocultured in direct contact with GMSCs or in a transwell system (GMSCs/TW). (D): After coculture with GMSCs in the transwell for 72 h, macrophages were incubated with 25 µg/mL FITC-Zymosan for 1 h at 4° C. (non-specific binding) and 37° C., respectively, and analyzed by flow cytometry. Macrophages cultured alone were used as controls. (E): The average mean fluorescence intensity (MFI) of phagocytosed particles is shown for three different cultures. The results represent three independent experiments (mean±SEM). **$P<0.01$; ns, no significance.

Recently, a unique population of mesenchymal stem cells (MSCs) derived from human gingival tissue has been identified and isolated and termed gingiva-derived mesenchymal stem cells (GMSCs). GMSCs are characterized by their ease of isolation, accessible tissue source, and rapid ex vivo expansion. GMSCs have stem cell-like properties and immunosuppressive and anti-inflammatory functions. The pharmaceutical compositions of the present invention comprise isolated GMSCs, and the methods of the present invention generally include administration of the isolated GMSCs. The isolated GMSCs useable in connection with the compositions and methods of the present invention are described in PCT Application No. PCT/US2010/021531, entitled "Gingiva Derived Stem Cell and its Applicaion in Immunomodulation and Reconstruction," and in Zhang Q, Shi S, Liu Y et al., *Mesenchymal stem cells derived from human gingiva are capable of immunomodulatory functions and ameliorate inflammation-related tissue destruction in experimental colitis*, J Immunol 2009; 183: 7787-7798, the entire contents of both of which are incorporated by reference. It should be noted that the term isolated GMSCs should be interpreted to mean GMSCs isolated from gingival tissues as set forth and described Application PCT/US2010/021531, and the term does not preclude admixture with other ingredients in, for example, clinical use as part of a pharmaceutical formulation or administration to a patient.

One aspect of the present invention comprises a method of polarizing macrophages to exhibit M2 phenotype, introducing an effective amount of gingiva-derived mesenchymal stem cells to an environment comprising a population of macrophages such that the macrophages are in fluid communication with the gingiva-derived mesenchymal stem cells. As a result of being in fluid communication, said macrophages exhibit at least one of an increased expression of mannose receptor (MR/CD206), increased expression of IL-10 and IL-6, a suppressed production of TNF-α, and decreased ability to induce Th-17 cell expansion relative to a similar population of untreated macrophages. Preferably, the macrophages are characterized at least by a suppressed production of TNF-α. As shown herein, when co-cultured with GMSCs, macrophages acquire an anti-inflammatory M2 phenotype characterized by an increased expression of mannose receptor (MR/CD206) and secretory cytokines IL-10 and IL-6, a suppressed production of TNF-α, and decreased ability to induce Th-17 cell expansion. The GMSCs are preferably administered in the form of a pharmaceutical composition comprising the GMSCs.

As used herein, the term an "effective amount" of GMSCs, when used in connection with a method, is an amount of the GMSCs sufficient to carry out a specifically stated purpose. In general, an "effective amount" may be determined empirically by reference to the data and standards disclosed herein and in a routine manner in relation to the stated purpose. An effective amount is preferably given in a single dose to the patient; however, the effective amount may be delivered to the patient as a number of doses over a period of time.

In connection with a method of polarizing macrophages to exhibit M2 phenotype, an effective amount of gingiva-derived mesenchymal stem cells is an amount sufficient, once administered, to polarize the macrophages such that they exhibit at least one of an increased expression of mannose receptor (MR/CD206), increased expression of IL-10 and IL-6, a suppressed production of TNF-α, and decreased ability to induce Th-17 cell expansion relative to a similar population of untreated macrophages. An effective amount for increasing expression may be confirmed by comparing PBMC-derived macrophages cultured alone versus PBMC derived macrophages co-culture with GMSCs. An effective amount of GMSCs to increase the mannose receptor is defined as the amount necessary to increase the percentage of macrophages expressing the mannose receptor in a GMSC co-culture as compared with macrophage cultured to at least greater than 10% and preferably greater than 40% (See FIG. 1A, 43.6±6.68% vs. 9.33±3.48%; $P<0.01$) (FIG. 1B, 1C). An effective amount may also be defined as the amount necessary to achieve about the significantly increased the percentage of macrophages expressing IL-10 (FIG. 2A) and IL-6 (FIG. 2B), while decreased TNF-α-positive macrophages (FIG. 2C) in comparison with macrophages cultured alone as described herein.

In connection with the present invention, the population of macrophages to be polarized into the M2 population are in fluid communication with the gingiva-derived mesenchymal stem cells. The population of macrophages may include but are not limited to PBMC-derived macrophages. The macrophages may be purified, or they may exist in vivo in the subject to be treated. It is not necessary that the GMSCs and macrophage population physically contact each other. As described herein, soluble factors play an important role in macrophage plasticity, and the M2 macrophage population can be induced by soluble factors secreted by mesenchymal stem cells. Rather, it is sufficient that the GMSCs be brought into sufficient proximity in a environment of suitably low viscosity that the induction may take place in a reasonable time. Generally, when administered to a subject, GMSCs may home to sites having a suitable environment for fluid communication between the GMSCs and the population of macrophages.

Another embodiment of the present invention is a method of promoting cutaneous wound healing comprising administering to a patient an effective amount of human gingiva-derived mesenchymal stem cells, thereby resulting in at least one of accelerated wound closure, rapid re-epithelialization, improved angiogenesis and improved tissue remodeling. As used herein, the term "patient" refers to any animal (e.g., a mammal), including, but not limited to, humans, non-human primates, rodents, and the like, which is to be the recipient of a particular treatment. Preferably, the patient is a human.

Accelerated wound closure, rapid re-epithelialization, improved angiogenesis and improved tissue remodeling may measured relative to an appropriately selected control population as for example described herein. As described herein, treatment with isolated GMSC's in vivo results in improved skin wound healing characterized by rapid re-epithelialization, improved angiogenesis and improved tissue remodeling. In one example, in vivo, systemically infused isolated GMSCs, when used in accordance with the present invention, home to the wound sites, promote macrophages toward M2 polarization, and significantly enhance wound repair. Without being limited to theory, GMSC treatment mitigates local inflammation mediated by a suppressed infiltration of inflammatory cells and production of IL-6 and TNF-α, and an increased expression of IL-10. The GMSC-induced suppression of TNF-α secretion by macrophages appears to correlate with impaired activation of NFκB p50.

The GMSCs are preferably administered in the form of a pharmaceutical composition comprising the GMSCs. Although a single administration of the GMSC's is preferred, the method of wound healing may include two or more administrations of the GMSC, including periodic re-administration of the GMSCs over a period of time.

The type of wound to be treated is not particularly limited. Generally, it can be any wound that that may be benefit from accelerated wound closure, rapid re-epithelialization, improved angiogenesis and improved tissue remodeling may measured relative to an appropriately selected control population as understood by clinicians. The wound may be in a substantially healthy patient or in a patient having a disease or disorder which may negatively affect wound healing.

Another aspect of the present invention is the discovery that systemic application of GMSCs significantly suppresses both the sensitization and elicitation of contact hypersensitivity (CHS) through modulating the function of multiple types of innate and adaptive immune cells through the COXs/PGE$_2$ pathway. Another embodiment of the present invention is directed to methods for suppressing or limiting CHS by administration of human gingiva-derived mesenchymal stem cells (GMSCs). A method for attenuating contact hypersensitivity comprises administering to a patient an effective amount of human gingiva-derived mesenchymal stem cells at a time at least timeframe selected from the group consisting of before sensitization, after sensitization and before challenge and after challenge, thereby attenuating contact hypersensitivity. Attenuating contact hypersensitivity should be understood as referring to both therapeutic treatment to lessen a hypersensitivity reaction in a patient and to prophylactic or preventative measures to lessen the risk for or onset of a contact hypersensitivity reaction. Patients include those already with the disorder as well as those prone to have the disorder or those in whom the disorder is to be prevented. The GMSCs are preferably administered in the form of a pharmaceutical composition comprising the GMSCs.

More specifically, as described herein, administration by systemic infusion of GMSCs, preferably prior to the sensitization and challenge phase suppresses CHS, manifested as at least one of decreased infiltration of dendritic cells (DCs), CD8$^+$ T cells, T$_H$-17 and mast cells (MCs) and production of inflammatory cytokines, and a reciprocal increased infiltration of Tregs and expression of IL-10 in regional LNs and allergic contact areas. The GMSC-mediated immunosuppressive effects and mitigation of CHS were abrogated when GMSCs were pretreated with indomethacin, an inhibitor of cyclo-oxygenases (COXs). Without being limited to theory, in vitro studies revealed that GMSC-induced suppression of de novo synthesis of pro-inflammatory cytokines by mast cells are mediated partly by the TNF-α/PGE$_2$ feedback axis.

The present invention further includes a pharmaceutical composition comprising an effective amount of pharmaceutical composition comprising isolated gingiva-derived mesenchymal stem cells in a carrier medium. The pharmaceutical compositions of the present invention are used for administration of the human gingiva-derived mesenchymal stem cells for treatment in accordance with any of the methods described herein.

In the methods described herein, the GMSCs should be compatible with the patient and be administered in a therapeutically effective amount of the GMSCs. The therapeutically effective amount can range from the maximum number of cells that is safely received by the patient to the minimum number of cells necessary for to achieve the intended effect. Generally, the therapeutically effective amount of the GMSCs in the in vivo studies described herein has been $2\times10^6$/mice which is equivalent to approximately $10^8$/kg body weight in human. One of ordinary skill in the art can extrapolate mouse data to humans or other species to a therapeutically effective amount of GMSCs per kg of body weight of the patient as well as optimize effective amounts according to known techniques to effectuate the intended purpose of the treatment.

The therapeutically effective amount of the GMSCs can be suspended in a pharmaceutically acceptable carrier or excipient. Such a carrier may include but is not limited to a suitable culture medium plus 1% serum albumin, saline, buffered saline, dextrose, water, and combinations thereof. The formulation should suit the mode of administration.

In a preferred embodiment, the GMSC preparation or composition is formulated for systemic administration to human beings in accordance with procedures for pharmaceutical formulations knows to those of ordinary skill. Typically, compositions for systemic administration are solutions in sterile isotonic aqueous buffer. The ingredients may be supplied either separately or mixed together in unit dosage form, for example, as a cryopreserved concentrate in a hermetically sealed container such as an ampoule indicating the quantity of active agent.

A variety of means for administering cells to subjects will, in view of this specification, be apparent to those of skill in the art. Such methods include may include systemic administration or injection of the cells into a target site in a subject. Cells may be inserted into a delivery device which facilitates introduction by injection or implantation into the subjects. Such delivery devices may include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The cells may be prepared for delivery in a variety of different forms. For example, the cells may be suspended in a solution or gel. Cells may be mixed with a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid, and will often be isotonic. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like.

Modes of administration of the GMSCs include but are not limited to systemic intravenous or intra-arterial injection and injection directly into the tissue at the intended site of activity. The preparation can be administered by any convenient route, for example by infusion or bolus injection and can be administered together with other biologically active agents. Administration is preferably systemic. It may be advantageous, under certain conditions, to use a site of administration close to or nearest the intended site of activity. Without intending to be bound by mechanism, GMSCs will, when administered, migrate or home to the tissue in response to chemotactic factors produced due to the inflammation or injury. When the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Administration of the GMSCs may be done in combination with one or more further therapeutic agents including simultaneous (concurrent) and consecutive administration in any order.

Example I

Human Gingiva Derived Mesenchymal Stem Cells Elicit Polarization and M2 Macrophages and Treatment Therewith Enhances Cutaneous Wound Healing Macrophages, one of the major types of innate immune cells, can produce a plethora of mediators that play various functions in inflammation, immunity and wound healing [11, 14]. Upon recruitment to the injury sites macrophages encounter various signals that drive their differentiation toward distinct phenotypes [11, 14]. M1 macrophages are generally induced by Th1 cytokines such as IFN-γ or Toll-like receptor agonists like lipopolysaccharide (LPS) and play important roles in inflammation and pathogen clearance via secreting pro-inflammatory mediators, including nitric oxide (NO), TNF-α, and IL-1z [11, 14]. On the contrary, M2 macrophages can be induced in response to diverse non-inflammatory cues, including Th2-related cytokines such as IL-4 and IL-13, IL-10, transforming growth factor-β1 (TGF-β1), glucocorticoids and apoptotic cells [11, 14]. M2 macrophages are characterized by secretion of high levels of anti-inflammatory cytokines, IL-10 and TGF-β1, as well as by the expression of specific markers such as mannose receptor (MR/CD206), chitinase like secretory lectins (Yml) and Fizz1 (found in inflammatory zone 1, also known as RELM-α) [11, 14]. Accumulating evidence has shown that M2 macrophages are not only implicated in Th2-driven pathologies such as helminth infection and asthma [19], but also can coordinate adaptive immune responses by interacting with Tregs [36, 40], ameliorate the outcome of several inflammatory diseases by counteracting Th1-initiated inflammatory responses [17-19, 41], and contribute to tissue homeostasis by promoting inflammatory resolution [13].

In addition to IL-4 and IL-13, several other soluble factors, including IL-10 [39], GM-CSF [42-44], PGE$_2$ [15, 21], CCL-2 (MCP-1) and IL-6 [45], are also capable to induce polarization of M2 macrophages under different experimental settings. For instance, CCL2 and interleukin-6 can promote survival of human CD11b peripheral blood mononuclear cells and induce M2 macrophage polarization [45]. GM-CSF can skew mice macrophage progenitors toward an M2 phenotype, especially in the absence of SHIP [44]. Recent studies have shown that PGE$_2$ constitutively produced by MSCs might be responsible for MSC-induced M2 phenotype of macrophages [15, 21]. We observed a relatively abundant level of IL-6, CCL2, IL-10 and GM-CSF in co-cultured human macrophages and GMSCs (FIG. 4), wherein GMSCs promoted the switch of macrophages to an M2-like profile in a soluble factor-dependent manner (FIG. 1B, 1C). However, only specific blocking of IL-6 and GM-CSF inhibited the induction of M2-like macrophages (FIG. 5A, 5B), indicating that both IL-6 and GM-CSF could contribute to GMSC-induced polarization of M2 macrophages.

Cutaneous wound healing is a complex process of well-defined overlapping events [23], wherein macrophages play an essential role in the removal of infiltrated leukocytes and cellular debris at the wound sites [13, 25, 46]. The depletion or selective ablation of macrophages could be detrimental to wound healing due to the failure of clearance of dead and damaged cells [25, 46]. It is recognized that both M1 and M2 macrophages play a pivotal role in different stages of physiological wound repair [12, 13, 47]. M1 macrophages are abundant during the initial inflammatory response and produce a high amount of pro-inflammatory cytokines and reactive oxygen species (ROS), whereas M2 macrophages are predominated in the resolution phase and secrete mainly anti-inflammatory cytokines and exert a higher phagocytic activity. In a recent study looking at the gene expression profile at the early stage of wound repair whereas the inflammatory response is relatively dominant, a mixture of M1 activation gene transcripts such as IL-6 and Toll-like receptors and M2 activation gene transcripts such as IL-13 and arginase were detected at the wound sites. On the contrary, as wound repair proceeds without infection, and tissue remodeling gradually takes place, the profile of macrophage-related transcripts was predominantly M2 activation genes such as TGF-β1 and IL-1 receptor agonist [47]. Recently, a population of resolution-phase macrophages (rM) was described during the resolving phase of acute peritonitis, which possessed a unique hybrid phenotype of both M2 and M1 as they not only express CD206 and synthesize IL-10 and arginase 1 but also express other markers typical of M1 (ie iNOS) [13]. Similarly, a recent study has shown that wound macrophages on day 1 express more TNF-α and IL-6 but less TGF-β1 than those on day 7, supporting the notion that wound macrophages exhibit a complex phenotype, which not only require IL-4 or IL-13, but also include traits associated with both M1 and M2 activation and phenotypic changes as the wound matures [27]. Routley et al have reported that estrogen or progesterone can contribute toward M2 activation of macrophages to drive wound repair, angiogenesis, and remodeling [38]. Consistently, we show herein a dynamic increase in the number of M2 macrophages and the level of anti-inflammatory cytokine IL-10, and a decrease in the expression of M1-cytokines (TNF-α and IL-6) during the wound healing process. All together, these findings support the notion that both the presence and the activation/phenotype of macrophages within the wound are fundamental elements in guiding normal wound repair [38] and manipulating the differentiation of plastic macrophages toward an M2 macrophage phenotype would provide novel strategies to promote normal wound healing or aid in the resolution of impaired wound healing.

We demonstrate herein, for the first time to our knowledge, that human gingiva-derived mesenchymal stromal cells (GMSCs) can switch the differentiation and activation of in vitro cultured human macrophages into an M2-like phenotype characterized by an increased expression of MR/CD206 and phagocytic activity, a high ability to express IL-10 and IL-6, and a low ability to express TNF-α, a phenotype similar to that of human macrophages after cocultured with hBMSCs [20]. More importantly, using an established mouse model of skin wound healing, we showed that systemic administration of GMSCs attenuated local inflammatory responses, increased angiogenesis and ECM deposition, and consequently enhanced skin wound healing. The GMSC-mediated rapid cutaneous wound repair is associated with a dynamic increase in the number of M2 macrophages characterized by an increased expression of arginase-1 and RELM-α. GMSCs are thus effective in enhancing skin wound repair possibly through switching the activation of host macrophages to an anti-inflammatory M2 phenotype.

The following Examples are provided in order to demonstrate and further illustrate certain embodiments and aspects of the present invention and are not to be construed as limiting the scope thereof.

Example I.A

GMSCs Convert Macrophages into M2 Phenotype

Figure 19:
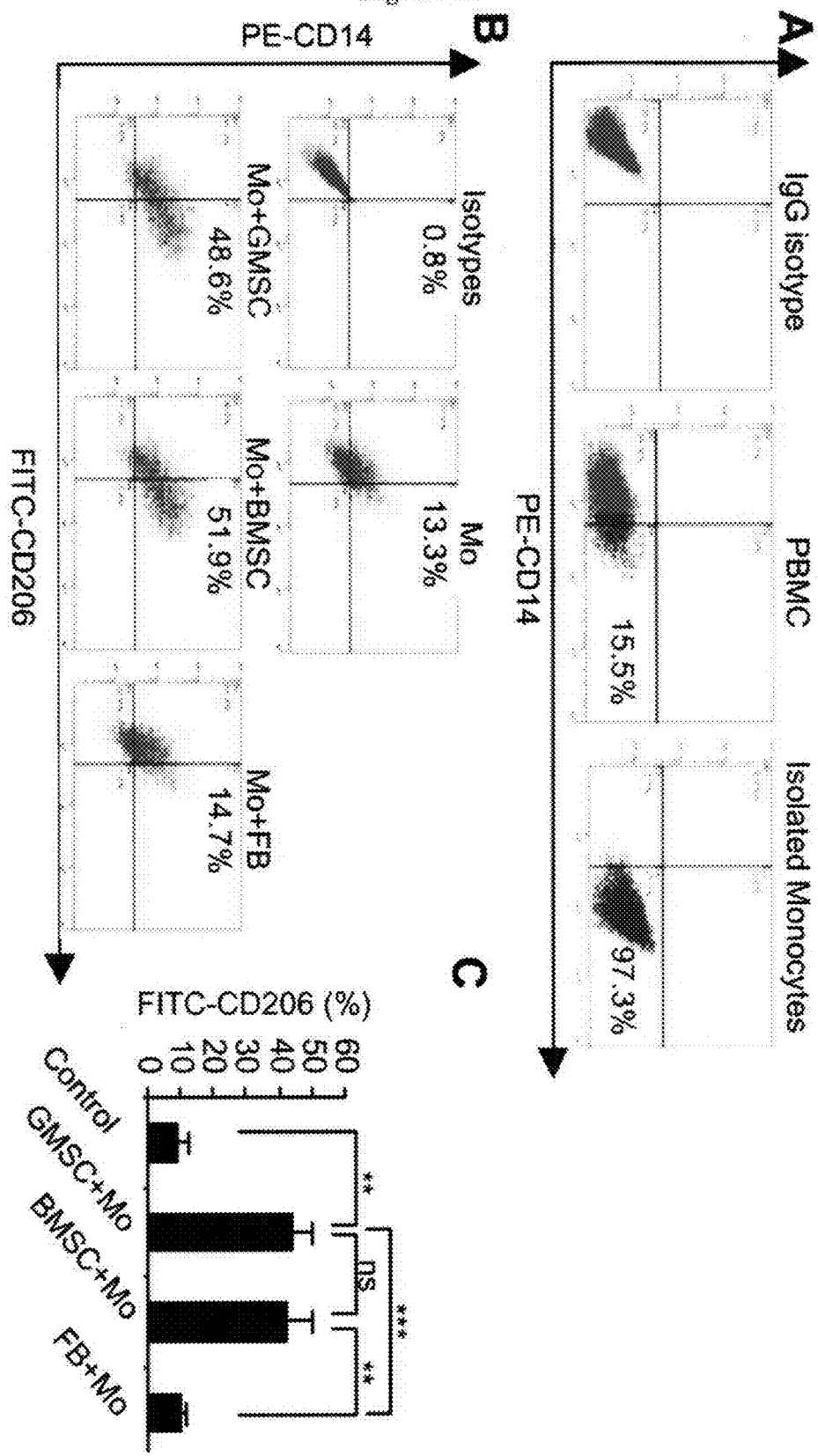
FIG. 19 shows a reproducible induction of $CD206^+$ macrophage population in co-culture with BMSCs (42.27±7.84%), whereas no obvious changes were detected in cultures with normal skin fibroblasts, or with macrophages alone (9.96±1.5% vs. 9.33±3.48%; P>0.05) (FIG. 19B, 19C). whereas no obvious changes were detected in cultures with normal skin fibroblasts, or with macrophages alone (9.96±1.5% vs. 9.33±3.48%; P>0.05) (FIG. 19B, 19C).

We have recently shown that GMSCs display similar immunomodulatory capacities to human BMSCs via interacting with T cells [32]. Herein, we further explore the potential interplay between GMSCs and macrophages and show that GMSCs can induce an anti-inflammatory M2 phenotype. To this end, human PBMC-derived macrophages were co-cultured with GMSCs at equal cell densities for 72 hours under direct cell-cell contact, and the expression of mannose receptor (MR/CD206), one of the well-accepted markers for M2 macrophage [11, 20, 36], was determined by flow cytometry. Our results showed that co-culture with GMSCs under direct cell-cell contact led to a significant increase in the expression of CD206 among CD14+ macrophages gated from the co-culture (FIG. 1A) as compared with macrophage cultured alone (43.6±6.68% vs. 9.33±3.48%; P<0.01) (FIG. 1B, 1C). To determine whether upregulation of CD206 induced by GMSCs is dependent on direct cell-cell contact and/or soluble factors, macrophages and GMSCs were co-cultured in the transwell system. Similarly, co-culture with GMSCs in transwells increased the CD206+ macrophage population to the same extent as under condition of direct cell-cell contact (42.27±7.84% vs. 43.6±6.68%; P>0.05) (FIG. 1B, 1C), indicating that soluble factors contributed an essential role in macrophage plasticity. To confirm that M2 macrophage population is specifically induced by soluble factors secreted by mesenchymal stem cells, we cultured macrophages with human BMSCs under the transwell condition. Similar with above findings, we observed a reproducible induction of CD206+ macrophage population in co-culture with BMSCs (42.27±7.84%), whereas no obvious changes were detected in cultures with normal skin fibroblasts, or with macrophages alone (9.96±1.5% vs. 9.33±3.48%; P>0.05) (FIG. 19B, 19C). Meanwhile, we observed about a 4-fold increase in the phagocytic activity in macrophages co-cultured with GMSCs in the transwell as compared to macrophages cultured alone (P<0.01) (FIG. 1D, 1E). The nonspecific adhesion of zymosan particles to macrophages after incubation at 4° C. was low to undetectable, indicating that the increased zymosan uptake in macrophages co-cultured with GMSCs was specifically caused by phagocytosis. These results confirmed that soluble factors released by co-cultured MSCs contribute to the polarization of macrophages to the M2 phenotype.

Example I.B

GMSCs Induce Anti-Inflammatory Immune Profile in Macrophages in Co-Culture

Figure 2:
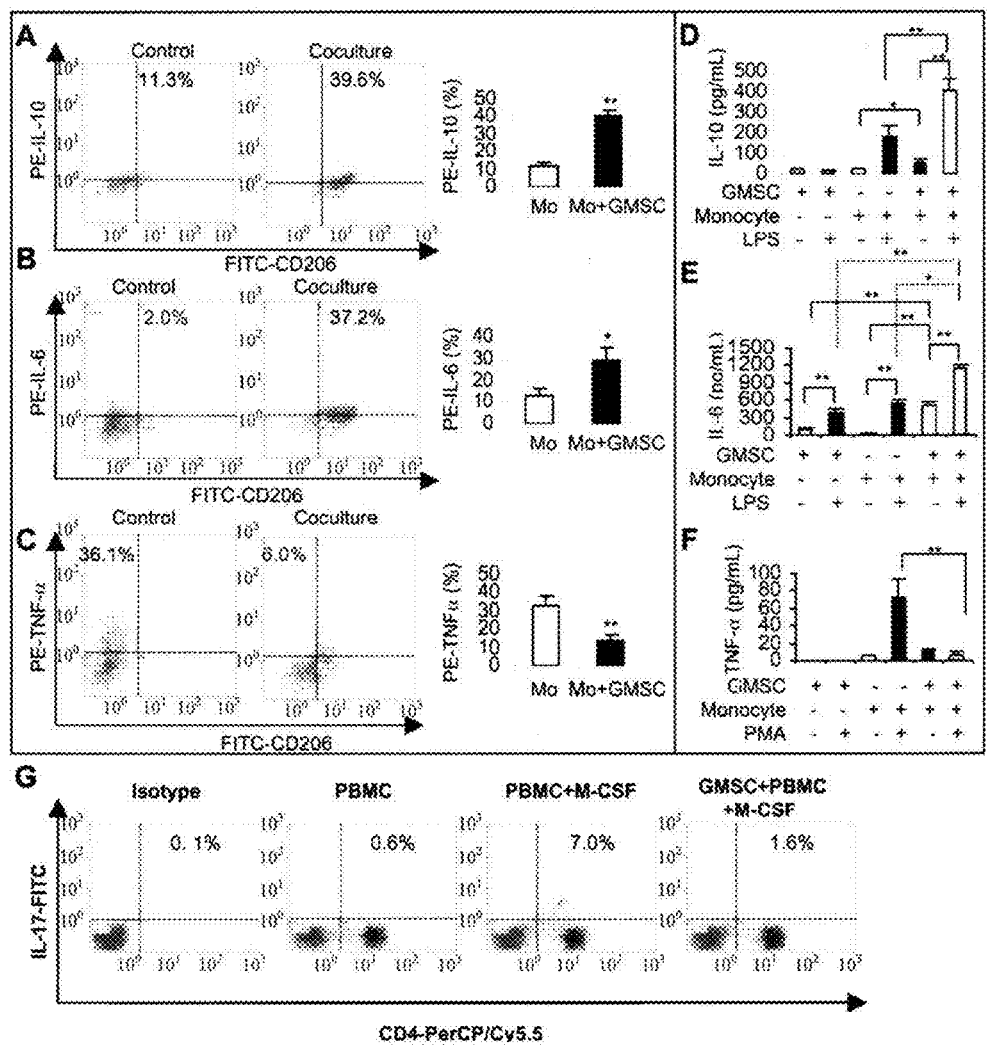
FIG. 2 shows that cytokine expression profiles in human macrophages cocultured with GMSCs. (A-C): After co-culture with GMSCs in the transwell for 72 h, macrophages were stained with FITC-CD206, followed by intracellular cytokine staining with PE-conjugated antibodies human IL-10 (A), IL-6 (B) and TNFα (C) and subjected to flow cytometry analysis, wherein cells stained with FITC- and PE-conjugated isotype control antibodies and macrophages cultured alone were used as controls. The graphs showed the average values from three independent experiments (mean±SEM). (D-F): The secretion of IL-10 (D), IL-6 (E), and TNFα (F) in the supernatants of co-cultured macrophages/GMSCs (2×10$^5$) was determined using ELISA as compared with GMSCs and macrophages cultured alone. (G): PBMCs (2×10$^5$) were cultured alone or co-cultured with the same number of GMSCs in the presence of M-CSF (30 ng/mL) for 72 h. Then PBMCs were collected and immunostained with isotype-matched IgGs, or CD4-PerCP/Cy5.5 and IL-17-FITC and analyzed by flow cytometry. PBMCs cultured alone in the absence of M-CSF were used as controls. The results represent three independent experiments (mean±SEM). *$P<0.05$; **$P<0.01$.

Next, we determined the cytokine expression profile by macrophages co-cultured with GMSCs. Flow cytometric analysis showed that, in comparison with macrophages cultured alone, co-culture with GMSCs significantly increased the percentage of macrophages expressing IL-10 (FIG. 2A) and IL-6 (FIG. 2B), while decreased TNF-α-positive macrophages (FIG. 2C) following stimulation using different protocols as previously described [20]. The differential cytokine profile of secretory IL-10, IL-6, and TNF-α in the supernatants of macrophages, GMSCs, and their co-cultures, was further confirmed by ELISA, respectively. Minimal release of cytokines was observed in macrophages or GMSCs alone in the absence of stimuli (FIG. 2D, 2F). Addition of stimulating agents triggered a burst of IL-10 and TNF-α secretion by macrophages, but had minimal effect on GMSCs cultured alone (FIG. 2D, 2F). The increased secretion of IL-10 triggered by LPS was significantly augmented in the co-culture of GMSCs and macrophages (FIG. 2D); on the contrary, in the same co-culture, PMA-triggered release of TNF-α was dramatically abolished (FIG. 2F). In addition, LPS also induced a marked increase in the production of IL-6 in the co-culture of GMSCs and macrophages as compared with macrophages and GMSCs alone (FIG. 2E). Most recently, it has been shown that the presence of macrophage-colony stimulating factor (M-CSF) in a co-culture system of peripheral blood monocytes and T lymphocytes could stimulate Th-17 cell expansion, possibly via M-CSF-induced macrophages [37]. Using this co-culture system we observed that GMSCs were capable of suppressing Th-17 cells expansion mediated by M-CSF-induced macrophages (FIG. 2G). Taken together, these results indicate that GMSCs are capable of switching macrophages from classical activation or pro-inflammatory M1 phenotype to an anti-inflammatory profile of M2 macrophages.

Example I.C

GMSCs Convert Inflammatory Human THP-1 Monocytes to M2 Macrophages

Figure 3:
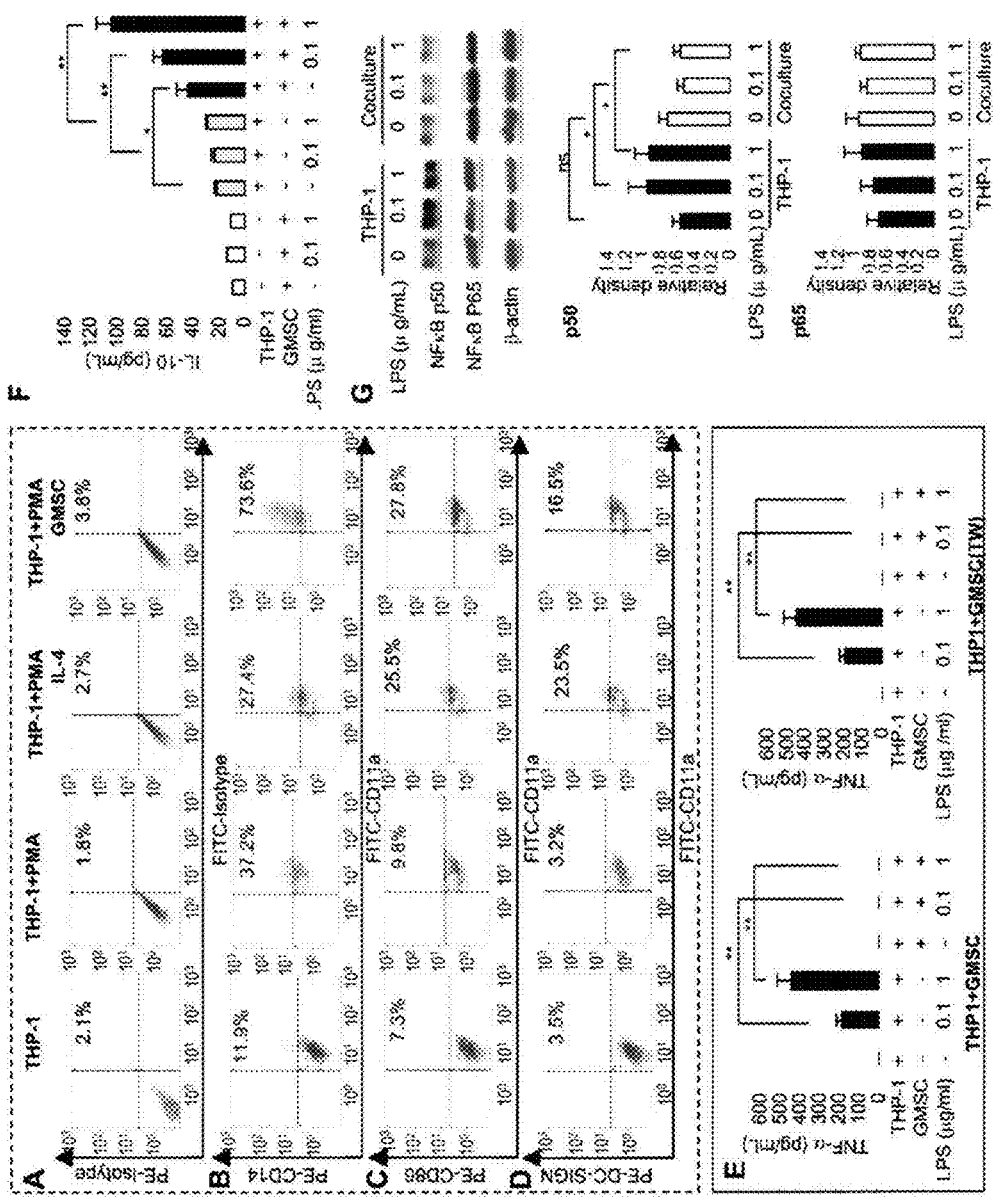
FIG. 3 shows that GMSCs regulate the immunophenotype and function of human monocyte leukemic cells (THP-1) during differentiation. (A-D): THP-1 cells (2×10$^5$) were differentiated upon stimulation with PMA (10 ng/mL) in the absence or presence of IL-4 (100 ng/mL) or coculture with GMSCs in the transwell for 96 h. Cells were stained with isotype-matched control IgGs (A), FITC-CD11a and PE-conjugated CD14 (B), CD86 (C) or DC-SIGN (D) antibodies (A) and then analyzed by flow cytometry. THP-1 cells without any treatment were used as controls. (E-F): After co-culture with GMSCs for 72 h, THP-1 cells were stimulated with 0.1 and 1 ug/mL LPS for 4 h (TNF-α) or 24 h (IL-10), and the secretion of TNF-α (E) and IL-10 (F) in the supernatants was determined by ELISA. (G): After co-culture with GMSCs for 72 h, THP-1 cells were stimulated with 0.1 and 1 µg/mL LPS for 1 h, and the expression of NFκB p50 and p65 were determined by Western blot, where the graphs represent the relative densities to the band of β-actin as the internal control. The results were representative of four independent experiments (mean±SEM). *$P<0.05$; **$P<0.01$.

THP-1, an established human monocyte leukemic cell line, has been widely used as a cellular model to dissect the molecular mechanisms underlying monocyte-macrophage or dendritic cell differentiation [33]. Previous studies have shown that during PMA-induced THP-1 differentiation, IL-4 or IL-13, two well-known inducers for polarization of M2 macrophages [11, 14], could enhance the expression of CD86 and dendritic cell-specific ICAM-3-grabbing nonintegrin (DC-SIGN, CD209), a marker for both immature dendritic cells and M2 macrophages [33]. To further explore the role of GMSC in the modulation of monocyte/macrophage differentiation, we co-cultured differentiating THP-1 cells with GMSCs in transwells. In agreement with a previous study [33], we showed that addition of IL-4 suppressed CD14 and significantly increased CD86 and DC-SIGN expression (FIG. 3A-3D). Interestingly, co-culture with GMSCs not only led to increased expression of CD86 and DC-SIGN but also markedly promoted CD14 expression during PMA-induced THP-1 differentiation (FIG. 3A-3D). In addition, our results indicated that LPS-stimulated increase in the secretion of TNF-α was almost abolished in THP-1 cells when co-cultured with GMSC in both direct cell-cell contact and the transwell systems (FIG. 3E). GMSCs cultured alone did not express constitutive nor inducible TNF-α expression in response to LPS stimulation (data not shown). On the contrary, stimulation of co-culture of THP-1 cells and GMSCs with LPS led to a concentration-dependent increase in secretory IL-10, whereas only a slight increase was observed in THP-1 or GMSCs cultured alone (FIG. 3F). At the mechanistic level, LPS stimulation failed to up-regulate NFκB p50 in THP-1 cells co-cultured with GMSCs as compared to THP-1 cells alone (FIG. 3G). The impaired LPS-induced activation of NFκB p50 appears to correlate with the suppression of pro-inflammatory cytokine TNF-α released by THP-1 cells in the presence of GMSCs. All together, these results indicate that GMSCs were capable to reprogram differentiation of monocytes/macrophages under different conditions to acquire phenotypes characteristic of M2 macrophages.

Example I.D

Cytokines Involved in GMSC-Mediated Polarization of M2 Macrophages

Figure 4:
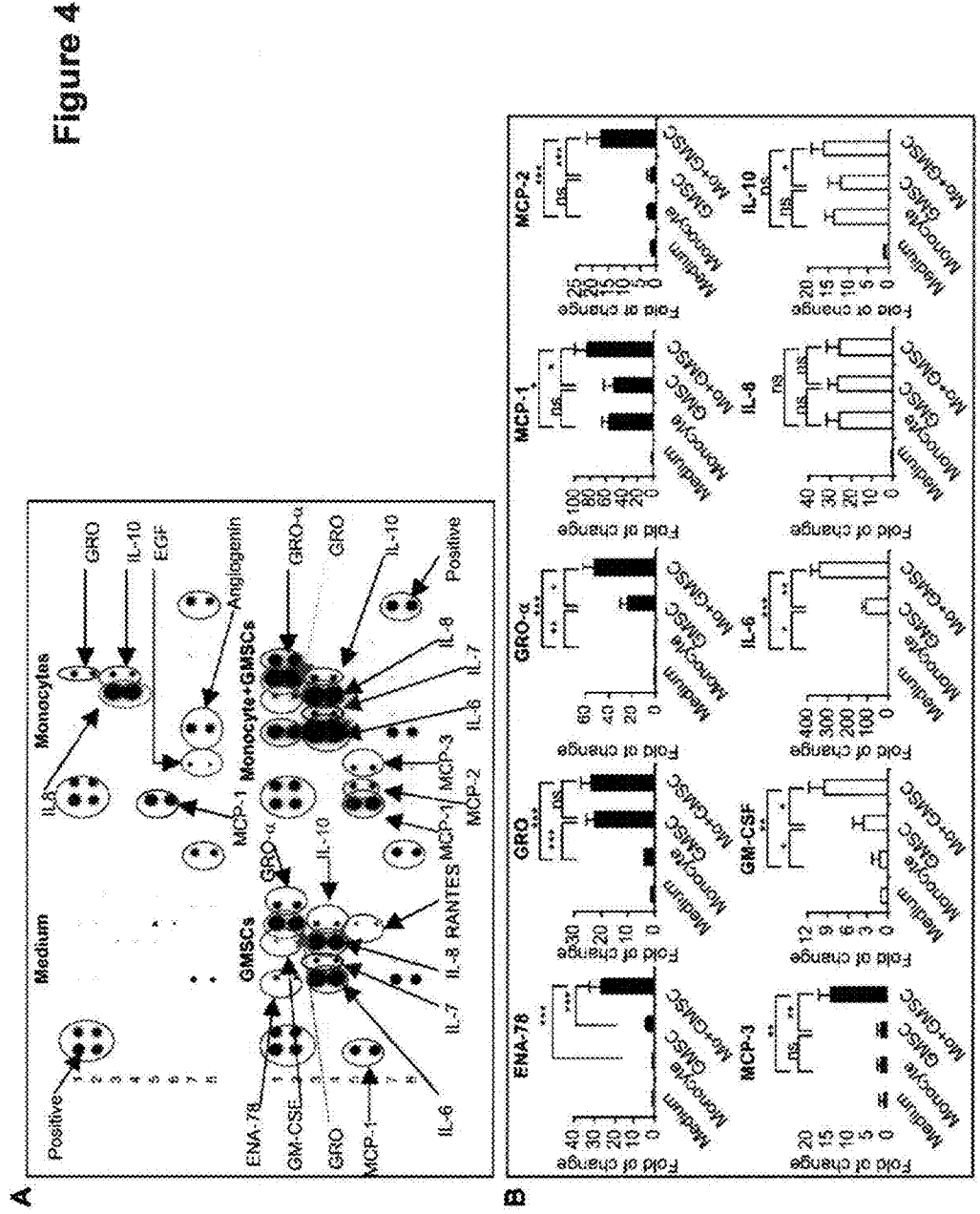
FIG. 4 shows that cytokine expression profile determined by antibody array. The cytokine expression profile in the conditioned media collected from macrophage, GMSC and their co-culture were detected using the RayBio Human Cytokine Antibody Array 3 (RayBiotech, Inc., Norcross, Ga.), which allows the detection of 42 cytokines, chemokines and growth factors in one experiment. The fresh medium without cell culture was used as a background control. (A): The representative image of cytokine antibody array. (B): The graphs show the relative intensity of spots of individual protein, whereby the intensity of the medium control was arbitrarily set as 1.0. The results were representative of three independent arrays. *P<0.05; P<0.01; *P<0.0001
Figure 5:
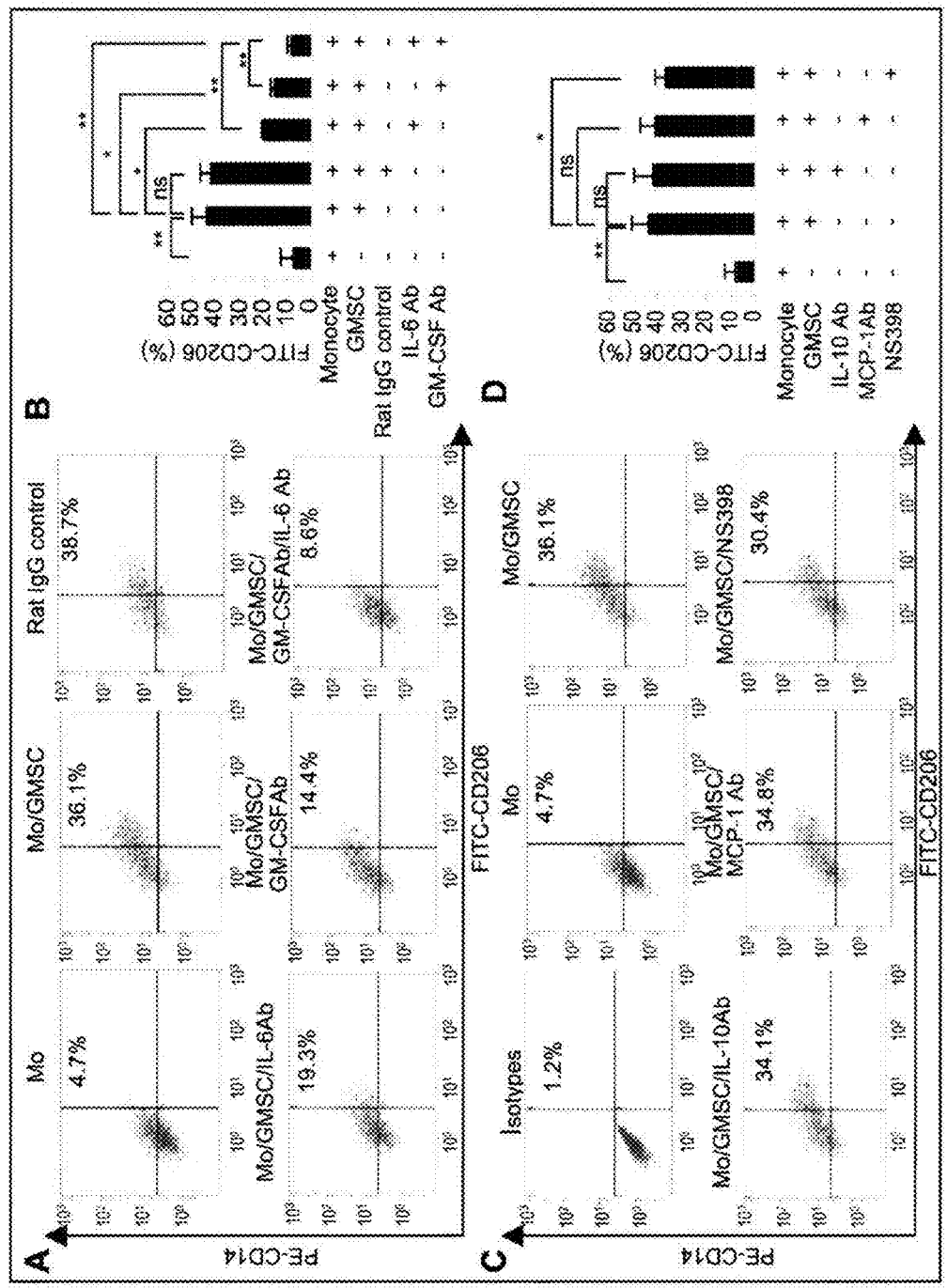
FIG. 5 shows that blocking IL-6 and GM-CSF synergistically inhibit GMSC-mediated induction of M2 macrophages. Macrophages were co-cultured with GMSCs in transwells for 72 h in the presence or absence of COX-2 inhibitor NS398 (10 uM) or specific neutralizing antibodies for IL-6, GM-CSF, CCL2 or IL-10 (10 ug/mL). An isotype-matched rat IgG was used as negative controls. (A, C): Cells were immunostained with PE-CD14 and FITC-CD206 antibodies and subjected to flow cytometry analysis. (B, D): The graphs show the average values from three independent experiments (mean±SEM). *P<0.05; **P<0.01; ns, no significance.

As described above, secretory factors may play an essential role in GMSC-induced polarization of M2 macrophages. We next screened for candidate soluble factors involved in GMSC-mediated M2 macrophage polarization using cytokine array analysis (FIG. 4A). Our results showed that PBMC-derived macrophages constitutively expressed high levels of IL-8 (26-fold), chemokine CCL2 (macrophage chemotactic protein-1, MCP-1, 57-fold) and IL-10 (14-fold), and moderate levels of epidermal growth factor (EGF, 4.8-fold), chemokine growth related oncogene (GRO-α, 3.6-fold), and angiogenin (2.5-fold). Compared to macrophages, GMSCs also constitutively expressed similarly high levels of IL-8 (26-fold), MCP-1 (49-fold) and IL-10 (12-fold), but a much higher level of GRO-α (22-fold vs. 3.6-fold). Uniquely, MSCs constitutively expressed a relatively high level of IL-6 (107-fold) and GRO-α (24-fold), and a moderate level of IL-7 (7-fold), GM-CSF (3.6-fold) and ENA-78 (3-fold). However, when compared to GMSC cultured alone, a dramatic increase in the secretion of ENA-78 (26-fold vs. 3-fold), GM-CSF (9.5-fold vs. 3.6-fold), IL-6 (340-fold vs. 107-fold), GRO-α (53-fold vs. 24-fold), MCP-1 (84-fold vs. 49-fold), MCP-2 (17-fold vs. 1.8-fold) and MCP-3 (14-fold vs. 1.8-fold) and a moderate increase in IL-10 (16-fold vs. 12-fold) were observed in the supernatants obtained from the co-cultured macrophages and GMSCs, whereas no additive increase in IL-8 and GRO-α was noticed (FIG. 4B). Based on previous findings that GMSCs constitutively expressed COX-2 [32] and that abundant levels of IL-6, CCL2, IL-10, GM-CSF were detected in the supernatants of co-cultured macrophages and GMSCs (FIG. 4), we then explore whether these secretory factors contribute to the polarization of macrophages toward an M2 phenotype. To this end, PBMC-derived macrophages were co-cultured with GMSCs in transwells in the presence or absence COX-2 inhibitor or various specific neutralizing antibodies for IL-6, CCL2, IL-10 and GM-CSF for 72 hours, and the percentage of M2 macrophages characterized as CD14+/CD206+ double-positive cells was determined by flow cytometry. We showed that addition of neutralizing antibodies specific for IL-6 and GM-CSF significantly decreased the percentage of M2 macrophages (P<0.05) as compared to the co-culture control treated with non-specific antibodies (FIG. 5A, 5B). A synergistic inhibitory effect on M2 macrophage generation was observed when both IL-6 and GM-CSF were neutralized (P<0.01) (FIG. 5A, 5B). Inhibition of COX-2 activity led to a moderate decrease of M2 macrophages, whereas neutralizing IL-10 and CCL-2 showed no obvious effects (FIG. 5C, 5D). These results indicate that both IL-6 and GM-CSF synergistically contribute to the induction of M2 macrophages mediated by co-culture with GMSCs.

Example I.E

GMSCs-Based Therapy Enhanced Skin Wound Healing in Mice

Figure 6:
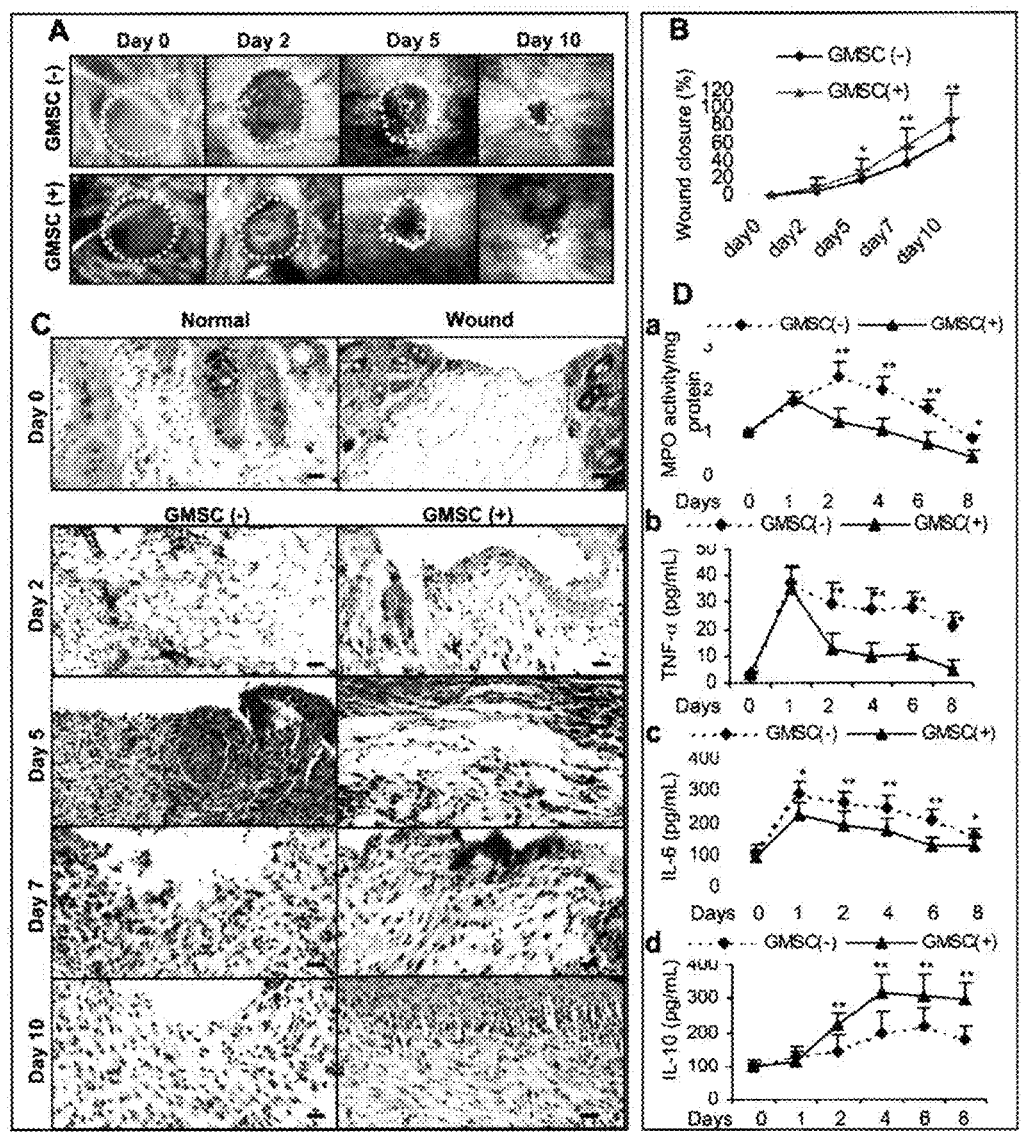
FIG. 6 shows that systemic administration of GMSCs accelerates wound closure and suppress local inflammatory responses in C57BL/6 mice. One day after excisional skin wound, GMSCs ($2\times10^6$/mice) were systemically infused by tail vein (i. v.) into mice and wound closure was daily observed. (A): Representative photographs of wounds at different time post-wounding with or without GMSC treatment. (B): Measurement of wound closure at different time points (n=4). The percentage of wound closure was calculated as: (area of original wound−area of measured wound)/area of original wound×100. (C): Representative hematoxylin and eosin (H & E)-stained paraffin-embedded sections of full-thickness incisional skin wounds from mice with or without receiving systemic administration of GMSCs (n=4). Mice were sacrificed at different days post wounding. Scale bars, 100 μm. (D): At different time points after wounding, skin samples were collected and tissue lysates were prepared for further analysis: (a) MPO activity assay. (b-d) ELISA assay on inflammatory cytokines, including TNF-α (b), IL-6 (c) and anti-inflammatory cytokine IL-10 (d). The results were representative of three independent experiments (mean SEM). *P<0.05; **P<0.01.

Given the essential roles of both MSCs [24, 30, 31] and M2 macrophages [10, 12, 27, 38] in wound healing, we explore the in vivo relevance of GMSC-induced M2 switch in wound repair using an excisional skin healing model in mice. First, we investigated whether GMSCs were capable of enhancing cutaneous excisional wound repair. To this end, GMSCs ($2\times10^6$/mice) were systemically injected into mice 1-day post full-thickness skin excision and wound closure was carefully measured daily (n=4). Our results showed that mice receiving systemic infusion of GMSCs displayed accelerated skin wound closure compared to the control mice without treatment, wherein the enhancement in wound closure appeared as early as day 3 and the wound became completely closed on day 10 (P<0.01) (FIG. 6A, 6B).

Figure 16:
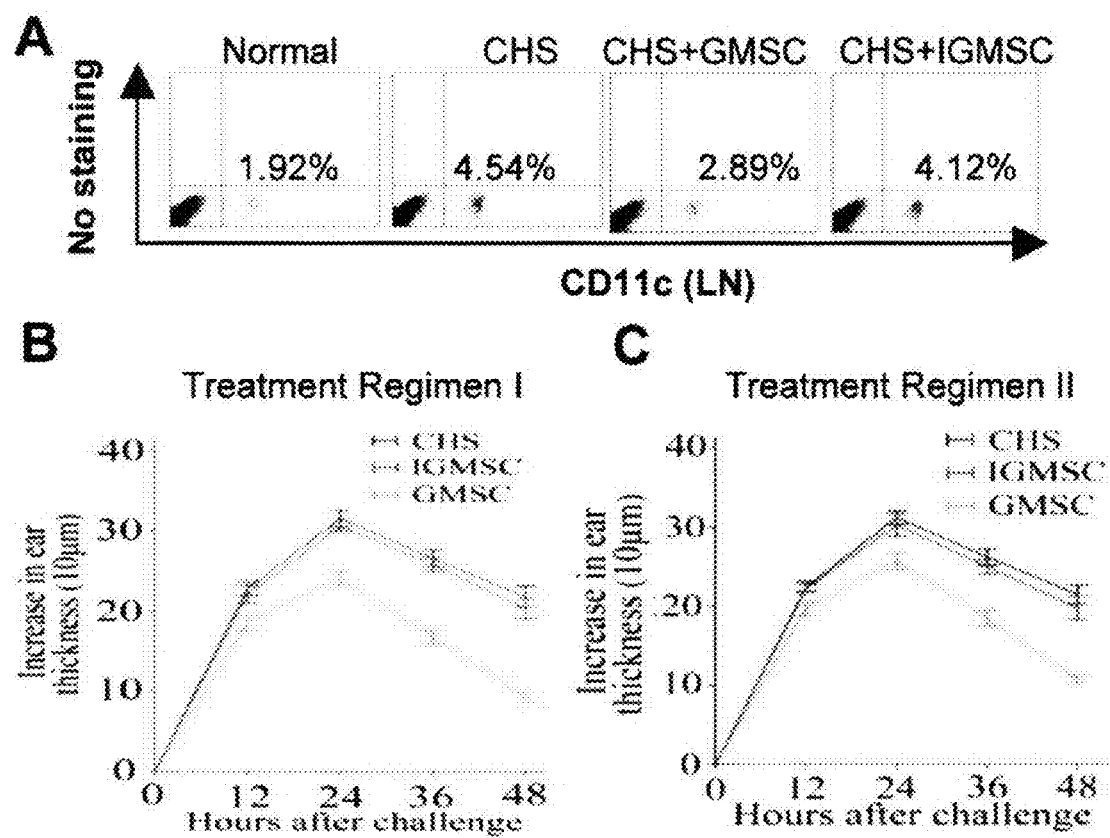
FIG. 16 shows A, GMSCs or GMSCs pretreated with 5|aM indomethacin (IGMSC, $2\times10^6$/mice) were systemically injected into mice via tail vein 1 day before sensitization with 1% oxazolone (regimen I). 48 h after challenge, dLNs were collected for single cell preparation. The number of CD11c+ cells was determined by flow cytometry. B and C, GMSCs or GMSCs pretreated with 5 μM indomethacin (IGMSC, $2\times10^6$/mice) were systemically injected into mice via tail vein either 1 day before sensitization (regimen I) or 1 day before challenge with 1% oxazolone (regimen II), and ear thickness (n=4) was measured at the indicated times. The results represent three independent experiments (mean±SEM).
Figure 20:
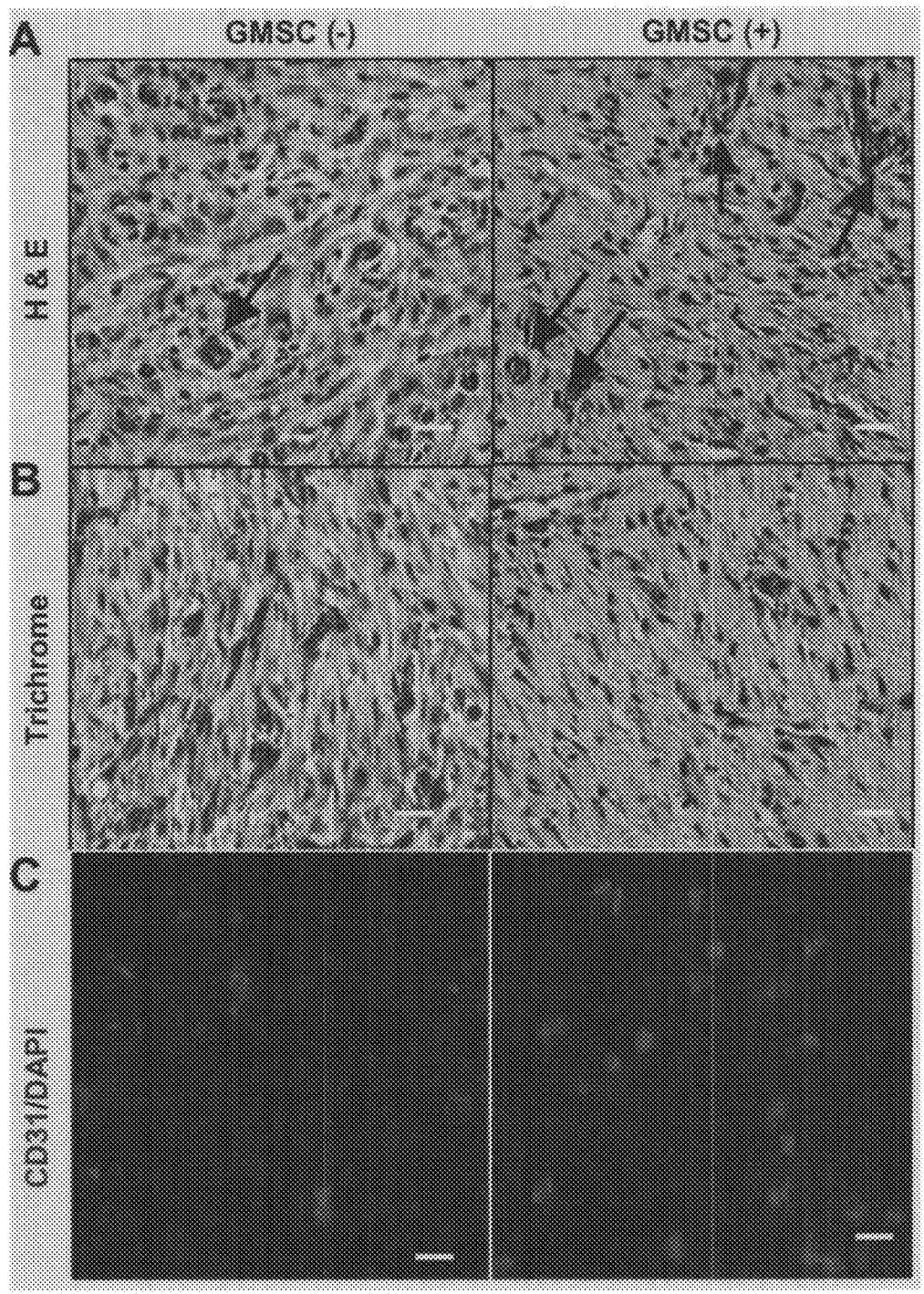
FIG. 20 shows Histological analysis of wounds on day 3, 5, and 7 showed a more organized granulation tissue proper at the excisional wound site in GMSC-treated mice as compared to the untreated group (FIG. 20A). Masson trichrome staining of GMSC-treated skin wounds on day 7 showed thick and densely packed collagen fibers, whereas thin and loosely packed basket-weaved collagen bundles were more apparent in untreated skin wounds (FIG. 20B). Abundant presence of microvascular structures and CD31-positive endothelial cells were observed in GMSC-treated wounds as compared to controls (FIG. 20C).
Figure 21:
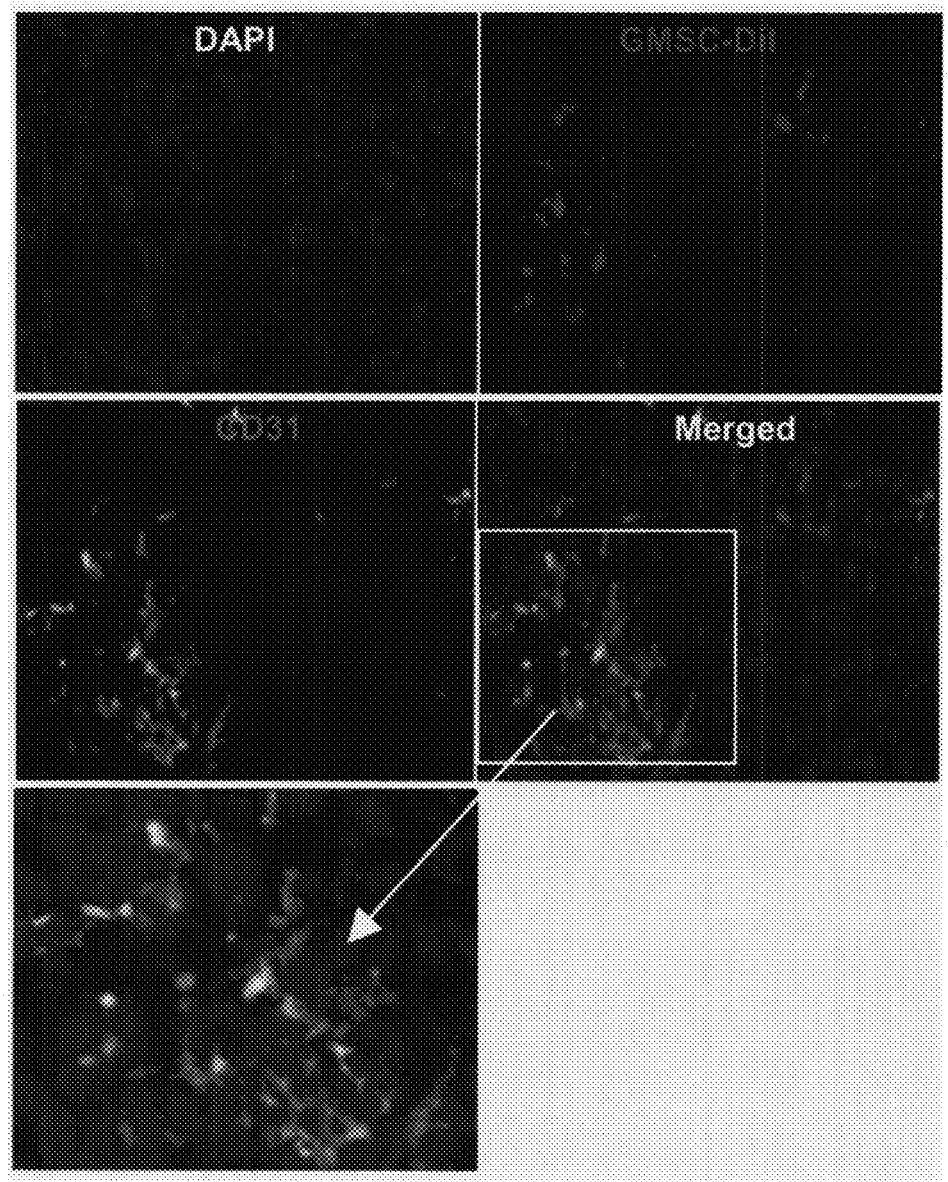
FIG. 21 shows that $CD31^+$ endothelial cells were localized in close spatial relationship to GMSCs pre-labeled with CM-DiI dye.

Histological analysis of wounds on day 3, 5, and 7 showed a more organized granulation tissue proper at the excisional wound site in GMSC-treated mice as compared to the untreated group (FIG. 20A). Masson trichrome staining of GMSC-treated skin wounds on day 7 showed thick and densely packed collagen fibers, whereas thin and loosely packed basket-weaved collagen bundles were more apparent in untreated skin wounds (supporting information FIG. 16B). In addition, abundant presence of microvascular structures and CD31-positive endothelial cells were observed in GMSC-treated wounds as compared to controls (FIG. 20C). Interestingly, the CD31+ endothelial cells were localized in close spatial relationship to GMSCs pre-labeled with CM-DiI dye (FIG. 21). Overall, we observed rapid re-epithelialization in GMSC-treated wounds (complete epithelialization in all 6 of 8 wounds examined; n=4) compared with untreated wounds (complete epithelialization in 2 of 8 wounds examined; n=4) on day 10 (FIG. 6C). These results indicate that enhancement of wound healing by systemic infusion of GMSCs involves enhanced re-epithelialization, collagen deposition and angiogenesis. We also observed no apparent benefit in wound healing when treated with normal skin fibroblasts.

Example 1.F

Interplay Between GMSCs and Macrophages Regulated the Local Inflammatory Response During Skin Wound Healing We next investigated the in vivo effects of GMSCs on inflammatory cell response and production of local inflammatory cytokines in skin wounds. Analysis of skin wounds on day 3, 5, and 7 following GMSC injection indicated that infiltration of inflammatory cells was significantly decreased in GMSC-treated wounds as compared to controls (FIG. 6C). GMSC treatment decreased neutrophil infiltration as represented by a time-dependent decrease in MPO activity in wounded skin at several time points post-wounding (FIG. 6Da). In addition, ELISA analysis showed that GMSC treatment significantly decreased the local levels of both proinflammatory cytokines, TNF-α and IL-6, and increased the anti-inflammatory cytokine IL-10 (FIG. 6Db-d). Without being limited by theory, it is believed that GMSC treatment promotes skin wound healing, at least in part, by suppressing inflammatory cell infiltration and pro-inflammatory cytokine secretion as well as by increasing the production of IL-10 at the local wound sites.

Figure 7:
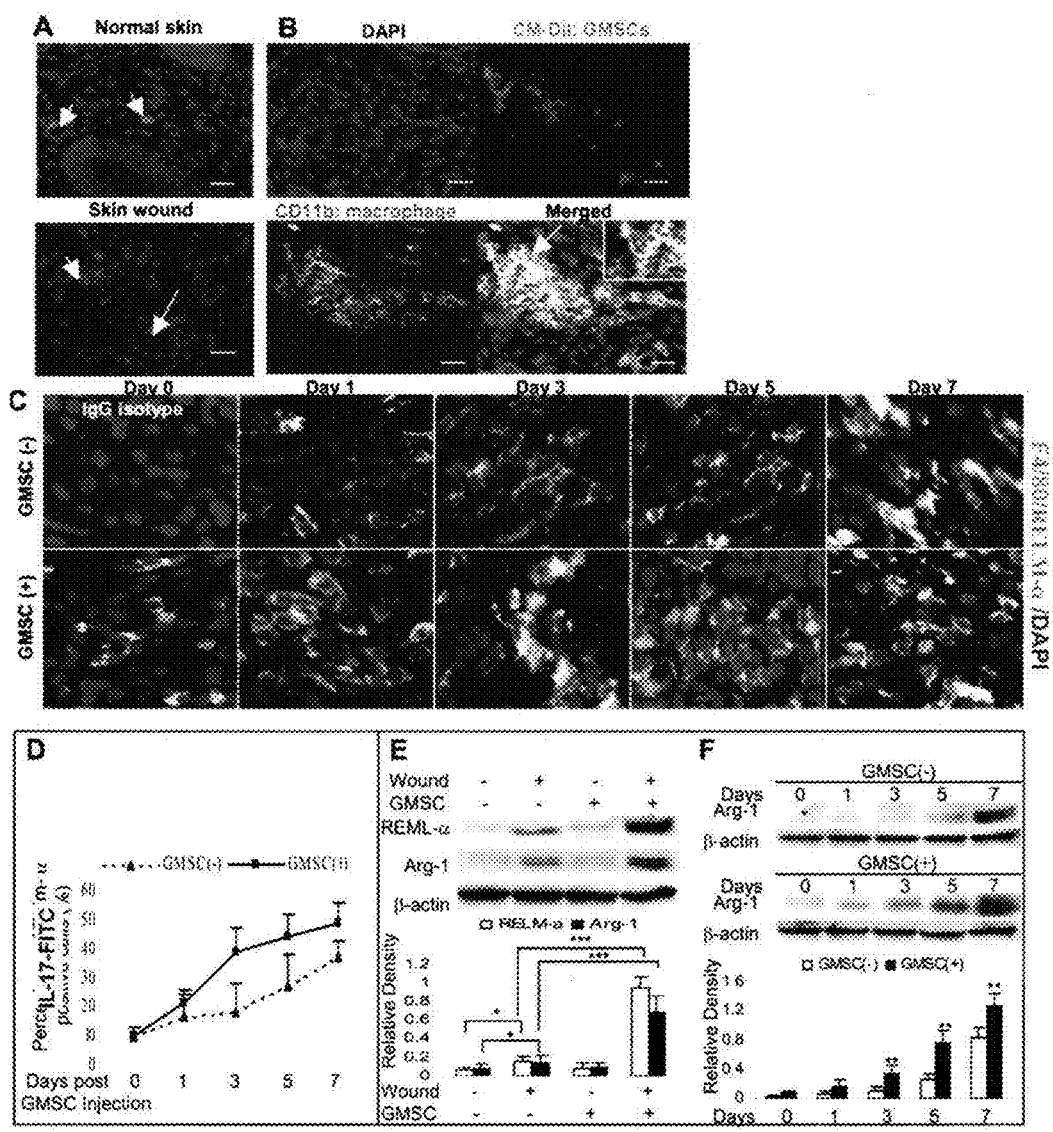
FIG. 7 shows that interactions of homed GMSCs with macrophages during wound healing. (A): GMSCs pre-labeled with CM-DiI were systemically infused by tail vein (i.v.) into mice one day after skin wounding. 7 days after cell injection, skin tissues were frozen sectioned and observed under a fluorescence microscope, whereby normal skin on the other side of the same mice were used as controls. (B): Frozen sections of wounded skins from mice after injection with CM-DiI pre-labeled GMSCs were immunostained with FITC-conjugated antibody for mice CD11b. Scale bars, 50 um. The results were representative of at least three independent experiments. (C): Frozen sections of full-thickness incisional skin wounds from mice after treatment with GMSCs for different days were dual-color immunostained with specific antibodies for F4/80 (Green) and RELM-α (Red). Scale bars, 50 μm. (D): Quantification of M2 macrophages positive for RELM-α. (E) Western blot analysis of arginase-1 (Arg-1) and RELM-α expression in skin wounds 7 days post GMSC treatment. (F) Time-dependent increases in Arg-1 and RELM-α expression induced by GMSC treatment. The results are representative of three independent experiments. *P<0.05; P<0.01; *P<0.001.
Figure 22:
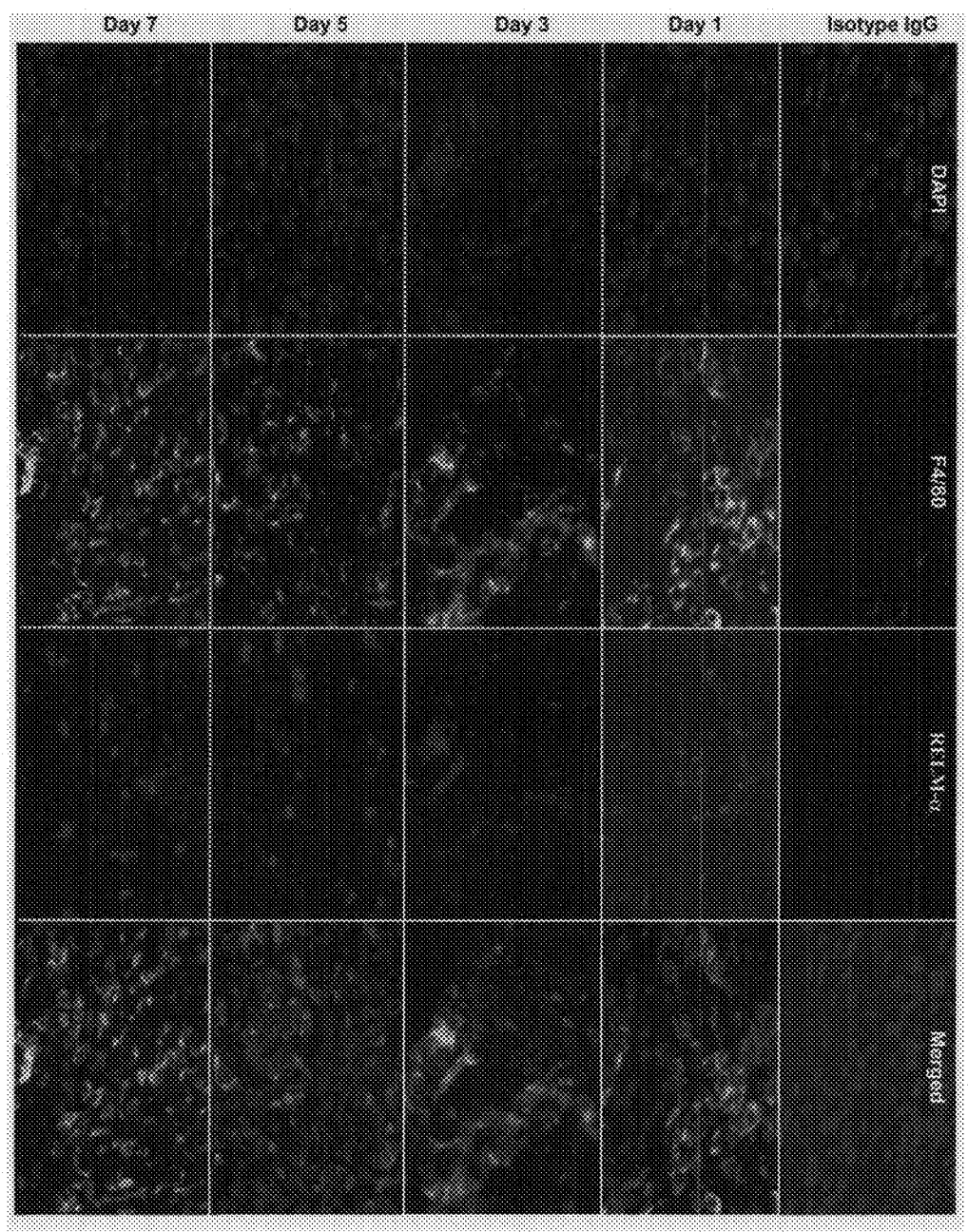
FIG. 22 shows that GMSC treatment led to a time-dependent increase in the number of F4/80 and RELM-α-positive macrophages.

To explore the interactions of homed GMSCs and host macrophages at the wounds, GMSCs pre-labeled with CM-DiI were systemically injected into mice. As shown in FIG. 7 A, the number of GMSCs homing to injured sites significantly increased as compared with that in normal skin, and the homed GMSCs were in close proximity with F4/80-positive macrophages (FIG. 7B). Then we further investigated the in vivo effects of GMSCs on the phenotype of macrophages in skin wounds. Dual-color immunofluorescence studies were performed using specific antibodies for F4/80 and resistin-like molecule (RELM)-α, also known as Fizz1 (found in inflammatory zone 1), a well-known marker for M2 macrophages [11, 38]. As shown, GMSC treatment led to a time-dependent increase in the number of F4/80 and RELM-α-positive macrophages (FIG. 7C, 7D; FIG. 22). The increased expression of RELM-α in skin wounds on day 7 after GMSC treatment was further confirmed by Western blot (FIG. 7E). Meanwhile, we also detected the expression of arginase-1 in skin wounds, another well-known marker for M2 macrophage [11, 39]. We observed a similar increase in the expression of arginase-1 protein in skin wounds on day 7 after GMSC injection as compared with controls (FIG. 7E). Furthermore, a time-dependent increase in arginase-1 protein expression was also demonstrated in skin wounds after GMSC treatment on different days post-wounding (FIG. 7F). These findings indicate that GMSCs promote alternative activation of host macrophages infiltrated at the wounded skin sites, contributing to the regulation of the inflammatory response and enhancing the healing of excisional skin in mice.

Materials and Methods Used in Example I

Animals.

C57BL/6J mice (male, 8-10 week-old) were obtained from Jackson Laboratories (Bar Harbor, Me., http://www.jax.org) and group-housed at the Animal Facility of University of Southern California (USC). All animal care and experiments were performed under the institutional protocols approved by the Institutional Animal Care and Use Committee (IACUC) at USC.

Cytokines and Reagents.

Recombinant human IL-4, CCL-2 (MCP-1), IL-6 and M-CSF were purchased from PeproTech (Rocky Hill, N.J., http://www.peprotech.com). Lipopolysaccharide (LPS) from *Escherichia coli* 055:B5, phorbol 12-myristate 13-acetate (PMA), Brefeldin A were obtained from Sigma-Aldrich (St. Louis, Mo., http://www.sigmaaldrich.com). Antibodies include anti-CD14 allophycocyanin (APC), anti-CD11a fluorescein isothiocyanate (FITC), anti-CD90 peridinin chlorophyll protein (PerCp)-Cy5.5, anti-IL-6-PE, anti-IL-10-PE, anti-TNFα-PE and anti-IL-17-FITC (eBiosciences, San Diego, Calif., http://www.ebioscience.com), anti-CD206 (BD Biosciences, San Jose, Calif., http://www.bdbiosciences.com), anti-CD 14-phycoerythrin (PE), anti-CD4-(PerCp)-Cy5.5, anti-CD86-PE, anti-CD209 (DC-SIGN)—PE (BioLegend, San Diego, Calif., http://www.biolegend.com).

Cell Culture.

The isolation and culture of human bone marrow and gingival tissue-derived MSCs, human peripheral blood-derived CD14$^+$ monocytes, human acute monocytic leukemia cell line THP-1 [33], and human foreskin fibroblasts (Hs68) are as in published accounts of Dr. Le. Both THP-1 and Hs68 cell lines were from ATCC (Manassas, Va.). The gingival tissues were obtained as remnants of discarded tissues following routine dental procedures at USC School of Dentistry and the Outpatient Dental Clinic at Los Angeles County (LAC)-USC Medical Center under the approved Institutional Review Board (IRB) protocol at USC.

Co-Culture of Macrophage with GMSCs.

For co-culture studies, $2 \times 10^5$ GMSCs were seeded with PBMC-derived macrophages on day 7 and cultured for another 3 days. For transwell co-culture, 0.4-μm pore size Corning transwell inserts (VWR, West Chester, Pa., https://www.vwrsp.com) were placed into the 6-well plate with macrophages initially seeded at the bottom well, while $2 \times 10^5$ GMSCs were seeded onto the inserts and continued to culture for another 3 days [20].

Flow Cytometry.

Cells were processed for standard flow cytometric analysis of cell surface markers and analyzed using a FACS Calibur (BD Biosciences). To detect intracellular cytokine, macrophages were stimulated with 1 μg/ml LPS either for 24 hours (IL-10), or 5 hours (IL-6), or 1 (ug/ml ionomycin with 50 nM PMA for 5 hours (TNF-α), in the presence of 10 μg/ml Brefeldin A (Sigma) to block the secretion of cytokines [20]. After stained for CD206, cells were processed with BD Cytofix/Cytoper™ Fixation/Permeabilization kit (BD Biosciences), followed by incubation with specific antibodies for different cytokines, and analyzed by flow cytometry.

Phagocytic Assay.

To determine the phagocytic activity of macrophages co-cultured with GMSCs in transwells, FITC-coupled Zymosan particles (Sigma; 25 μg/mL) were added into the cultures and incubated at 37° C. or 4° C. for 1 hour. After washing, cells were fixed with 1% paraformaldehyde and the uptake of FITC-coupled Zymosan particles was determined by flow cytometry.

Cytokine Antibody Array.

Cytokine expression profiles in the supernatants of GMSCs, macrophage, and their co-cultures were detected using RayBio Human Cytokine Antibody Array 3 (RayBiotech, Inc., Norcross, Ga., http://www.raybiotech.com) and semi-quantified following the manufacturer's instructions. The medium alone was used as background control and arbitrarily set as 1.0.

Skin Wound Healing Model and GMSC Treatment.

Mice were randomly divided into control and GMSC-treated groups, and the excisional full-thickness skin wound splinting model was generated as described previously [29, 31].

MPO Activity Assay.

The infiltration of neutrophils in skin wound was assessed by measuring myeloperoxidase (MPO) activity as described previously [34, 35].

Histological and Immunohistochemical Studies.

Standard hematoxylin and eosin (H & E) staining and dual-color immunofluorescence studies using specific primary antibodies for mice F4/80 and RELM-α were performed as previously described [32]. Isotype-matched control antibodies (eBiosciences) were used as negative controls. For semi-quantification, positive signals in at least 5 random high-power fields (HPF) were visualized, counted and expressed as percentage of total DAPI-positive cells (mean±SD).

Western Blot Analysis.

Cell lysates or mice skin homogenates (50~100 μg of total protein) were separated on polyacrylamide-SDS gel and electroblotted onto nitrocellulose membrane (BioRad, Hercules, Calif., http://www.bio-rad.com), After blocking with TBS/5% nonfat dry milk, the membrane was incubated with antibodies against mice arginase-1 (Santa Cruz Biotech, Inc., Santa Cruz, Calif. http://www.scbt.com), RELM-α (PeproTech), or human NFκB p50 (BioLegend) or p65 (Millipore, Billerica, Mass., http://www.millipore.com) followed by incubation with a horseradish peroxidase (HRP)-conjugated secondary antibody, and the signals were visualized by enhanced chemiluminescence detection (ECL) (PIERCE, Rockford, Ill., http://www.piercenet.com). The blots were also re-probed with a specific antibody against b-actin (Sigma).

ELISA.

The concentration of IL-6, IL-10 and TNF-α in skin wound lysates of mice, and human IL-6, IL-10 and TNF-α levels in the supernatants of cultured cells were detected using ELISA kits (eBioscience).

Statistical Analysis.

All data are expressed as mean±SEM from at least three independent experiments. Differences between experimental and control groups were analyzed by two-tailed unpaired Student's t-test using SPSS. P-values less than 0.05 were considered statistically significant.

Example II

GMSCs Attenuate Contact Hypersensitivity Via Prostaglandin $E_2$-Dependent Mechanisms Allergic contact dermatitis (ACD), also referred to as contact hypersensitivity (CHS), represents one of the most common inflammatory skin diseases with huge socioeconomic impacts worldwide. Pathophysiologically, ACD or CHS belongs to type IV or delayed-type hypersensitivity (DTH) reactions, wherein two temporally and spatially dissociated phases, the sensitization and the elicitation or challenge phase, led to full manifestation of DTH (62). Initially, the resident antigen-presenting cells (APCs), particularly, dendritic cells (Des), process haptens or allergens and migrate to the regional draining LNs, where they convert $CD8^+$ cytotoxic T lymphocytes and naïve $CD4^+$ T cells into hapten-specific $CD8^+$ and $CD4^+$ effector or memory T cells as well as regulatory T cells (Tregs). These sensitized and activated T cells subsequently circulate in the peripheral blood and reside at local skins and elicit the efferent limb of the immune response at the re-encounter of the same type of hapten (62, 63). Studies have shown that the elicitation of CHS is mostly due to the rapid recruitment of chemical-specific $CD8^+$ T cells, which induce apoptosis of keratinocytes and the recruitment of leukocytes by secreting INF-γ, IL-17, perforin and granzyme (72, 73). Additionally, $CD4^+$ $T_H$-1 and $T_H$-17 contribute to the extension of the inflammatory reactions by releasing pro-inflammatory cytokines that activate keratinocytes and other skin resident cells (74-76), thereby leading to intense inflammatory reactions and the development of the clinical eczematous lesion. Most recently, several lines of evidence have demonstrated the critical role of mast cells (MCs), a distinct cellular component of the innate immune system, in delayed-type allergic reactions, in which MCs contribute to CHS development by promoting the recruitment of neutrophils and DCs (83), by enhancing T cell activation (89) as well as by regulating the magnitude and cytokine microenvironment of CHS response (90), whereas abrogation of high-affinity IgE receptor-mediated mast cell activation at the effector phase prevents CHS (87). Meanwhile, emerging evidence supports the important role of $CD4^+CD25^+FoxP3^+$ T regulatory cells in preventing the development of allergic reactions to haptens/allergens contacting the skin, and in limiting the magnitude of the inflammatory process in already sensitized individuals (77-79).

Figure 8:
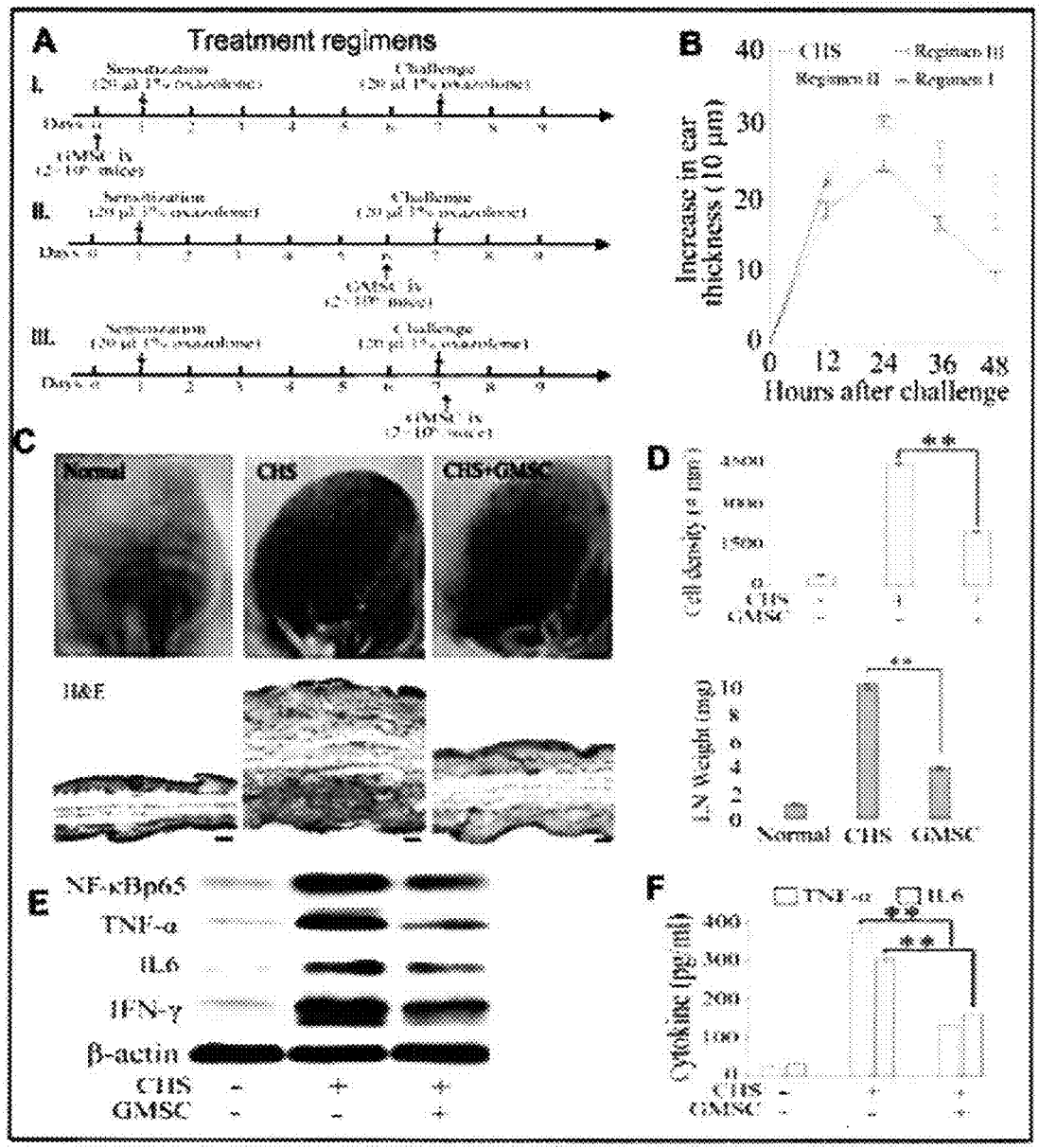
FIG. 8 shows that GMSC-based therapy attenuates CHS. A, Experimental protocols showing different treatment regimens using GMSCs. GMSCs ($2\times10^6$/mice) were systemically injected into mice via tail vein either 1 day before sensitization with 1% oxazolone (regimen I), 1 day before challenge (regimen H) or 1 h after challenge with 1% oxazolone (regimen III). 48 h after challenge, ear and local draining lymph node (dLN) samples were collected for further analysis. B, Ear thickness (n=4) was measured at the indicated times after challenge in different experimental groups. C, Representative photos of the ear and images of H & E staining of ear samples from mice following treatment regiment II with GMSCs. Scale bars, 200 μm. D, Quantification of cellular components in CHS ears and dLNs. E and F, GMSCs inhibited the production of inflammatory cytokines in local ears as determined by Western blot and ELISA. The results represent three independent experiments (mean±SEM). *P<0.05; **P<0.01.
Figure 9:
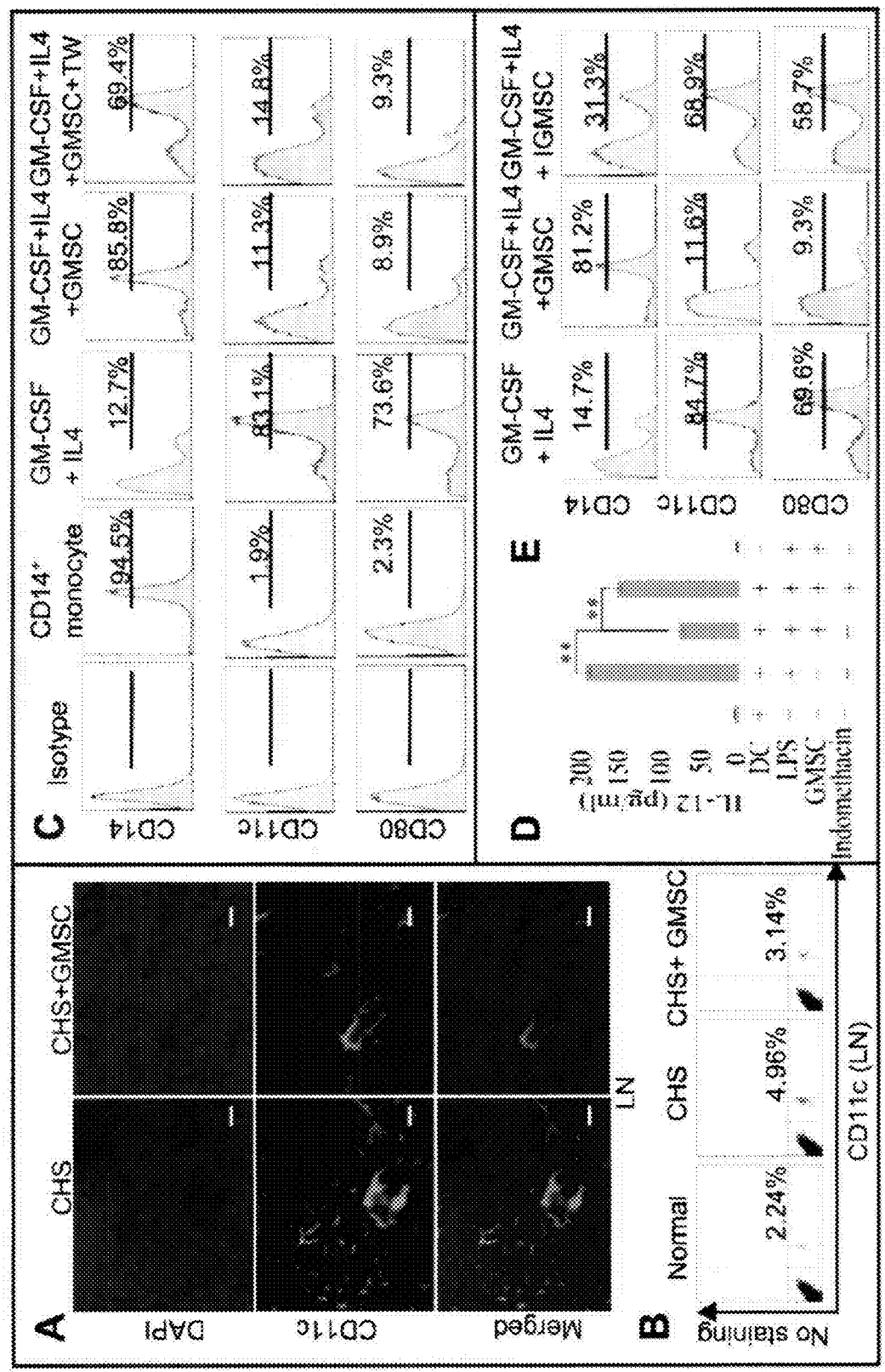
FIG. 9 shows that attenuation of CHS by GMSCs involves PGE2-dependent inhibition of DCs. A, The infiltration of CD11c$^+$ DCs in the regional dLNs was determined by immunofluorescence staining. B, The percentage of CD11c$^+$ DCs in dLNs was determined by flow cytometry. C, GMSCs inhibited the differentiation and maturation of DCs. CD14$^+$ monocytes were cultured alone or co-cultured with GMSCs (1:1) in direct cell-cell contact or in transwells (TW) in the DC-induction medium containing GM-CSF (20 ng/mL) and IL-4 (20 ng/mL). 7 days later, the number of CD11c$^+$ and CD80$^+$ DCs was determined by flow cytometry. D, GMSCs dramatically reduced IL-12 secretion by DCs in response to LPS stimulation. E, GMSCs pretreated with 5liM indomethacin (IGMSCs) were co-cultured with CD14$^+$ monocytes in transwells under the same condition as described in C, and then the number of CD11c$^+$ and CD80+ DCs was determined by flow cytometry. The results represent three independent experiments (mean±SEM). *P<0.05; **P<0.01.
Figure 10:
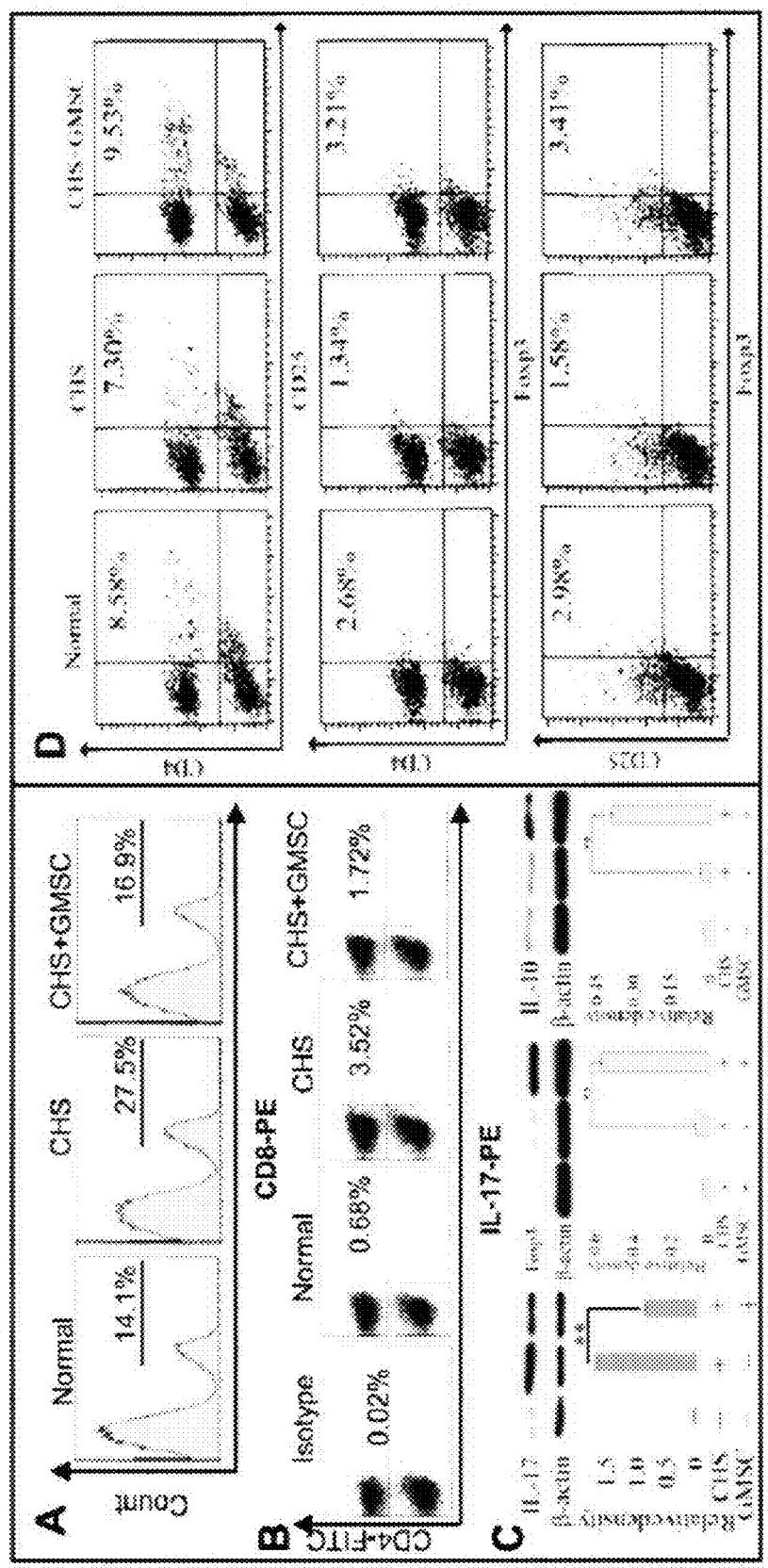
FIG. 10 shows that attenuation of CHS by GMSCs is associated with their modulatory effects on multiple effector T cells. Following treatment regimen II with GMSCs, ear and local draining lymph node (dLN) samples were collected at 48 h after challenge for further analysis. A and B, The infiltration of CD8$^+$ T cells and $T_H17$ in the regional dLNs was determined by flow cytometry. C, The expression IL-17, Foxp3 and IL-10 in CHS ears were determined by Western blot, wherein the graphs showed their relative density after normalization to the intensity of p-actin bands. D, The infiltration of Treg in the regional dLNs was determined by flow cytometry. The results represent three independent experiments (mean±SEM). *P<0.05; **P<0.01.
Figure 11:
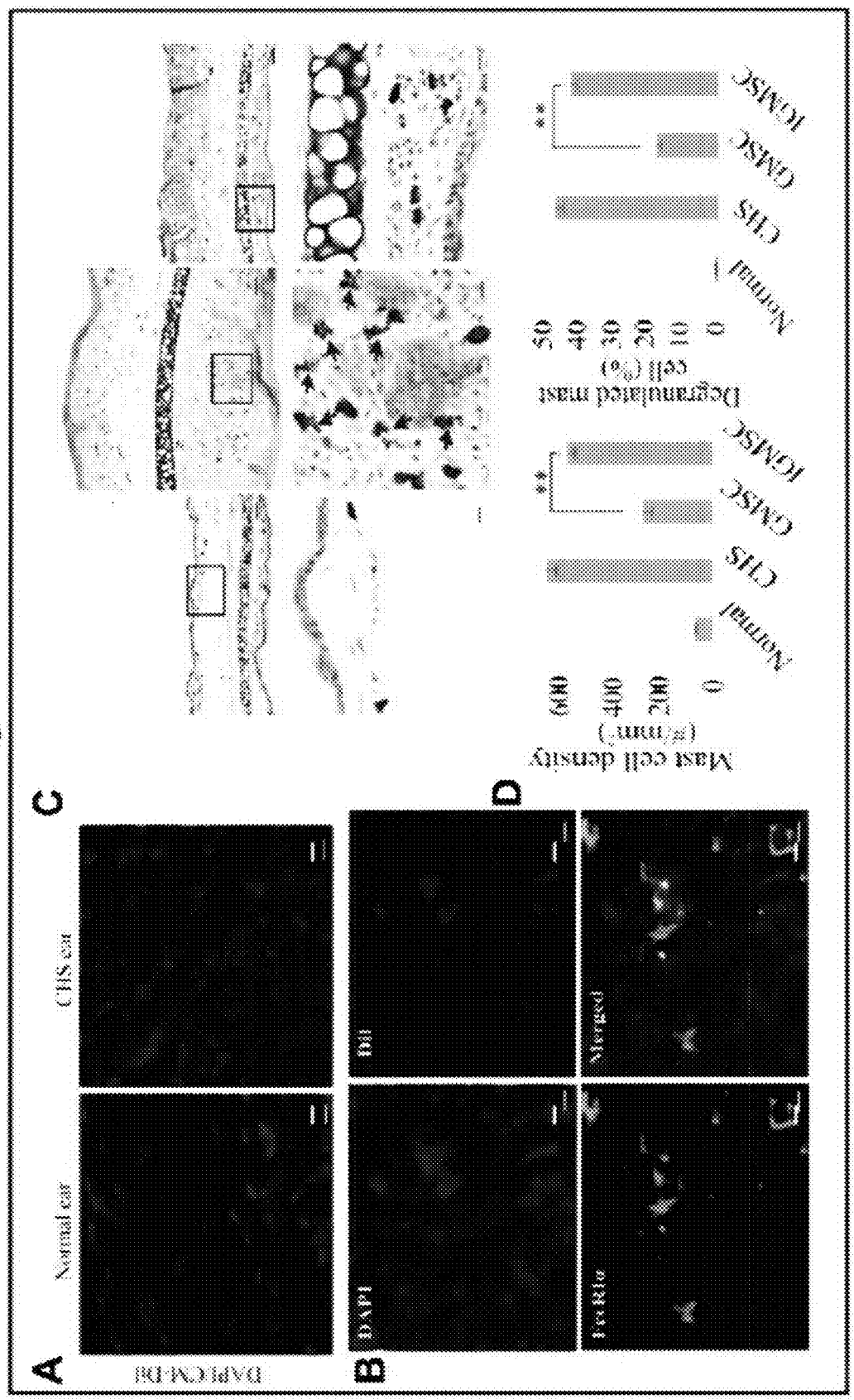
FIG. 11 shows the interplay of homed GMSCs and MCs in CHS model, GMSCs prelabeled with CM-DiI were systemically injected into mice 1 day before challenge (regimen H). 48 h after challenge, ear samples were collected for further analysis. A and B, GMSCs (Red) homed to the inflammatory sites were in proximity with MCs (Green) as determined by immunofluorescence staining with a specific antibody for FceRIa. C and D, GMSCs treatment decreased the number and degranulation of MCs as determined by toluidine blue staining. (red arrow: degranulated MCs). The results represent three independent experiments (mean±SEM). *P<0.05; **P<0.01.

According to the different stages of CHS, we first evaluated the therapeutic effects of GMSCs at different intervention time points using different treatment regimens, one day before sensitization with 1% oxozolone (treatment regimen I), or one day before challenge (treatment regimen II), or at 2 h after challenge (treatment regimen III) (FIG. 8A). We showed that treatment regimen I and II exhibited much better therapeutic effects than treatment regimen III, thereby indicating that the sensitization phase is the optimal time window for GMSC-based therapy of CHS. Our results showed that the attenuation of CHS induced by GMSC treatment was accompanied with a significantly reduced infiltration of dendritic cells, $CD8^+$ T cells and $T_H$-17 effector cells at the regional draining LNs and local allergic or challenged areas, and a markedly increased infiltration of Tregs (FIGS. 9 and 10). More importantly, we found that treatment with GMSC also dramatically reduced the total number of mast cells (MCs) as well as the percentage of degranulated MCs in the allergic ears (FIG. 11). These findings indicate that GMSCs attenuate CHS through targeting multiple types of immune cells that play critical roles at different phases of the delayed type hypersensitivity reaction. However, it is noteworthy that complicated crosstalks exist among these innate and adaptive immune cells in the immunomodulation of CHS. For instance, the early activated $CD8^+$ cytotoxic T cells are responsible not only for the priming of $CD4^+$ T cells but also the infiltration of leukocytes into the contact sites (72, 73); IL-17 was shown to amplify CHS by licensing hapten nonspecific $T_H$-1 cells to kill autologous keratinocytes (76); Tregs prevent and limit allergic and inflammatory reactions by countering against the function of a variety of immune cells such as DCs, MCs, CD8 and $CD4^+$ effector T cells (77-79). Meanwhile, MCs can promote the migration or influx of DCs into an inflamed LN through the secretion of TNF-α or other inflammatory mediators (83, 91, 92). Therefore, further studies are warranted to explore whether and how GMSCs affect the immunomodulatory networks conferred by these immune cells during the CHS.

Figure 13:
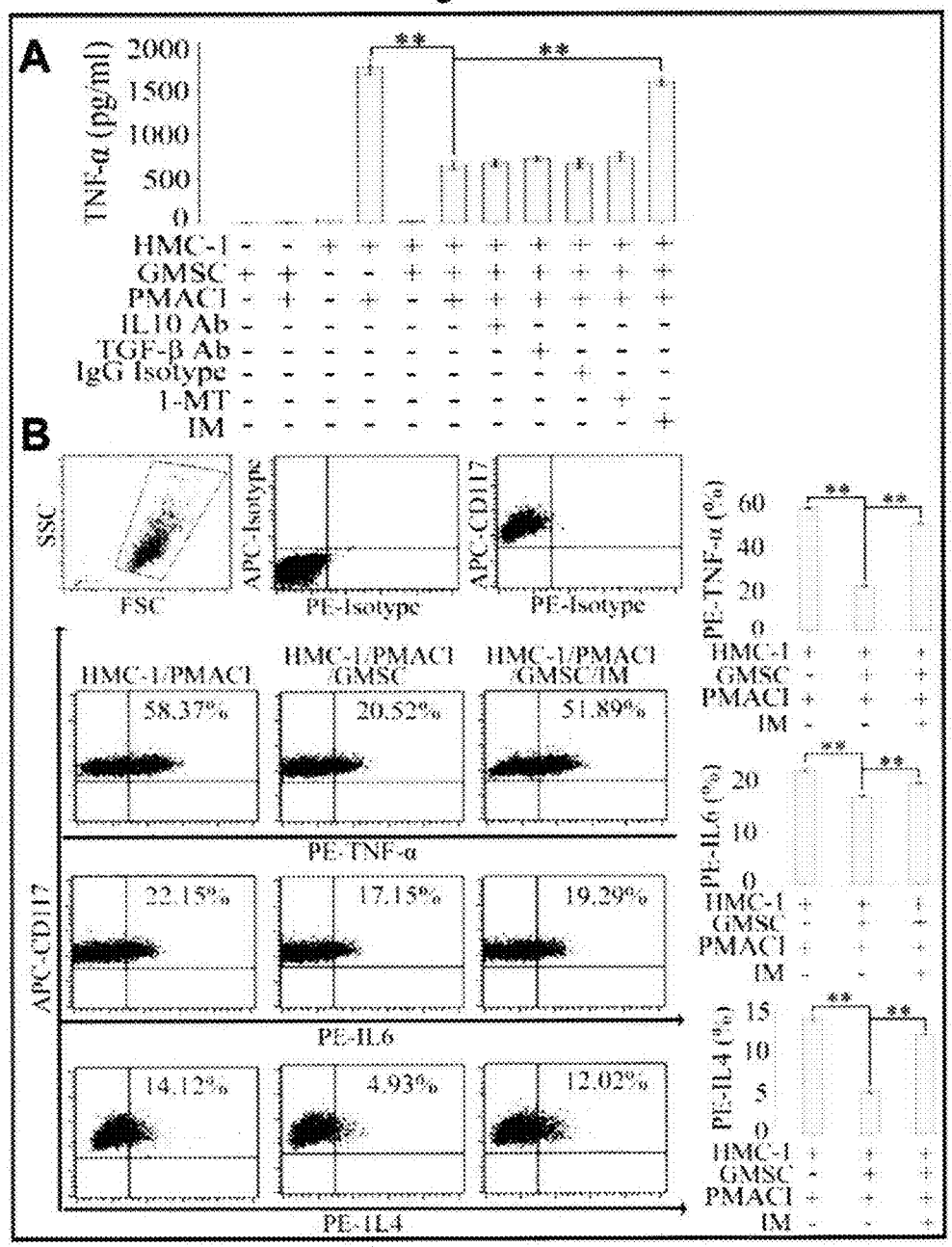
FIG. 13 shows that $PGE_2$ plays a key role in GMSC-mediated suppression of de novo synthesis of inflammatory cytokines in HMC-1 cells. HMC-1 cells were co-cultured with GMSCs for 72 h in transwells in the presence or absence of specific neutralizing antibodies (10 μg/mL) for either TGF-β1 or IL-10, or specific inhibitors for IDO (1-MT) or COX1/2 (indomethacin, IM). A, Following stimulation with PMACI, the secretory TNF-α in the supernatants was determined using ELISA. B, PMACI-stimulated expression of intracellular cytokines was determined using flow cytometry. The results represent three independent experiments (mean±SEM). *P<0.05; **P<0.01.
Figure 14:
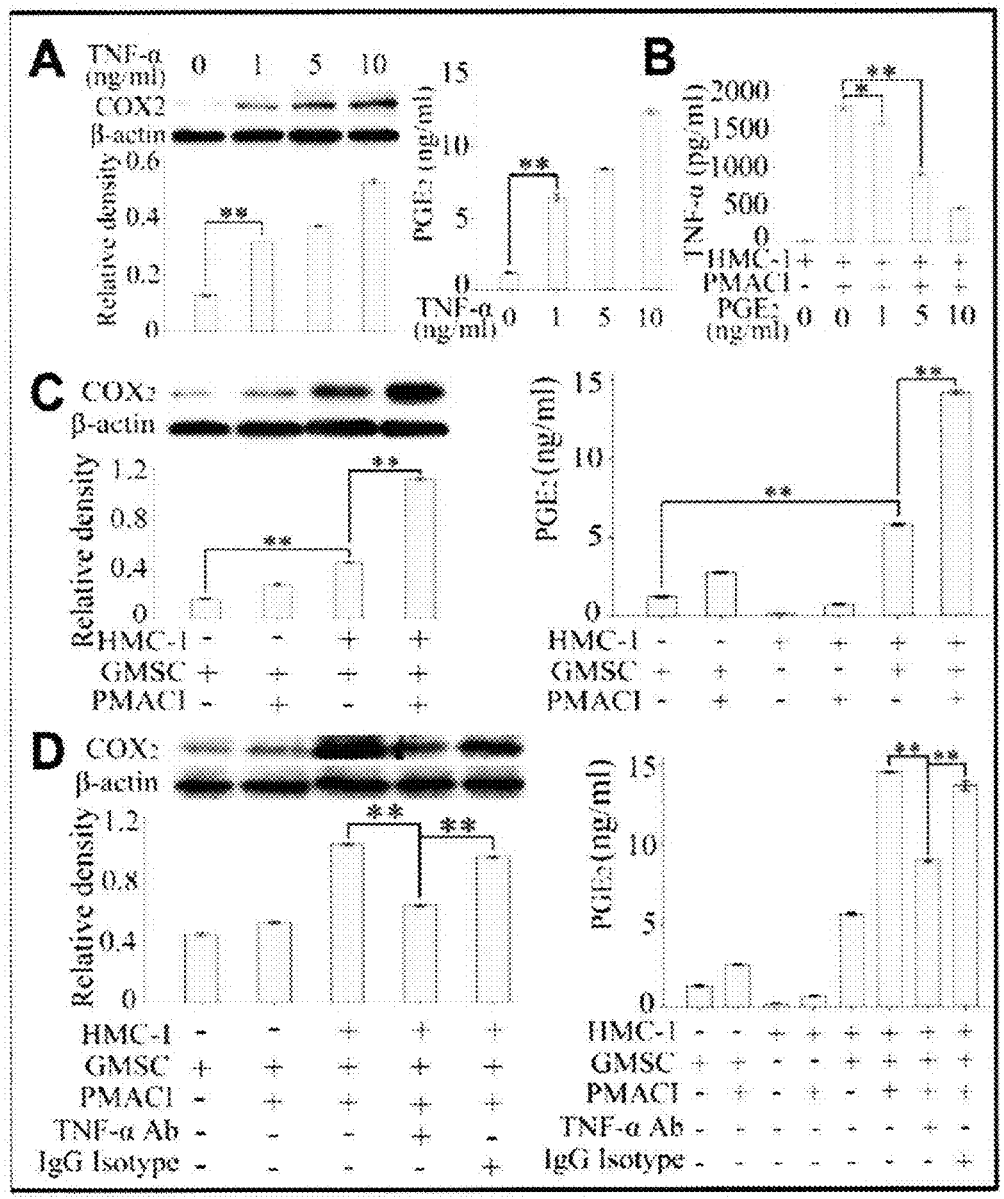
FIG. 14 shows that GMSCs interact with HMC-1 cells via TNF-α-PGE2 feedback loop. A and B, exogenous TNF-α induces a dose-dependent increase in COX-2 expression and $PGE_2$ production in GMSCs. B, exogenous $PGE_2$ inhibits PMACI-induced TNF-α expression in a dose-dependent manner. C, Co-cultured HMC-1 cells in the presence of PMACI enhanced the COX-2 expression and the $PGE_2$ production by GMSCs. D, Neutralizing TNF-α decreased COX-2 expression and $PGE_2$ production by GMSCs co-cultured with HMC-1 cells stimulated by PMACI. The results represent three independent experiments (mean±SEM). *P<0.05; **P<0.01.

Based on a series of in vivo and in vitro studies using specific neutralizing antibodies and inhibitors, we also demonstrated that the immunomodulatory function of GMSCs in CHS depends on their expression of $COXs/PGE_2$ due to the following important findings: 1) Pretreatment of GMSCs with indomethacin at a dosage (5 μM) that can completely block $PGE_2$ secretion induced by TNF-α stimulation without affecting cell viability; 2) GMSCs lost their suppressive effects on CHS and correspondingly, the infiltration and activation of DCs, $CD8^+$, TH-17 as well as MCs if pretreated with indomethacin before systemic injection into mice; 3) In vitro studies confirmed that the GMSCs pretreated with indomethacin before co-culture lost their capabilities to inhibit DC differentiation and PMA-stimulated activation of MCs (FIG. 9 and FIG. 13). These results are in consistent with previous findings, demonstrating that $PGE_2$ is critical to the immunosuppressive effects on T cells, DCs, NKs, macrophages conferred by different types of adult MSCs, including BMSCs, ADSCs and human umbilical cord MSCs (56, 57, 93-97) in different disease models in mice such as experimental autoimmune encephalomyelitis (EAE) (98) and experimental arthritis (99). Similar to our findings, using different experimental approaches and in vivo models Brown et al has recently reported that COX-2 acts as a crucial intermediate in mice bone marrow stromal cells (mBMSCs)-driven suppression of MC functions, and that the presence of MCs either in contact with BMSCs or in a transwell system is required to elicit the in vitro suppressive effect of BMSCs. Moreover, we disclose herein that MC-derived TNF-α may act as an important feedback signal in the cross-talk between mast cell and GMSCs (FIG. 14). All together, our findings have provided compelling evidence that GMSCs exert their immunomodulatory effects on multiple types of immune cells in CHS through a major common $COXs/PGE_2$ pathway.

In summary, we have demonstrated that systemic application of GMSCs significantly suppressed both the sensitization and elicitation of CHS through modulating the function of multiple types of innate and adaptive immune cells through the $COXs/PGE_2$ pathway. These findings further support the notion that GMSCs, a unique population of MSCs with functional similarities to BMSCs, and specifically, their ease of isolation, accessible tissue source, and rapid ex vivo expansion, are a promising cell source for stem cell-based therapies of inflammatory and allergic diseases.

Example II.A

Treatment with GMSCs can Suppress Delayed Type Hypersensitivity

Figure 15:
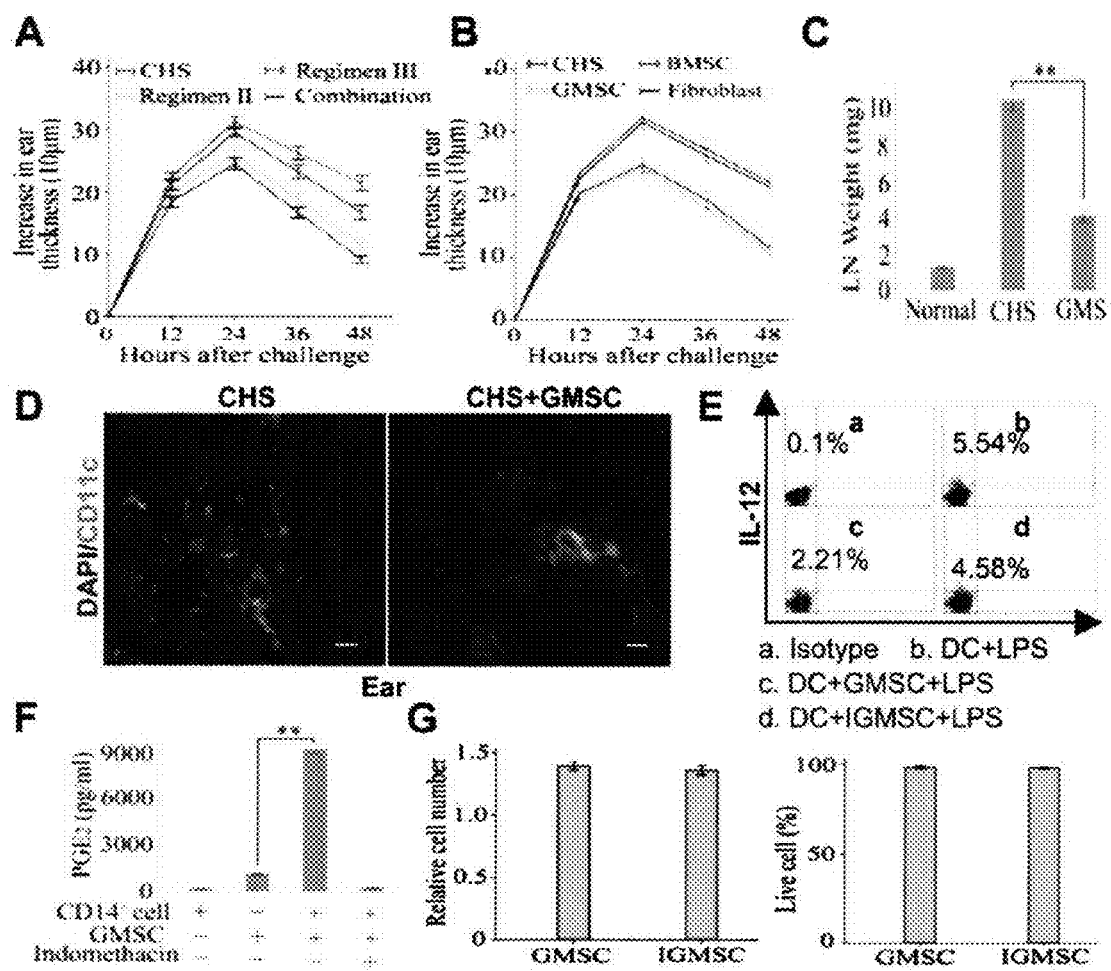
FIG. 15 shows A, GMSCs ($2\times10^6$/mice) were systemically injected into mice via tail vein either one day before challenge (regimen II) or one hour after challenge with 1% oxazolone (regimen III), or in combination of regimen II and HI (combination). B, BMSCs or fibroblasts (FB) ($2\times10^6$/mice) were systemically injected into mice via tail vein 1 day before challenge (regimen II). Ear thickness (n=4) was measured at the indicated times. C and Z), Following treatment regiment II with GMSCs, dLNs were collected and weighed (Q, and the infiltration of $CD11c^+$ DCs in the CHS ears was determined by immunofluorescence staining (D). E, Flow cytometric analysis of intracellular IL-12 expression by DCs stimulated by LPS after co-cultured with GMSCs or indomethacin-pretreated GMSCs (IGMSC) in transwells for 72 h. F, GMSCs were co-cultured with $CD14^+$ monocytes in the presence or absence of indomethacin (5|iM) for 72 h and $PGE_2$ production in the supernatant was determined by EIA. G, GMSCs were pretreated with different concentrations of indomethacin for 24 h and cell viability was determined by MTT assay. The results represent three independent experiments (mean±SEM). *P<0.05; **P<0.01.

According to the specific disease course of CHS, we first investigated the efficacy of GMSC treatment intervention at different stages of delayed type hypersensitivity (DHS) (FIG. 8A). To this purpose, GMSCs ($2 \times 10^6$/mice) were systemically injected into mice either at 1 day before sensitization with 1% oxazolone (treatment regimen I), 1 day before challenge (treatment regimen II), or 1 h after challenge (treatment regimen III) with 1% oxazolone, and the extent of swelling/inflammation in terms of external ear thickness was carefully measured at the intervals of 12 h. Our results showed that systemic infusion of GMSCs consistently led to attenuation of CHS appearance manifested clinically as a reduction of ear thickness as compared to untreated CHS mice (FIG. 8B). GMSC treatment intervention at different phases of DHS yielded variable therapeutic effects, whereas early intervention prior to antigen sensitization (treatment regimen I) exhibited the best efficacy, followed by treatment regimens II and III, respectively, characterized by a decrease in ear thickness and inflammation that appeared as early as 12 h (I or II v.s. III, $P<0.05$), and more apparently in the next 24-48 h after the first challenge (I or II v.s. III, $P<0.01$) (FIGS. 8B and C). Even though the therapeutic effect of treatment regimen I appeared more pronounced than that of treatment regimen II, the difference was not statistically significant (I v.s. II, $P>0.05$). In addition, treatment regimen II in combination with III appeared more effective in suppressing CHS than treatment regimen I or II alone; however, the difference is not statistically significant ($P>0.05$) (FIG. 15A). Similar therapeutic effects were observed after treatment with bone marrow-derived MSCs one day before challenge (treatment regimen II), but treatment with skin fibroblasts showed no obvious therapeutic effects on CHS (FIG. 15B). Taken together, these findings indicate that systemic infusion of GMSCs before sensitization and challenge yielded optimal treatment effect on CHS. Therefore, we chose treatment regimen H in most of the following studies unless specifically indicated.

Further analysis of ear specimens and regional dLNs harvested 48 h after challenge showed a markedly reduction in infiltration of inflammatory cells and gross LN weight in GMSC-treated mice as compared to untreated CHS controls (FIG. 8D and FIG. 15C). We next investigated the in vivo effects of GMSCs on the production of local inflammatory cytokines at the CHS sites. Results from both Western blot and ELISA showed a significant increase in the expression of NF-κB p65 and pro-inflammatory cytokines including TNF-α, IL-6 and IFN-γ in CHS ear tissue lysates as compared to those of normal controls, whereas treatment with GMSCs significantly decreased the local expression of these inflammation-related genes (FIGS. 8E and F). These findings indicate that GMSCs are capable to harness delayed-type hypersentivity reactions by suppressing a variety of inflammatory cytokines and gene products.

Example II.B

GMSCs Attenuate CHS Via PGE2-Dependent Inhibition of DCs

Previous studies have demonstrated that DCs play a critical role in the initiation of CHS (67-70), while bone marrow- and adipose-derived MSCs are capable to inhibit their immune functions (71). Here, we postulated that attenuation of CHS by GMSCs might involve the inhibition of DC functions. To test our hypothesis, GMSCs ($2 \times 10^6$/mice) were systemically injected into mice one day before sensitization and sacrificed 2 days after challenge. Immunostaining showed that GMSC treatment robustly reduced the number of $CD11c^+$ DCs at both the regional dLNs (FIG. 9A) and the antigen challenged ears (FIG. 15D). The reduction in the number of $CD11c^+$ DCs in LNs caused by GMSC treatment was further confirmed by flow cytometric analysis (FIG. 9B).

We next performed a series of in vitro studies to confirm the inhibitory effect of GMSCs on DCs. To this end, $CD14^+$ monocytes purified from peripheral blood mononuclear cells (PBMCs) of healthy donors were co-cultured with identical number of GMSCs (1:1) under the condition of direct cell-cell contact or in a transwell system in the DC-induction medium containing GM-CSF (20 ng/mL) and IL-4 (20 ng/mL), whereas $CD14^+$ monocytes were cultured alone under the same condition and served as controls, After 7 days, DC differentiation was assessed by flow cytometric analysis for expression of CD11c and the co-stimulatory molecule, CD80, both are cell surface molecules expressed by matured DCs. As shown in FIG. 9C, GMSCs co-cultured with $CD14^+$ monocytes under both cell-cell contact and transwell conditions significantly inhibited the differentiation and maturation of DCs, characterized by a reciprocal increase in the expression of CD14 and a decrease in the expression of CD11c and CD80, as compared with $CD14^+$ monocytes-derived DCs cultured alone (FIG. 9C). Functionally, we found co-culture with GMSCs dramatically reduced IL-12 secretion by DCs in response to LPS stimulation (FIG. 9D), which was further confirmed by flow cytometry after intracellular staining (FIG. 15E). These results indicate that soluble factors contribute to GMSC-mediated inhibitory effects on the differentiation and activation of DCs.

To further define specific secretory factors involved in GMSC-mediated inhibition of DCs, monoclonal neutralizing antibodies specific for TGF-β1 and IL-10 (10 μg/ml), or specific inhibitor of IDO (1-MT, 500 μM), or specific inhibitor of COX-1/2 (indomethacin, 5 μM), were applied to the co-culture system. We found that neutralizing TGF-β1 or IL-10 and pretreatment with 1-MT showed no obvious effects on GMSC-mediated inhibitory effects on DCs (data not shown). On the contrary, pretreatment of GMSCs with 5 μM indomethacin significantly but not completely reversed their inhibitory effect on DC differentiation (FIG. 9E) and LPS-stimulated IL-12 secretion by DCs (FIG. 9D and FIG. 15E); while this concentration of indomethacin could completely abolish $PGE_2$ production stimulated by co-cultured $CD14^+$ monocytes without cytotoxicity (FIGS. 15F and G). These results indicate that GMSC-derived $PGE_2$ plays a crucial role in GMSC-mediated inhibitory effect on DCs.

Next, we asked whether $PGE_2$ is essential for GMSCs-mediated desensitizing of CHS and the associated decrease in the number of DCs at regional LNs. GMSCs ($2 \times 10^6$/mice) pretreated with indomethacin were systemically injected into mice one day before sensitization (treatment regimen I) or one day before challenge (treatment regimen II). Our results showed that GMSCs pretreated with indomethacin lost their inhibitory capacity on DC infiltration in LNs collected following treatment regimen I (FIG. 16A); and more importantly, indomethacin treated GMSCs lost their capacity to attenuate CHS under both treatment regimens as compared to untreated GMSC (FIGS. 16B and C). These compelling findings support the notion that PGE-2 is indispensable to GMSC-mediated inhibition of DC functions both in vitro and in vivo, which might contribute, at least in part, to the underlying mechanism of GMSC-induced immunosuppression in CHS.

Example II.C

Figure 17:
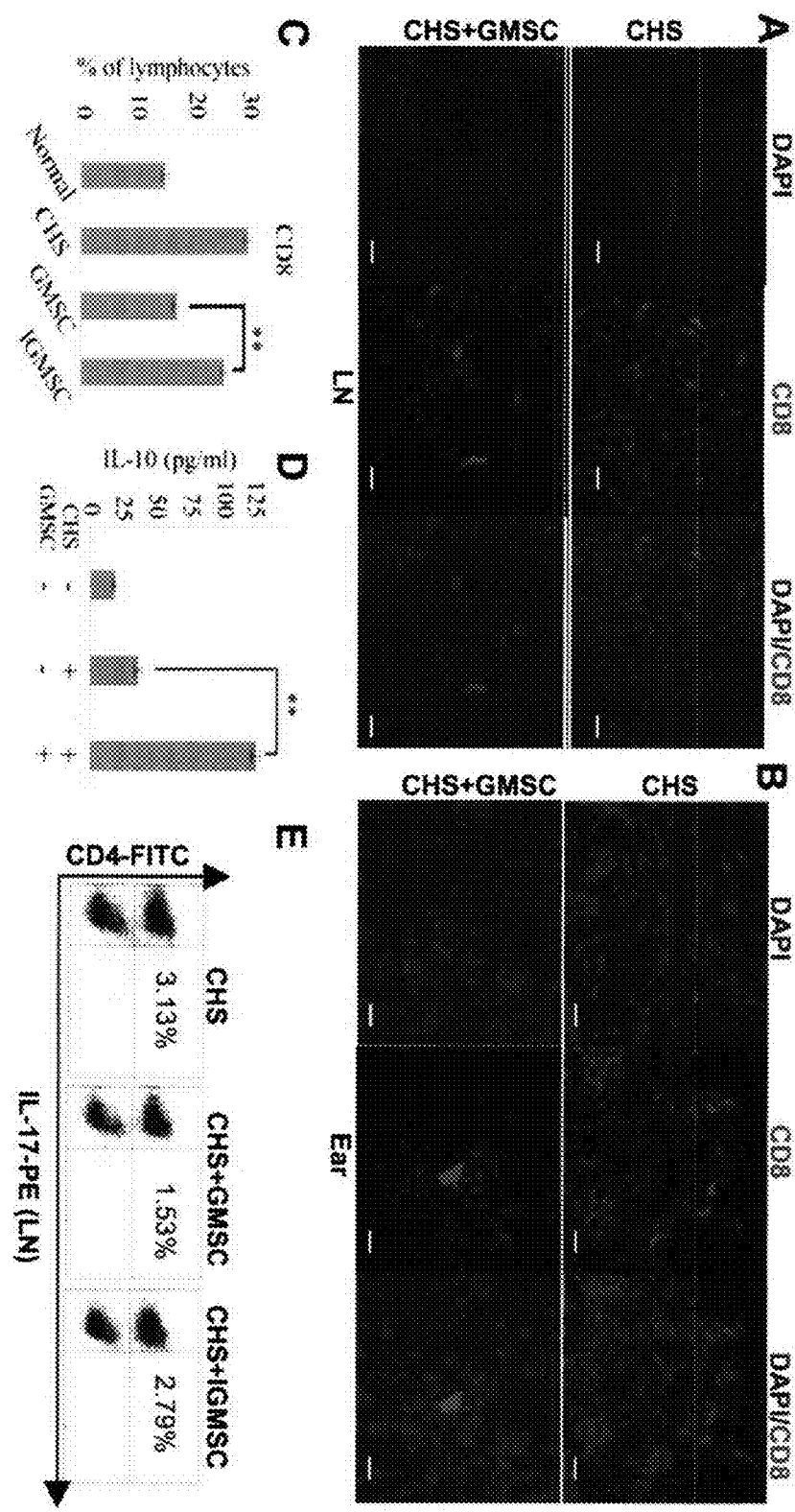
FIG. 17 shows that GMSCs or GMSCs pretreated with 5 μM indomethacin (IGMSC) ($2\times10^6$/mice) were systemically injected into mice via tail vein 1 day before challenge with 1% oxazolone (regimen II). 48 h after challenge, ear samples and dLNs were collected for further analysis. A and B, The infiltration of $CD8^+$ T cells in dLNs and CHS ears was determined by immunofluorescence staining. C, Quantification of $CD8^+$ T cells in CHS ears. D, IL-10 levels in local CHS ears were determined using ELISA. E, The infiltration of $T_H17$ cells in dLNs was determined using flow cytometry. The results represent three independent experiments (mean±SEM). *P<0.05; **P<0.01.

Attenuation of CHS by GMSCs is Associated with their Modulatory Effects on Multiple Effector T Cells Besides DCs, multiple sub-types of T lymphocytes, including CD8$^+$ cytotoxic T cells (72, 73) and CD4$^+$ T helper cells, especially $T_H17$ (74-76) and Tregs (77-79), partake different roles in the elicitation and resolution of CHS (62). Here, we postulate that GMSC-mediated immunomodulatory effects on multiple types of T cells also contribute to their desensitizing therapeutic effects on CHS. As expected, systemic injection of GMSCs into mice one day before challenge (treatment regimen II) significantly reduced the infiltration of CD8$^+$ T cells at the regional dLNs and challenged CHS ears as demonstrated by immunostaining (FIG. 17A-C) and flow cytometric analysis (FIG. 10A). Specifically, we observed a reduction in the number of infiltrated $T_H17$ cells in the LNs and a parallel decreased expression of IL-17 in CHS ears after treatment with GMSCs, as compared with CHS controls (FIGS. 10B and C). On the other hand, when compared to CHS controls, GMSC treatment significantly increased not only the expression of FoxP3 (the specific transcriptional factor expressed by Tregs) and the anti-inflammatory cytokine IL-10 (a signature cytokine of Tregs) at the challenged ears, but also the number of infiltrated Tregs at regional LNs as determined by Western blot, ELISA, and flow cytometry, respectively (FIGS. 10C and D and FIG. 17D). Since our results have shown that $PGE_2$ is essential for GMSC-mediated attenuation of CHS and the associated inhibition of DC functions (FIG. 16), we ask whether $PGE_2$ plays a similar role in GMSC-mediated inhibition of effector T cells. As expected, GMSC-mediated inhibition of CD8$^+$ and TH-17 cell infiltration at the LNs was partially reversed when GMSCs were pre-treated with indomethacin prior to systemic injection into mice (FIGS. 17C and E).

Example II.D

Attenuation of CHS by GMSCs is Associated with their Inhibitory Effects on Mast Cells In addition to DCs and multiple sub-types of effector T cells, recent studies have implicated the critical role of mast cells (MCs) in delayed-type allergic reactions (80-88). Thus, we further investigated whether GMSCs had any effects on MC functions and their potential role in GMSC-mediated attenuation of CHS. We first explored the interactions of homed GMSCs with host mast cells at the inflammatory/ challenged ears following systemic infusion of GMSCs pre-labeled with CM-DiI one day before challenge. Our results showed a more robust homing of labeled GMSCs to the challenged ear as compared to the opposite normal ear (FIG. 11A); the homed GMSCs were in close proximity with FcεRIα positive mast cells as shown by laser confocal microscopy (FIG. 11B). We next investigated the in vivo effects of GMSCs on the degranulation functions of mast cells at the challenged ears. Toluidine blue staining showed that the number of mast cells and the percentage of degranulated mast cells dramatically decreased in GMSC-treated mice ears as compared to the untreated group (FIGS. 11C and D), whereas such inhibitory effects on MCs were significantly attenuated when GMSCs were pre-treated with indomethacin before systemic injection into mice (FIG. 11D). Altogether, these findings indicate that $PGE_2$ provides a functional link between GMSCs and mast cells and potentially contributes to GMSC-mediated reversal of delayed-type hypersensitivity in CHS model.

Example II.E

Mechanisms Underlying GMSCs-Mediated Inhibition of Mast Cell Functions In Vitro

Figure 12:
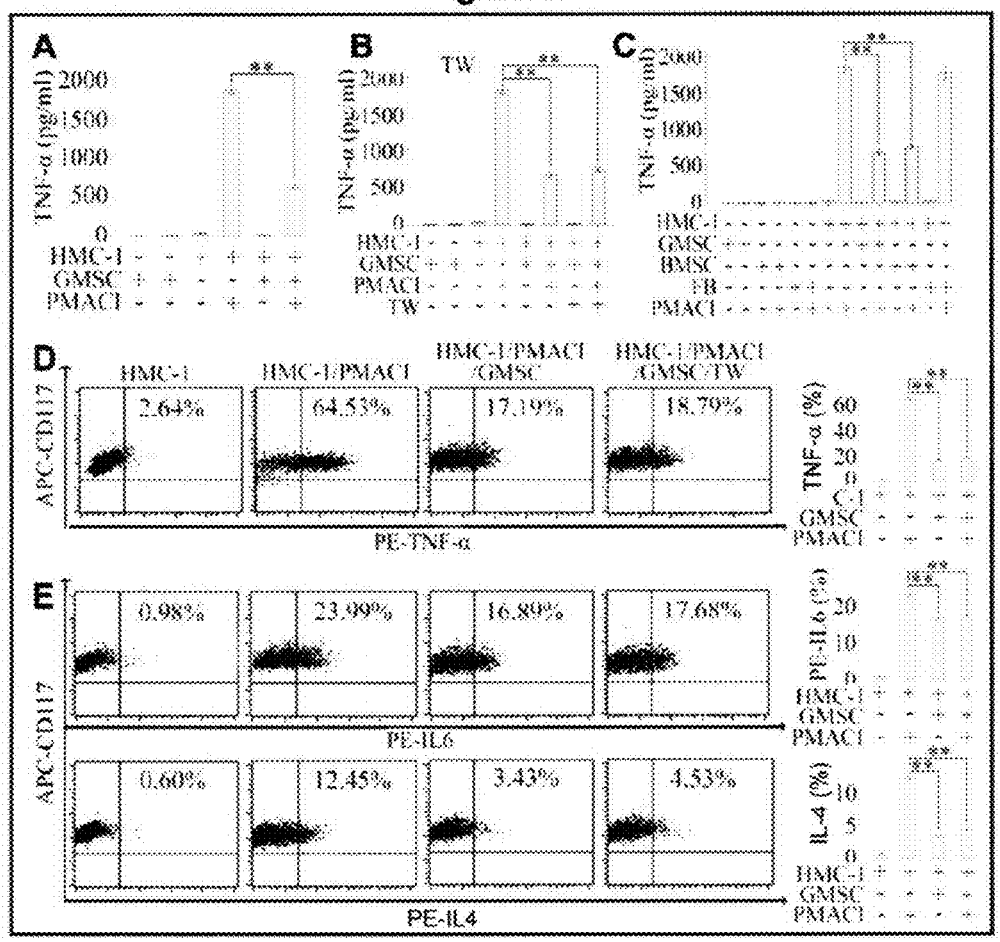
FIG. 12 shows that GMSCs suppress inflammatory cytokines release by HMC-1 cells. HMC-1 cells were co-cultured with GMSCs (1:1) for 72 h under direct cell-cell contact or in a transwell system (TW). A-B, Following stimulation with PMACI, the secretory TNF-α in the supernatants were determined using ELISA. C, HMC-1 cells were co-cultured with bone marrow-derived MSC (BMSC) or skin fibroblasts (FB) (1:1) for 72 h under in transwells. Following stimulation with PMACI, the secretory TNF-α in the supernatants were determined using ELISA. D and E, The PMACI-stimulated expression of intracellular cytokines (TNF-α, IL-4 and IL-6) in HMC-1 after co-culture with GMSCs in transwells were determined by flow cytometry. The results represent three independent experiments (mean±SEM). *P<0.05; **P<0.01.
Figure 18:
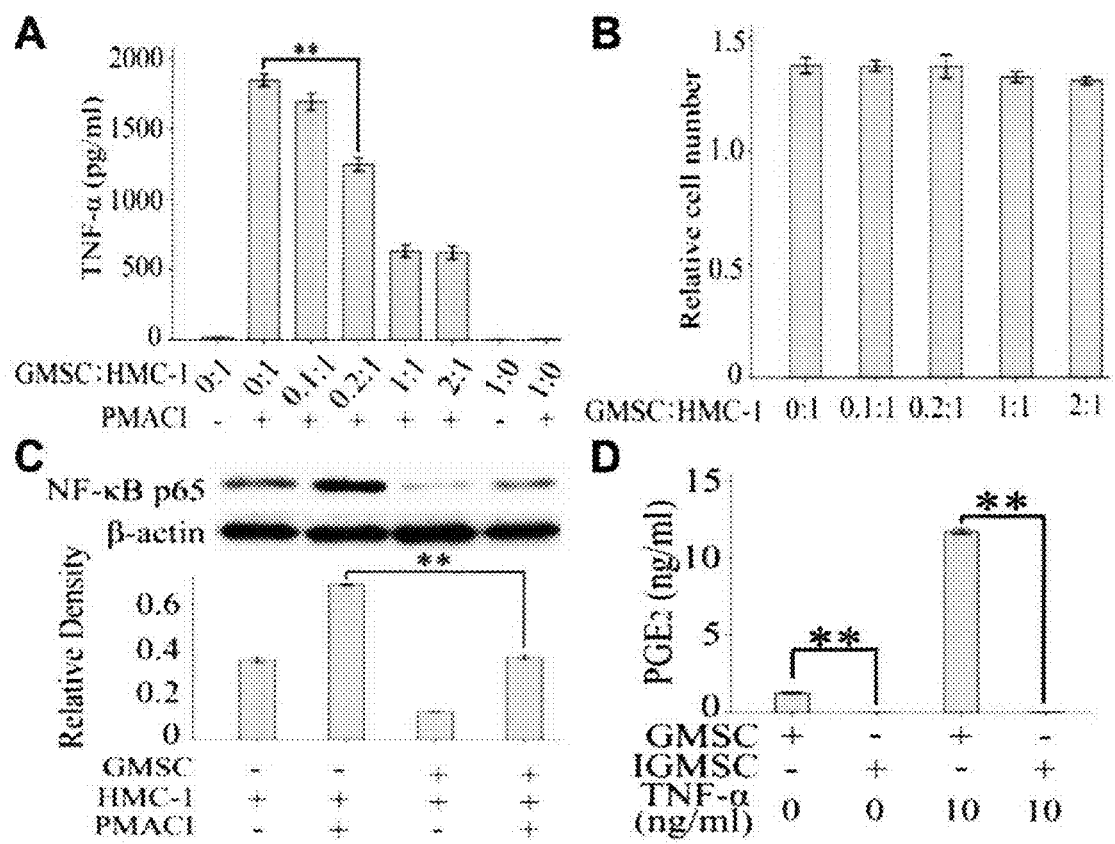
FIG. 18 shows HMC-1 cells were co-cultured with increasing number of GMSCs for 72 under the condition of direct cell-cell contact (A) or in transwells (B and Q followed by stimulation with PMACI, A, The secretion of TNF-a in the supernatant was determined using ELISA. B, The number of HMC-1 cells was counted with a hemacytometer under a microscope. C, The expression of NF-kB p65 by HMC-1 cells was determined by Western blot. D, GMSCs with or without pretreatment with 5\xM indomethacin were exposed to 10 ng/mL TNF-α for 24 h. The $PGE_2$ production in the supernatant was determined using EIA. The results represent three independent experiments (mean±SEM). *P<0.05; **P<0.01.

Next, we performed a series of in vitro studies to explore the interplay between GMSCs and mast cells and their potential mechanisms. To this purpose, HMC-1 cells, an established human mast cell line, were co-cultured with GMSCs at different ratios of cell density under direct cell-cell contact for 72 h, followed by stimulation with PMA and calcium ionophore (PMACI) for another 18 h. The production of TNF-α in the supernatants of mast cells or GMSCs cultured alone and their co-cultures was measured by ELISA. Our results showed that co-culture with GMSCs under direct cell-cell contact led to a cell-dose dependent inhibition of PMACI-stimulated TNF-α release by HMC-1 cells (FIG. 18A), with a maximum inhibition at equal cell density ratio (P<0.01) (FIG. 18A and FIG. 5A). To determine whether inhibition of TNF-α release by GMSCs is dependent on direct cell-cell contact and/or soluble factors, HMC-1 cells and GMSCs were co-cultured in the transwell system. As shown in FIG. 12B, co-culture with GMSCs in transwells decreased PMACI-stimulated TNF-α release to a similar extent as compared with direct co-culture, implying that soluble factors may play an essential role. However, co-culture with an increasing number of GMSCs in transwells had no obvious effect on the proliferation of HMC-1 cells, therefore, ruled out the possibility that GMSC-mediated inhibition of mast cell activation was due to the inhibition of cell proliferation (FIG. 18B). Similar to above findings, a reproducible reduction of PMACI-stimulated TNF-α production in co-culture with bone marrow-derived MSCs was observed (P<0.01), whereas no obvious changes were detected in co-cultures with normal skin fibroblasts (P>0.05) (FIG. 12C). Substantially, the inhibitory effects of GMSCs on MC activation were further confirmed by flow cytometric analysis, which showed a significant decrease in the percentage of HMC-1 cells expressing TNF-α, IL-6 and IL-4 among total CD117$^+$ (c-kit) HMC-1 cells co-cultured with GMSCs under both direct cell-cell contact and transwell system following stimulation with PMACI (P<0.01) (FIGS. 12D and E). Of note, PMACI-stimulated up-regulation of NFκB p65 was also abolished in HMC-1 cells when co-cultured with GMSCs in transwell as compared to HMC-1 cells cultured alone (FIG. 18C), which was apparently correlated with GMSC-mediated inhibition of TNF-α secretion by PMACI-activated HMC-1 cells. Taken together, these results indicate that GMSCs can potently inhibit MC activation through secretory soluble factors.

We then aimed to identify the specific secretory soluble factors that potentially contributed to GMSC-mediated inhibition of pro-inflammatory cytokine synthesis by mast cells. To this end, monoclonal neutralizing antibodies specific for TGF-β1 and IL-10 (10 m/ml), or a specific inhibitor for IDO (1-MT, 500 μM), were added into the co-culture. Our results indicated that blocking these factors failed to restore GMSC-mediated inhibition of TNF-α release by HMC-1 cells in response to PMACI stimulation (FIG. 13A). Our results from in vivo studies have assumed the potential role of $PGE_2$ in GMSC-mediated inhibition of MC functions during CHS (FIG. 11). To confirm this, we then pretreated GMSCs with indomethacin for 24 h and then co-cultured with HMC-1 cells in transwells followed by PMACI stimulation. We found that GMSCs pretreated with indomethacin lost their ability to inhibit PMACI-stimulated TNF-α release by HMC-1 cells (FIG. 13A). Flow cytometric analysis further demonstrated that pretreatment of GMSCs with indomethacin reversed their inhibitory effects on PMACI-activated HMC-1 cells in terms of TNF-α, IL-6 or IFN-γ expression (FIG. 13B). These findings indicate that $PGE_2$ plays a critical role in GMSC-mediated inhibition of de novo synthesis of pro-inflammatory cytokines by mast cells.

To further dissect the mechanisms whereby $PGE_2$ contributes to GMSC-mediated inhibition of mast cell activation, we first exposed GMSCs to different concentrations of exogenous INF-α for 24 h, and the expression of COX-2 and production of $PGE_2$ were determined by Western blot and ELISA, respectively. Our results showed TNF-α treatment led to a dose-dependent increase in COX-2 expression and $PGE_2$ production by GMSCs (FIGS. 14A and B). As expected, indomethacin-pretreated GMSCs failed to produce $PGE_2$ in response to stimulation with exogenous TNF-α (FIG. 18D). On the other hand, treatment with exogenous $PGE_2$ inhibited PMACI-stimulated TNF-α secretion by HMC-1 cells in a dose-dependent manner (FIG. 14B). In addition, the expression of COX-2/$PGE_2$ was mildly elevated in co-cultured GMSCs and HMC-1 without PMACI stimulation, but such an increase was significantly augmented in the presence of PMACI stimulation (FIG. 14C). Likewise, the enhanced expression of COX-2 $PGE_2$ induced by PMACI-activated HMC-1 cells was abolished in the presence of TNF-α neutralizing antibody (FIG. 14D). Taken together, these results indicate that a critical feedback loop conferred by TNF-α/$PGE_2$ axis might play a key role in the cross-talks between mast cells and GMSCs.

Materials and Methods for Example II

Animals.

BALB/c mice (male, 8-10 week-old) were obtained from Jackson Laboratories (Bar Harbor, Me.) and group-housed at the Animal Facility of University of Southern California (USC). All animal care and experiments were performed under institutional protocols approved by the Institutional Animal Care and Use Committee (IACUC) at USC.

Antibodies and Reagents.

Lipopolysaccharides (LPS), Phorbol 12-myristate 13-acetate (PMA), A23187, indomethacin, oxazolone and brefeldin A were from Sigma (St. Louis, Mo.). Antibodies include anti-CD117-APC, anti-FcεRIα-FITC, anti-IL-6-PE, anti-IL-4-PE, anti-TNF-α-PE anti-CD4-PerCP-Cy5.5, anti-CD25-PE, and anti-FoxP3-FITC (eBiosciences, San Diego, Calif.).

Cell Culture.

Human gingival samples were collected from healthy subjects following routine dental procedures at USC School of Dentistry under the approved Institutional Review Board (IRB). Gingiva-derived mesenchymal stem cells (GMSCs) were isolated and cultured as previously described (64).

$CD14^+$ cells were negatively selected from PBMCs using the MACS CD14 MicroBeads (Monocyte Isolation Kit, Miltenyi Biotec, Auburn, Calif.) according to the manufacturer's instructions. Purity of isolated monocytes was assessed by flow cytometry. Cells were then cultured in 6-well plates in RPMI 1640 medium supplemented with 10% fetal bovine serum (FBS), 1% penicillin/streptomycin, 1% L-glutamine (Invitrogen), and recombinant GM-CSF (20 ng/mL) and IL-4 (20 ng/mL) (PeproTech, Rocky Hill, N.J.).

The human mast cell line HMC-1 was kindly provided by Dr. J. H Butterfield (Mayo Clinic, Rochester, Minn.) (65). Cells were maintained in Iscove's modified Dulbecco's medium (IMDM) supplemented with 10% fetal bovine serum, 100 IU/ml penicillin and 100 μg/ml streptomycin. For co-culture studies, indicated cells were co-cultured with GMSCs in either direct cell-cell contact or in transwells as described (58, 64). Neutralizing Abs specific for human IL-10, TGF-β1, TNF-α, or an isotype-matched mAb (10 μg/ml; R&D Systems), or IDO inhibitor (1-methyl-L-tryptophan, I-MT; Sigma-Aldrich) were used for certain experimental purposes. Under certain conditions, GMSCs were pretreated with 5 μM indomethacin (Sigma-Aldrich) to block the production of $PGE_2$ and then co-cultured with indicated cells.

Flow Cytometry.

Cell surface markers and intracellular cytokine were analyzed using a FACS Calibur (BD Biosciences) following standard protocols.

Treatment of Contact Hypersensitivity (CHS) by GMSCs.

The murine CHS model was induced as described previously (66). Briefly, 20 μl of a 1% oxazolone solution in acetone/sesame seed oil (4:1) was applied to the right ear. 7 days later, the sensitized right ears were challenged with 20 μl of 1% oxazolone. An identical amount of acetone/sesame seed oil (4:1) was administered to the left ear as control. Based on the disease course of CHS, different treatment regimens were performed, whereby GMSCs pre-labeled with CM-DiI ($2.0 \times 10^6$/mice) were intravenously injected into mice either one day before sensitization (treatment regimen I), or one day before initiation or challenge (treatment regimen II), or one hour after challenge (treatment regimen III) (FIG. 8, A). Control group received PBS only or normal skin-derived fibroblasts (n=4). Ear thickness was measured in a blind way at indicated time points. Mice were sacrificed on day 2 after challenge and ear samples were harvested for further analysis.

Immunohistochemical and Western Blot Analysis.

H & E and toluidine blue staining was performed on paraffin-embedded sections for histological and mast cell examination. Immunofluorescence studies were performed using specific antibody for mice FcεRIα. For semi-quantification, positive signals in at least 5 random high-power fields (HPF) were visualized and counted. Western blot analysis was performed as previously described (64), with antibodies specific for mice TNF-α, IL-6, IL-4, IFN-γ, IL-10 (Biolegend, San Diego, Calif.), or human COX-2, NF-κB p65 (Millipore, Billerica, Mass.) or β-actin (Sigma).

ELISA.

The concentration of cytokines in ear lysates and the supernatants of cultured cells were detected using ELISA kits (eBioscience). The production of $PGE_2$ in supernatants was determined using an EIA kit (Cayman Chemical).

Statistical Analysis.

All data are expressed as mean±SEM from at least three independent experiments. Differences between experimental and control groups were analyzed by two-tailed unpaired Student's t-test using SPSS. P-values less than 0.05 were considered statistically significant.

All publications cited herein are expressly incorporated herein by reference in their entirety.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Those skilled in the art will recognize, or be able to ascertain using no more than routine experimentation, many equivalents to the specific embodiments of the method and compositions described herein. Such equivalents are intended to be encompassed by the following claims.

REFERENCES

The following references are incorporated herein by reference.
1. Pittenger M F, Mackay A M, Beck S C et al. Multilieage potential of adult human mesenchymal stem cells. Science 1999; 284: 143-147.
2. Friedenstein A J, Chailakhjan R K, Lalykina K S. The development of fibroblast colonies in monolayer cultures of guinea-pig bone marrow and spleen cells. Cell Tissue Kinet 1970; 3: 393-403.
3. Nauta A J, Fibbe W E. Immunomodulatory properties of mesenchymal stromal cells. Blood 2007; 110: 3499-3506.
4. Uccelli A, Morena L, Pistoia V. Mesenchymal stem cells in health and disease. Nat Rev Immunol 2008; 8: 726-736.
5. Aggarwal S, Pittenger M F. Human mesenchymal stem cells modulate allogeneic immune cell responses. Blood 2005; 105: 1815-1822.
6. Ryan J M, Barry F, Murphy J M et al. Interferon-gamma does not break, but promotes the immunosuppressive capacity of adult human mesenchymal stem cells. Clin Exp Immunol 2007; 149: 353-363.
7. Selmani Z, Naji. A, Zidi I et al. Human leukocyte antigen-G5 secretion by human mesenchymal stem cells is required to suppress T lymphocyte and natural killer function and to induce $CD4^+CD25^{high}FoxP3^+$ regulatory T cells. Stem Cells 2008; 26: 212-222.
8. Spaggiari G M, Capobianco A, Abdelrazik H et al. Mesenchymal stem cells inhibit natural killer-cell proliferation, cytotoxicity, and cytokine production: role of indoleamine 2,3-dioxygenase and prostaglandin E2. Blood 2008; 111: 1327-1333.
9. Spaggiari G M, Abdelrazik H, Becchetti F et al. MSCs inhibit monocyte-derived DC maturation and function by selectively interfering with the generation of immature DCs: central role of MSC-derived prostaglandin E2. Blood 2009; 113: 6576-6583.
10. O'Brien J, Lyons T, Monks J et al. Alternatively activated macrophages and collagen remodeling characterize the postpartum involuting mammary gland across species. Am Pathol 2010; 176: 1241-1255.
11. Fairweather D, Cihakova D. Alternatively activated macrophages in infection and autoimmunity. J Autoimmun 2009; 33: 222-230.
12. Troidl C, Möllmann H, Nef H et al. Classically and alternatively activated macrophages contribute to tissue remodelling after myocardial infarction. J Cell Mol Med 2009; 13: 3485-3496.
13. Bystrom J, Evans I, Newson J et al. Resolution-phase macrophages possess a unique inflammatory phenotype that is controlled by cAMP. Blood 2008; 112: 4117-4127.
14. Martinez F O, Helming L, Gordon S. Alternative activation of macrophages: an immunologic functional perspective. Annu Rev Immunol 2009; 27: 451-483.
15. Nemeth K, Leelahavanichkul A, Yuen P S et al. Bone marrow stromal cells attenuate sepsis via prostaglandin E (2)-dependent reprogramming of host macrophages to increase their interleukin-10 production. Nat Med 2009; 15:42-49.
16. Aki K, Shimizu A, Masuda Y et al. ANG II receptor blockade enhances anti-inflammatory macrophages in anti-glomerular basement membrane glomerulonephritis. Am J Physiol Renal Physiol 2010; 298: F870-F882.
17. Hunter M M, Wang A, Parhar K S S et al. In vitro-derived alternatively activated macrophages reduce colonic inflammation in mice. Gastroenterology 2010; 138:1395-1405.
18. Wang Y, Wang Y P, Zheng G et al. Ex vivo programmed macrophages ameliorate experimental chronic inflammatory renal disease. Kidney Int 2007; 72: 290-299.
19. Smith P, Mangan N E, Walsh C M et al. Infection with a helminth parasite prevents experimental colitis via a macrophage-mediated mechanism. J Immunol 2007; 178: 4557-4566.
20. Kim J, Hematti P. Mesenchymal stem cell-educated macrophages: a novel type of alternatively activated macrophages. Exp Hematol 2009; 37: 1445-1453.
21. Maggini J, Mirkin G, Bognanni I et al. Mouse bone marrow-derived mesenchymal stromal cells turn activated macrophages into a regulatory-like profile. PLoS One 2010; 5: e9252.
22. Ohtaki H, Ylostalo J H, Foraker J E et al. Stem/progenitor cells from bone marrow decrease neuronal death in global ischemia by modulation of inflammatory/immune responses. Proc Natl Acad Sci USA 2008; 105: 14638-14643.
23. Erring S A, Krieg T, Davidson J M. Inflammation in wound repair: molecular and cellular mechanisms. J Invest Dermatol 2007; 127: 514-525.
24. Stappenbeck T S, Miyoshi H. The role of stromal stem cells in tissue regeneration and wound repair. Science 2009; 324:1666-1669.
25. Mirza R, DiPietro L A, Koh T J. Selective and specific macrophage ablation is detrimental to wound healing in mice. Am J Pathol 2009; 175: 2454-2462.
26. Menzies F M, Henriquez F L, Alexander J et al. Sequential expression of macrophage anti-microbial/inflammatory and wound healing markers following innate, alternative and classical activation, Clin Exp Immunol 2010 Jan. 5. [Epub ahead of print]
27. Daley J M, Brancato S K, Triomay A A, Reichner J S, Albina J E. The phenotype of murine wound macrophages. J Leukoc Biol 2010; 87: 59-67.
28. Chen L, Tredget E E, Wu P Y et al. Paracrine factors of mesenchymal stem cells recruit macrophages and endothelial lineage cells and enhance wound healing. PLoS One 2008; 3: e1886.
29. Chen L, Tredget E E, Liu C et al. Analysis of allogenicity of mesenchymal stem cells in engraftment and wound healing in mice. PLoS One 2009; 4: e7119.
30. Sasaki M, Abe R, Fujita Y et al. Mesenchymal stem cells are recruited into wounded skin and contribute to wound repair by transdifferentiation into multiple skin cell type. J Immunol 2008; 180: 2581-2587.
31. Wu Y, Chen L, Scott P G et al. Mesenchymal stem cells enhance wound healing through differentiation and angiogenesis. Stem Cells 2007; 25: 2648-2659.

32. Zhang Q, Shi S, Liu Y et al. Mesenchymal stem cells derived from human gingiva are capable of immunomodulatory functions and ameliorate inflammation-related tissue destruction in experimental colitis. J Immunol 2009; 183: 7787-7798.

33. Puig-Kröger A, Serrano-Gómez D, Caparrós E et al. Regulated expression of the pathogen receptor dendritic cell-specific intercellular adhesion molecule 3 (ICAM-3)-grabbing nonintegrin in THP-1 human leukemic cells, monocytes, and macrophages. J Biol Chem 2004; 279: 25680-25688.

34. Gonzalez-Rey E, Anderson P, González M A et al. Human adult stem cells derived from adipose tissue protect against experimental colitis and sepsis. GUT. 2009; 58: 929-939.

35. Alex P, Zachos N C, Nguyen T et al. Distinct cytokine patterns identified from multiplex profiles of murine DSS and TNBS-induced colitis. Inflamm Bowel Dis 2009; 15: 341-352.

36. Tiemessen M M, Jagger A L, Evans H G et al. CD4+CD25+Foxp3+ regulatory T cells induce alternative activation of human monocytes/macrophages, Proc Natl Acad Sci USA 2007; 104: 19446-19451.

37. Huang H, Kim H J, Chang E J et al. IL-17 stimulates the proliferation and differentiation of human mesenchymal stem cells: implications for bone remodeling. Cell Death Differ 2009; 16: 1332-1343.

38. Routley C E, Ashcroft G S. Effect of estrogen and progesterone on macrophage activation during wound healing. Wound Repair Regen 2009; 17: 42-50.

39. Park-Min K H, Antoniv T T, Ivashkiv L B. Regulation of macrophage phenotype by long-term exposure to IL-10. Immunobiology 2005; 210: 77-86.

40. Savage N D, de Boer T, Walburg K V et al. Human anti-inflammatory macrophages induce Foxp3+GITR+CD25+ regulatory T cells, which suppress via membrane-bound TGF-1. J Immunol. 2008; 181: 2220-2226.

41. Weber M S, Prod'homme T, Youssef S et al. Type II monocytes modulate T cell-mediated central nervous system autoimmune disease. Nat Med 2007; 13: 935-943.

42. Grant V, King A E, Faccenda E et al. PGE/cAMP and GM-CSF synergise to induce a pro-tolerance cytokine profile in monocytic cell lines. Biochem Biophys Res Commun 2005; 331: 187-193.

43. Chen G H, Olszewski M A, McDonald R A et al. Role of granulocyte macrophage colony-stimulating factor in host defense against pulmonary *Cryptococcus neoformans* infection during murine allergic bronchopulmonary mycosis. Am J Pathol 2007; 170: 1028-1040.

44. Kuroda E, Ho V, Ruschmann J et al. SHIP represses the generation of IL-3-induced M2 macrophages by inhibiting IL-4 production from basophils. J Immunol 2009; 183: 3652-3660.

45. Roca H, Varsos Z S, Sud S et al. CCL2 and interleukin-6 promote survival of human CD11b+ peripheral blood mononuclear cells and induce M2-type macrophage polarization. J Biol Chem 2009; 284: 34342-34354.

46. Leibovich S J, Ross R. The role of the macrophage in wound repair. A study with hydrocortisone and antimacrophage serum. Am J Pathol 1975; 78: 71-100.

47. Deonarine K, Panelli M C, Stashower M E et al. Gene expression profiling of cutaneous wound healing. J Transl Med 2007; 5:11.

48. Kim W S, Park B S, Sung J H. The wound-healing and antioxidant effects of adipose-derived stem cells. Expert Opin Biol Ther 2009; 9: 879-887.

49. Nauta, A J., Fibbe, W. E. 2007. Immunomodulatory properties of mesenchymal stromal cells. Blood 110: 3499-3506.

50. Uccelli, A., Moretta, L., Pistoia, V. 2008. Mesenchymal stem cells in health and disease. *Nat. Rev. Immunol.* 8: 726-736.

51. Zhao, S., Wehner, R., Bornhauser, M., Wassmuth, R., Bachmann, M., Schmitz, M. 2010. Immunomodulatory properties of mesenchymal stromal cells and their therapeutic consequences for immune-mediated disorders. Stem Cells Dev. 19: 607-614.

52. Tolar, J., Le, B. K., Keating, A., Blazar, B. R. 2010. Concise review: hitting the right spot with mesenchymal stromal cells. Stem Cells 28: 1446-1455.

53. English, K., French, A., Wood, K. J. 2010. Mesenchymal stromal cells: facilitators of successful transplantation. Cell Stem Cell 7: 431-442.

54. Jarvinen, L., Badri, L., Wettlaufer, S., Ohtsuka, T., Standiford, T. J., Toews, G. B., Pinsky, D. J., Peters-Golden, M., Lama, V. N. 2008. Lung resident mesenchymal stem cells isolated from human lung allografts inhibit T cell proliferation via a soluble mediator. *J. Immunol.* 181: 4389-4396.

55. Kim, J., Hematti, P. 2009. Mesenchymal stem cell-educated macrophages: a novel type of alternatively activated macrophages. *Exp. Hematol.* 37: 1445-1453.

56. Spaggiari, G. M., Abdelrazik, H., Becchetti, F., Moretta, L. 2009. MSCs inhibit monocyte-derived DC maturation and function by selectively interfering with the generation of immature DCs: central role of MSC-derived prostaglandin E2. Blood 113: 6576-6583.

57. Spaggiari, G. M., Capobianco, A., Abdelrazik, H., Becchetti, F., Mingari, M. C., Moretta, L. 2008. Mesenchymal stem cells inhibit natural killer-cell proliferation, cytotoxicity, and cytokine production: role of indoleamine 2,3-dioxygenase and prostaglandin E2. Blood 111: 1327-1333.

58. Zhang, Q. Z., Su, W. R., Shi, S. H., Wilder-Smith, P., Xiang, A. P., Wong, A., Nguyen, A. L., Kwon, C. W., Le, A. D. 2010. Human gingiva-derived mesenchymal stem cells elicit polarization of m2 macrophages and enhance cutaneous wound healing. Stem Cells 28: 1856-1868.

59. Nemeth, K., Keane-Myers, A., Brown, J. M., Metcalfe, D. D., Gorham, J. D., Bundoc, V. G., Hodges, M. G., Jelinek, I., Madala, S., Karpati, S., Mezey, E. 2010. Bone marrow stromal cells use TGF-beta to suppress allergic responses in a mouse model of ragweed-induced asthma. Proc. Natl. Acad. Sci. USA. 107: 5652-5657.

60. Bonfield, T. L., Koloze, M., Lennon, D. P., Zuchowski, B., Yang, S. E., Caplan, A. I. 2010. Human mesenchymal stem cells suppress chronic airway inflammation in the murine ovalbumin asthma model. *Am. J. Physiol. Lung Cell Mol. Physiol.* 299: L760-770.

61. Cho, K. S., Park, H. K., Park, H. Y., Jung, J. S., Jeon, S. G., Kim, Y. K., Roh, H. J. 2009. IFATS collection: Immunomodulatory effects of adipose tissue-derived stem cells in an allergic rhinitis mouse model. Stem Cells. 27: 259-265.

62. Vocanson, M., Hennino, A., Rozieres, A., Poyet, G., Nicolas, J. F. 2009. Effector and regulatory mechanisms in allergic contact dermatitis. Allergy. 64: 1699-1714.

63. Fonacier, L. S., Dreskin, S. C., Leung, D. Y. 2010. Allergic skin diseases. *J. Allergy Clin. Immunol.* 125: S138-149.

64. Zhang, Q., Shi, S., Liu, Y., Uyanne, J., Shi, Y., Shi, S., Le, A. D. 2009. Mesenchymal stem cells derived from human gingiva are capable of immunomodulatory functions and ameliorate inflammation-related tissue destruction in experimental colitis. *J. Immunol.* 183: 7787-7798.
65. Butterfield, J. H., Weiler, D., Dewald, G., Gleich, G. J. 1988. Establishment of an immature mast cell line from a patient with mast cell leukemia. *Leuk. Res.* 12: 345-355.
66. Roberts, L. K., Spangrude, G. J., Daynes, R. A., Krueger, G. G. 1985. Correlation between keratinocyte expression of Ia and the intensity and duration of contact hypersensitivity responses in mice. *J. Immunol.* 135: 2929-2936.
67. Zaba, L. C., Krueger, J. G., Lowes M. A. 2009. Resident and "inflammatory" dendritic cells in human skin. *J. Invest. Dermatol.* 129: 302-308.
68. Kumamoto, Y., Denda-Nagai, K., Aida, S., Higashi, N., Irimura, T. 2009. MGL2 Dermal dendritic cells are sufficient to initiate contact hypersensitivity in vivo. *PLOS ONE* 4: e5619.
69. Fukunaga, A., Khaskhely, N. M., Sreevidya, C. S., Byrne, S. N., Ullrich, S. E. 2008. Dermal dendritic cells, and not Langerhans cells, play an essential role in inducing an immune response. *J. Immunol.* 180 3057-3064.
70. Allan, R. S., Waithman, J., Bedoui, S., Jones, C. M., Villadangos, J. A., Zhan, Y., Lew, A. M., Shortman, K., Heath, W. R., Carbone, F. R. 2006. Migratory dendritic cells transfer antigen to a lymph node-resident dendritic cell population for efficient CTL priming. *Immunity* 25: 153-162.
71. Ivanova-Todorova, E., Bochev, I., Mourdjeva, M., Dimitrov, R., Bukarev, D., Kyurkchiev, S., Tivchev, P., Altunkova, I., Kyurkchiev, D. S. 2009. Adipose tissue-derived mesenchymal stem cells are more potent suppressors of dendritic cells differentiation compared to bone marrow-derived mesenchymal stem cells. *Immunol. Lett.* 126: 37-42.
72. Vocanson, M., Hennino, A., Cluzel-Tailhardat, M., Saint-Mezard, P., Benetiere, J., Chavagnac, C., Berard, F., Kaiserlian, D., Nicolas, J. F. 2006. $CD8^+$ T cells are effector cells of contact dermatitis to common skin allergens in mice. *J. Invest. Dermatol.* 126: 815-820.
73. He, D., Wu, L., Kim, H. K., Li, H., Elmets, C. A., Xu, H. 2006. $CD8^+$ IL-17-producing T cells are important in effector functions for the elicitation of contact hypersensitivity responses. *J. Immunol.* 177: 6852-6858.
74. Zhao, Y., Balato, A., Fishelevich, R., Chapoval, A., Mann, D. L., Gaspari, A. A. 2009. Th17/Tc17 infiltration and associated cytokine gene expression in elicitation phase of allergic contact dermatitis. *Br. J. Dermatol.* 161: 1301-1306.
75. Larsen, J. M., Bonefeld, C. M., Poulsen, S. S, Geisler, C., Skov, L. 2009. IL-23 and T(H)17-mediated inflammation in human allergic contact dermatitis. *J. Allergy Clin. Immunol.* 123: 486-492.
76. Pennino, D., Eyerich, K., Scarponi, C., Carbone, T., Eyerich, S., Nasorri, F., Garcovich, S., Traidl-Hoffmann, C., Albanesi, C., Cavani, A. 2010. IL-17 amplifies human contact hypersensitivity by licensing hapten nonspecific Th1 cells to kill autologous keratinocytes. J. Immunol. 184: 4880-4888.
77. Dubois, B., Chapat, L., Goubier, A., Papiernik, M., Nicolas, J. F., Kaiserlian, D. 2003. Innate $CD4^+CD25^+$ regulatory T cells are required for oral tolerance and inhibition of $CD8^+$ T cells mediating skin inflammation. *Blood* 102: 3295-3301.
78. Ring, S., Karakhanova, S., Johnson, T., Enk, A. H., Mahnke K. 2010. Gap junctions between regulatory T cells and dendritic cells prevent sensitization of CD8(+) T cells. *J. Allergy Clin. Immunol.* 125: 237-246.
79. Ring, S., Oliver, S. J., Cronstein, B. N., Enk, A. H., Mahnke, K. 2009. CD4+CD25+ regulatory T cells suppress contact hypersensitivity reactions through a CD39, adenosine-dependent mechanism. *J. Allergy Clin. Immunol.* 123: 1287-1296.
80. Biedermann, T., Kneilling, M., Mailhammer, R., Maier, K., Sander, C. A., Kollias, G., Kunkel, S. L., Hultner, L., Rocken, M. 2000. Mast cells control neutrophil recruitment during T cell-mediated delayed-type hypersensitivity reactions through tumor necrosis factor and macrophage inflammatory protein 2. *J. Exp. Med.* 192: 1441-1452.
81. Kakurai, M., Monteforte, R., Suto, H., Tsai, M., Nakae, S., Galli, S. J. 2006. Mast cell-derived tumor necrosis factor can promote nerve fiber elongation in the skin during contact hypersensitivity in mice. *Am. J. Pathol.* 169: 1713-1721.
82. Nakae, S., Suto, H., Kakurai, M., Sedgwick, J. D., Tsai, M., Galli, S. J. 2005. Mast cells enhance T cell activation: Importance of mast cell-derived TNF. *Proc. Natl. Acad. Sci. USA.* 102: 6467-6472.
83. Suto, H., Nakae, S., Kakurai, M., Sedgwick, J. D., Tsai, M., Galli, S. J. 2006. Mast cell-associated TNF promotes dendritic cell migration. *J. Immunol.* 176: 4102-4112.
84. Wang, H. W., Tedla, N., Lloyd, A. R., Wakefield, D., McNeil, P. H. 1998. Mast cell activation and migration to lymph nodes during induction of an immune response in mice. *J. Clin. Invest.* 102: 1617-1626.
85. Bryce, P. J., Miller, M. L., Miyajima, I., Tsai, M., Galli, S. J., Oettgen, H. C. 2004. Immune sensitization in the skin is enhanced by antigen-independent effects of IgE. *Immunity* 20: 381-392.
86. Kerdel, F. A., Belsito, D. V., Scotto-Chinnici, R., Soter, N. A. 1987. Mast cell participation during the elicitation of murine allergic contact hypersensitivity. *J. Invest. Dermatol.* 88: 686-690.
87. Kobayashi, M., Nunomura, S., Gon, Y., Endo, D., Kishiro, S., Fukunaga, M., Kitahata, Y. Terui, T., Ra, C. 2010. Abrogation of high-affinity IgE receptor-mediated mast cell activation at the effector phase prevents contact hypersensitivity to oxazolone. *J. Invest. Dermatol.* 130: 725-731.
88. Nishida, K., Hasegawa, A., Nakae, S., Oboki, K., Saito, H., Yamasaki, S., Hirano, T. 2009. Zinc transporter Znt5/Slc30a5 is required for the mast cell-mediated delayed-type allergic reaction but not the immediate-type reaction. *J. Exp. Med.* 206: 1351-1364.
89. Nakae, S., Suto, H., Kakurai, M., Sedgwick, J. D., Tsai, M., Galli, S. J. 2005. Mast cells enhance T cell activation: Importance of mast cell-derived TNF. *Proc. Natl. Acad. Sci. USA.* 102: 6467-6472.
90. Norman, M. U., Hwang, J., Hulliger, S., Bonder, C. S., Yamanouchi, J., Santamaria, P., Kubes, P. 2008. Mast cells regulate the magnitude and the cytokine microenvironment of the contact hypersensitivity response. *Am. J. Pathol.* 172: 1638-1649.
91. Reuter, S., Dehzad, N., Martin, H., Heinz, A., Castor, T., Sudowe, S., Reske-Kunz, A. B., Stassen, M., Buhl, R., Taube, C. 2009. Mast Cells Induce Migration of Dendritic Cells in a Murine Model of Acute Allergic Airway Disease. *Int. Arch. Allergy Immunol.* 151: 214-222.
92. Dawicki, W., Jawdat, D. W., Xu, N., Marshall, J. S. 2010. Mast cells, histamine, and IL-6 regulate the selective influx of dendritic cell subsets into an inflamed lymph node. *J. Immunol.* 184: 2116-2123.

93. Aggarwal, S., Pittenger, M. F. 2005. Human mesenchymal stem cells modulate allogeneic immune cell responses. *Blood* 105: 1815-1822.
94. Chen, K., Wang, D., Du, W. T., Han, Z. B., Ren, H., Chi, Y., Yang, S. G., Zhu, D., Bayard, F., Han, Z. C. 2010. Human umbilical cord mesenchymal stem cells hUC-MSC exert immunosuppressive activities through a PGE2-dependent mechanism. *Clin. Immunol.* 135: 448-458.
95. Highfill, S. L., Kelly, R. M., O'Shaughnessy, M. J., Zhou, Q., Xia, L., Panoskaltsis-Mortari, A., Taylor, P. A., Tolar, J., Blazar, B. R. 2009. Multipotent adult, progenitor cells can suppress graft-versus-host disease via prostaglandin E2 synthesis and only if localized to sites of allopriming. *Blood* 114: 693-701.
96. Nemeth, K., Leelahavanichkul, A., Yuen, P. S., Mayer, B., Parmelee, A., Doi, K., Robey, P. G., Leelahavanichkul, K., Koller, B. H., Brown, J. M., Hu, X., Jelinek, I., Star, R. A., Mezey, E. 2009. Bone marrow stromal cells attenuate sepsis via prostaglandin E(2)-dependent reprogramming of host macrophages to increase their interleukin-10 production. *Nat. Med.* 15: 42-49.
97. Tse, W. T., Pendleton, J. D., Beyer, W. M, Egalka, M. C, Guinan, E. C. 2003, Suppression of allogeneic T-cell proliferation by human marrow stromal cells: implications in transplantation. *Transplantation* 75: 389-397.
98. Matysiak, M., Orlowski, W., Fortak-Michalska, M., Jurewicz, A., Selmaj, K. 2011. Immunoregulatory function of bone marrow mesenchymal stem cells in EAE depends on their differentiation state and secretion of $PGE_2$. *J. Neuroimmunol.* 233: 106-111
99. Bouffi, C., Bony, C., Courties, G., Jorgensen, C., Noel, D. 2010. IL-6-dependent $PGE_2$ secretion by mesenchymal stem cells inhibits local inflammation in experimental arthritis. *PLOS ONE* 5: e14247

What is claimed is:

1. A method of promoting (enhancing) cutaneous wound healing comprising:
    administering to a patient an effective amount of human gingiva-derived mesenchymal stem cells (GMSCs), thereby resulting in at least one of accelerated wound closure, rapid re-epithelialization, improved angiogenesis and improved tissue remodeling relative to untreated controls;
    wherein the GMSCs are administered to an environment comprising a population of macrophages; wherein the GMSCs are in fluid communication with the macrophages; and wherein the effective amount of the GMSCs is an amount sufficient, once administered, to polarize the macrophages.

2. The method of claim 1, wherein said administration results rapid re-epithelialization, improved angiogenesis and improved tissue remodeling relative to untreated controls.

3. The method of claim 1, wherein the administration comprises systemic administration.

4. The method of claim 1, wherein the administration results in accelerated wound closure.

5. The method of claim 1, wherein, said macrophages exhibit by at least one of an increased expression of mannose receptor (MR/CD206), increased expression of IL-10 and IL-6, a suppressed production of TNF-α, and decreased ability to induce Th-17 cell expansion relative to a similar population of untreated macrophages.

6. The method of claim 5, wherein, after the administration, the macrophages are characterized by a suppressed production of TNF-α.

7. A method for attenuating contact hypersensitivity comprising:
    administering to a patient an effective amount of human gingiva-derived mesenchymal stem cells at a time at least timeframe selected from the group consisting of before sensitization, and after sensitization but before challenge, thereby attenuating contact hypersensitivity;
    wherein the GMSCs are administered to an environment comprising a population of macrophages; wherein the GMSCs are in fluid communication with the macrophages; and wherein the effective amount of the GMSCs is an amount sufficient, once administered, to polarize the macrophages.

8. The method of claim 7, wherein the human gingiva-derived mesenchymal stem cells are administered before sensitization.

9. The method of claim 7, wherein the human gingiva-derived mesenchymal stem cells are administered after sensitization but before challenge.

10. The method of claim 7, wherein the administration is systemic administration.

* * * * *

UNITED STATES PATENT AND TRADEMARK OFFICE
CERTIFICATE OF CORRECTION

PATENT NO. : 9,682,105 B2
APPLICATION NO. : 13/809876
DATED : June 20, 2017
INVENTOR(S) : Anh D. Le et al.

Page 1 of 1

It is certified that error appears in the above-identified patent and that said Letters Patent is hereby corrected as shown below:

In the Specification

Column 1, Lines 18-21:
Please delete:
"This invention was made with government support under Contract Nos. CA82422, R01 DE 019932 awarded by the National Institutes of Health. The government has certain rights in the invention."
And insert:
-- This invention was made with government support under R01 DE019932 awarded by the National Institutes of Health. The government has certain rights in the invention. --

Signed and Sealed this
First Day of April, 2025

Coke Morgan Stewart
*Acting Director of the United States Patent and Trademark Office*